US006699860B2

(12) United States Patent
Ladouceur et al.

(10) Patent No.: US 6,699,860 B2
(45) Date of Patent: Mar. 2, 2004

(54) DI-SUBSTITUTED AMINOMETHYL-CHROMAN DERIVATIVE BETA-3 ADRENORECEPTOR AGONISTS

(75) Inventors: Gaetan H. Ladouceur, Branford, CT (US); William H. Bullock, Easton, CT (US); Steven R. Magnuson, Hamden, CT (US); Stephen J. O'Connor, Guilford, CT (US); Roger A. Smith, Madison, CT (US); Quanrong Shen, Indianapolis, IN (US); Qingjie Liu, Milford, CT (US); Ning Su, Milford, CT (US); Emil J. Velthuisen, Irvine, CA (US); Ann-Marie Campbell, Monroe, CT (US); Paul P. Ehrlich, Duesseldorf-Wittlaer (DE)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 10/008,928

(22) Filed: Dec. 7, 2001

(65) Prior Publication Data

US 2003/0078258 A1 Apr. 24, 2003

Related U.S. Application Data

(60) Provisional application No. 60/254,735, filed on Dec. 11, 2000.

(51) Int. Cl.[7] .................... C07D 401/12; C07D 401/14; C07D 311/58; A61K 31/353; A61K 31/4433
(52) U.S. Cl. .................... 514/233.5; 514/309; 514/337; 514/395; 514/456; 514/411; 514/414; 514/443; 514/365; 514/374; 514/320; 514/382; 514/406; 546/141; 546/282.7; 546/283.1; 546/196; 548/305.1; 548/427; 548/454; 548/201; 548/236; 548/252; 548/364.4; 544/151; 549/405; 549/407; 549/51; 549/55
(58) Field of Search .......................... 546/141, 282.7, 546/283.1, 196; 514/309, 337, 395, 456, 411, 414, 443, 233.5, 365, 374, 320, 382, 406; 548/305.1, 427, 454, 201, 236, 252, 364.4; 549/405, 407, 55, 51; 544/151

(56) References Cited

U.S. PATENT DOCUMENTS

| 3,706,764 A | 12/1972 | Nakanishi et al. ......... 260/327 |
| 3,803,176 A | 4/1974 | Christensen et al. ..... 260/345.2 |
| 4,647,579 A | 3/1987 | Kabbe et al. ............... 514/456 |
| 4,650,812 A | 3/1987 | Cohen et al. ............... 514/456 |
| 4,654,362 A | 3/1987 | Van Lommen et al. ...... 514/452 |
| 5,393,775 A | 2/1995 | Le Baut et al. ............. 514/456 |
| 5,451,677 A | 9/1995 | Fisher et al. ................ 546/138 |
| 5,516,917 A | 5/1996 | Djuric et al. ............... 548/525 |
| 5,541,197 A | 7/1996 | Fisher et al. ................ 514/311 |
| 5,561,142 A | 10/1996 | Fisher et al. ................ 514/312 |
| 5,663,194 A | 9/1997 | Newshaw .................... 514/456 |
| 5,977,154 A | 11/1999 | Bell et al. ................... 514/394 |
| 6,051,586 A | 4/2000 | Ladouceur et al. ......... 514/337 |

FOREIGN PATENT DOCUMENTS

| DE | 2511647 | 9/1975 |
| EP | 0079637 | 5/1983 |
| EP | 0091749 | 10/1983 |
| EP | 0328251 | 8/1989 |
| EP | 0611003 | 8/1994 |
| EP | 0801060 | 10/1997 |
| FR | 2746395 | 9/1997 |
| FR | 2746395 | 7/1999 |
| JP | 8198866 | 8/1996 |
| WO | 9429290 | 12/1994 |
| WO | 9525104 | 9/1995 |
| WO | 9529159 | 11/1995 |
| WO | 9735835 | 10/1997 |
| WO | 9746556 | 12/1997 |
| WO | 9832753 | 7/1998 |
| WO | 9932476 | 7/1999 |
| WO | 9965877 | 12/1999 |

OTHER PUBLICATIONS

Balligand (Acta Cinica Belgica, 2000, 55–4, pp. 209–214).*
Donny Strosberg et al. Tips–Oct. 1996 (vol. 17).*
Mewshaw et al., New Generation Dopaminergic Agents, 1. Discovery of a Novel Scaffold which Embraces the D2 Agonist Pharmacophore. Structure–Activity Relationships of a Series of 2–(Aminomethyl)chromans, J. Med. Chem. 40(26):4235–4256, 1997.
Hu, B., Ellingboe, J., Gunawan, I., Han, S., Largis, E., Li, Z., Malamas, M., Mulvey, R., Oliphant, A., Sum, F.–W., Tillett, J., Wong, V., "2,4–Thiazolidinediones as Potent and Selective Human β3 Agonists", Bioorganic & Medicinal Chemistry Letters, 11: 757–760 (2001).
Murata, M., Watanabe, S., and Masuda, Y., "Novel Palladium(0)–Catalyzed Coupling Reaction of Dialkozyborane with Aryl Halides: Convenient Synthetic Route to Arylboronates", J. Org., Chem., 62: 6458–6459 (1997).

* cited by examiner

Primary Examiner—Mark L. Berch
Assistant Examiner—Kahsay Habte
(74) Attorney, Agent, or Firm—Susan M. Pellegrino

(57) ABSTRACT

This invention is related to novel di-substituted aminomethyl chroman derivatives which are useful in the treatment of beta-3 receptor-mediated conditions.

20 Claims, No Drawings

DI-SUBSTITUTED AMINOMETHYL-CHROMAN DERIVATIVE BETA-3 ADRENORECEPTOR AGONISTS

This application claims benefit of U.S. Provisional Application Ser. No. 60/254,735, filed Dec. 11, 2000, the contents of which are incorporated herein by reference in their entirety.

FIELD OF THE INVENTION

This invention relates to novel chroman compounds, pharmaceutical compositions containing such compounds, and methods of treating beta-3 adrenoreceptor-mediated conditions with such compositions.

BACKGROUND OF THE INVENTION

Adrenoreceptors, or adrenergic receptors, are sites on effector organs that are innervated by postganglionic adrenergic fibers of the sympathetic nervous system, and are classified as either alpha-adrenergic or beta-adrenergic receptors. Alpha-adrenergic receptors respond to norepinephrine and to such blocking agents as phenoxybenzamine and phentolamine, whereas beta-adrenergic receptors respond to epinephrine and to such blocking agents as propranolol.

Beta-adrenergic receptors are sub-classified as beta-1, beta-2, and beta-3 adrenoreceptors. Generally, beta-1 stimulation causes cardiostimulation, whereas beta-2 stimulation causes bronchodilation and vasodilation.

Beta-3 receptors are found on the cell surface of both white and brown adipocytes where their stimulation promotes both lipolysis and energy expenditure. Agonists of beta-3 adrenoreceptors are known to be useful in the treatment of hyperglycemia (diabetes) and obesity in mammals, as well as in the treatment of gastrointestinal disorders and neurogenetic inflammation (U.S. Pat. No. 5,561,142). Additionally, they are known to lower triglyceride and cholesterol levels and to raise high-density lipoprotein levels in mammals (U.S. Pat. No. 5,451,677). Accordingly, they are useful in the treatment of conditions such as hypertriglyceridaemia, hypercholesterolaemia and in lowering high-density lipoprotein levels as well as in the treatment of atherosclerotic and cardiovascular diseases and related conditions. In addition, beta-3 adrenoreceptor agonists may also be useful in treating patients with impaired fasting glucose, impaired glucose tolerance, and type 2 diabetes.

Additionally, it is also believed that the compounds of this invention are effective in the treatment of ocular hypertension and glaucoma, and in the treatment of urological disorders including benign prostatic hyperplasia and incontinence, as well as in the treatment of prostate disease and as topical anti-inflammatory agents.

It has now been found that certain novel chroman derivatives are effective as beta-3 agonists and are useful in the treatment of beta-3 mediated conditions.

DESCRIPTION OF THE INVENTION

This invention relates to chroman compounds of Formula I wherein,

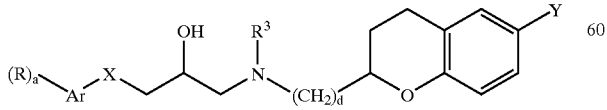

R is hydroxy, oxo, halo, cyano, nitro, $C_1$–$C_{10}$ alkyl optionally substituted with phenyl, $C_1$–$C_{10}$ haloalkyl, $CF_3$, $NR^1R^1$, $SR^1$, $OR^1$, $SO_2R^2$, $OCOR^2$, $NR^1COR^2$, $COR^2$, $NR^1SO_2R^2$, phenyl, or a 5- or 6-membered heterocycle with 1 to 4 heteroatoms selected independently from O, S, and N, each cyclic moiety being optionally substituted with hydroxy, $R^1$, halo, cyano, $NR^1R^1$, $SR^1$, $CF_3$, $OR^1$, $C_3$–$C_8$ cycloalkyl, $NR^1COR^2$, $COR^2$, $SO_2R^2$, $OCOR^2$, $NR^1SO_2R^2$, $C_1$–$C_{10}$ alkyl, or $C_1$–$C_{10}$ alkoxy;

$R^1$ is hydrogen, $(CH_2)_d$—O—$(CH_2)_dR^5$, where each d is selected independently, or $C_1$–$C_{10}$ alkyl optionally substituted with 1 to 4 substituents each independently selected from hydroxy, halo, $CO_2C_1$–$C_4$ alkyl, $CO_2H$, $S(O)_bC_1$–$C_{10}$ alkyl, $C_1$–$C_{10}$ alkoxy, and phenyl optionally substituted with $CO_2C_1$–$C_4$ alkyl or $CO_2H$, or $C_3$–$C_8$ cycloalkyl, phenyl, or naphthyl, each optionally substituted with 1 to 4 substituents each independently selected from halo, nitro, oxo, $C_1$–$C_{10}$ alkyl, $C_1$–$C_{10}$ alkoxy, and $C_1$–$C_{10}$ alkylthio; and when two $R^1$ groups are attached to N as $NR^1R^1$, these $R^1$ groups may form together with the nitrogen to which they are attached, a heterocyclic ring containing 4 to 7 C atoms, 1 to 2 N atoms, and 0 to 1 O or S atoms;

$R^2$ is $R^1$; $OR^1$; $NR^1R^1$; $NHS(O)_b$phenyl optionally substituted with $C_1$–$C_4$ alkyl, $C_1$–$C_4$ alkoxy, halo, or nitro; $NHS(O)_b$naphthyl; $NHS(O)_bC_1$–$C_{10}$ alkyl; or a 5- or 6-membered heterocycle with one or more heteroatoms selected independently from O, S, and N, said heterocyclic moiety being optionally substituted with $R^1$;

$R^3$ is hydrogen, $C_1$–$C_{10}$ alkyl, benzyl, or $COR^2$;

$R^4$ is hydrogen, $C_1$–$C_{10}$ alkyl, $C_1$–$C_{10}$ alkyl-phenyl, $C_1$–$C_{10}$ alkyl-pyridine;

$R^5$ is hydrogen or COOH;

Ar is phenyl optionally fused to a cyclohexyl, phenyl, or a 5- or 6-membered heterocycle containing one or more heteroatoms each independently selected from O, S, and N, said bicyclic moiety being optionally fused to phenyl, or a 5- or 6-membered heterocycle containing one or more heteroatoms each independently selected from N, S, and O, optionally fused to phenyl;

X is O or $S(O)_b$;

Y is halo, $R^1$, $OR^1SR^1$, $CO_2R^1$, $NR^1R^1$, $S(O)_b$-phenyl-$CO_2R^1$, or phenyl optionally fused to another phenyl ring or to a 5- or 6-membered heterocycle containing one or more heteroatoms each independently selected from N, S, and O, or a 5- or 6-membered heterocycle containing one or more heteroatoms each independently selected from N, S, and O, optionally fused to a phenyl ring, each cyclic moiety being optionally substituted with one or more substituents independently selected from $COR^2$; halo; $OR^1$; $NR^1R^1$; $R^1$; $C_1$–$C_{10}COR^2$; phenyl optionally substituted with halo, $C_1$–$C_4$ alkyl, or $C_1C_4$ alkoxy; tetrazolo; or

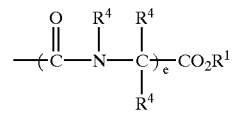

where, when the two $R^4$ groups attached to the same C are both alkyl, they optionally may be joined so that, when taken together with the C to which they are attached, they form a spiro ring of 3, 5, or 6 C atoms, or where the $R^4$ attached to N and one $R^4$ attached to the adjacent C are both alkyl, they optionally may be joined so that, taken together with the atoms to which they are attached, they form a 5- or 6-membered heterocycle;

a is 0, 1, 2, 3, 4, or 5;

b is 0, 1, or 2;

d is 1, 2, or 3;

e is 1 or 2;

and pharmaceutically acceptable salts and esters thereof.

The terms identified above have the following meaning throughout:

$C_1$–$C_{10}$ alkyl means straight or branched chain alkyl groups having from one to about ten carbon atoms, which may be saturated, unsaturated, or partially saturated. Such groups include methyl, ethyl, n-propyl, isopropyl, n-butyl, isobutyl, sec-butyl, tert-butyl, as well as vinyl, allyl, propynyl, butenyl, butadienyl, isopropenyl, methyleneyl, ethylenyl, propenyl, ethynyl, and the like.

$C_1$–$C_{10}$ haloalkyl means straight or branched chain alkyl groups having from one to about ten carbon atoms where any C—C bond may be saturated or unsaturated, the alkyl groups being substituted at any available carbon atom with one or more halogen atoms, and includes such groups as trifluoromethyl, trichloromethyl, pentafluoroethyl, fluoromethyl, 6-chlorohexyl, and the like.

The term $C_1$–$C_{10}$ alkoxy means straight or branched chain alkoxy groups having from one to about ten carbon atoms where any C—C bond may be saturated or unsaturated, and includes such groups as methoxy, ethoxy, n-propoxy, isopropoxy, n-butoxy, isobutoxy, sec-butoxy, tert-butoxy, and the like.

The term $C_1$–$C_{10}$ alkylthio means straight or branched chain alkylthio groups having from one to about ten carbon atoms where any C—C bond may be saturated or unsaturated, and includes such groups as methylthio, ethylthio, n-propylthio, isopropylthio, n-butylthio, isobutylthio, sec-butylthio, tert-butylthio, and the like.

$C_3$–$C_8$ cycloalkyl means saturated mono cyclic alkyl groups of from 3 to about 8 carbon atoms, and includes such groups as cyclopropyl, cyclopentyl, cyclohexyl, and the like.

Halo includes fluoro, chloro, bromo, and iodo, unless specifically stated otherwise.

$R^2$, Ar and Y each includes any 5- or 6-membered saturated or unsaturated heterocyclic group having any combination of one or more N, S, or O atoms, with the point of attachment being at any available position on the heterocyclic ring. Where there is more than one heteroatom in a single cyclic group, each heteroatom shall be chosen independently of any other heteroatom, in each occurrence. These moieties include such 5-membered heterocyclic groups as furyl, thienyl, pyrrolyl, oxazolyl, thiazolyl, imidazolyl, pyrazolyl, isoxazolyl, isothiazolyl, tetrahydrofuryl, dihydrofuryl, pyrrolidinyl, pyrrolinyl, dihydrothienyl, tetrahydrothienyl, dioxolyl, oxazolinyl, oxazolidinyl, isoxazolinyl, isoxazolidinyl, thiazolinyl, thiazolidinyl, isothiazolinyl, isothiazolidinyl, imidazolinyl, imidazolidinyl, pyrazolinyl, pyrazolidinyl, triazolyl, triazolinyl, triazolidinyl, oxadiazolyl, thiadiazolyl, furazanyl, tetrazolyl and the like. It also includes such 6-membered heterocyclic rings such as pyridyl, pyrimidinyl, pyrazinyl, pyridazinyl, pyranyl, dihydropyranyl, thiopyranyl, triazinyl, dioxanyl, piperidinyl, piperazinyl, pyrazinyl, morpholinyl, and the like.

Ar and Y also each includes phenyl fused to any 5- or 6-membered heterocyclic ring described above to form a bicyclic moiety, which may be saturated or unsaturated and may have any combination of one or more N, S, or O atoms, with the point of attachment being at any available position on the phenyl ring. These include such phenyl fused 5-membered heterocyclic groups as benzofuryl, dihydrobenzofuryl, benzothienyl, dihydrobenzothienyl, indolyl, indazolyl, indolinyl, indazolinyl, benzoxazolyl, benzoxazolinyl, benzothiazolyl, benzothiazolinyl, benzimidazolyl, benzimidazolinyl, benzisoxazolyl, benzisoxazolinyl, benzothiadiazolinyl, benzisothiazolyl, benzisothiazolinyl, benzotriazolyl, benzoxadiazolyl, benzoxadiazolinyl, benzothiadiazolyl, benzopyrazolinyl, and the like. It also includes such phenyl fused 6-membered heterocyclic groups as quinolyl, isoquinolyl, quinazolinyl, quinoxalinyl, cinnolinyl, chromenyl, phthalazinyl, dihydrobenzopyranyl, benzothiopyranyl, dihydrobenzothiopyranyl, benzoxazinyl, benzodioxanyl, benzodioxenyl, and the like.

Ar also includes phenyl fused to any 5- or 6-membered heterocyclic ring to form a bicyclic moiety as described above, which is further fused on the heterocyclic ring to a second phenyl ring, forming a tricyclic system, with the point of attachment to the core structure of the compound of Formula I being at any available position of the first phenyl ring. These include such groups as carbazolyl, carbazolinyl, acridinyl, xanthenyl, phenoxathiinyl, phenoxazinyl, phenanthridinyl, dibenzofuryl, dibenzopyranyl, dibenzodioxanoyl, phenazinyl, thianthrenyl, and the like.

Ar also includes any 5- or 6-membered saturated or unsaturated heterocyclic ring having any combination of one or more N, S, or O atoms, which is further fused to a phenyl ring, with the point of attachment to the core molecule of Formula I being at any available position on the heterocyclic ring. These include phenyl-fused with 5-membered hetero-bicyclic moieties such as benzofuryl, dihydrobenzofuryl, benzothienyl, dihydrobenzothienyl, indolyl, indazolyl, indolizinyl, indolinyl, indazolinyl, benzoxazolyl, benzoxazolinyl, benzothiazolyl, benzothiazolinyl, benzimidazolyl, benzimidazolinyl, benzisoxazolyl, benzisoxazolinyl, benzisothiazolyl, benzoisothiazolinyl, benzopyrazolinyl, and the like. It also includes phenyl-fused with 6-membered hetero-bicyclic groups such as quinolyl, isoquinolyl, quinazolinyl, quinoxalinyl, cinnolinyl, chromenyl, phthalazinyl, dihydrobenzopyranyl, benzothiopyranyl, dihydrobenzothiopyranyl, benzoxazinyl, benzodioxanyl, benzodioxenyl, and the like.

$C_1$–$C_{10}$-alkyl-phenyl means straight or branched chain saturated alkyl groups having from one to about ten carbon atoms where the phenyl moiety is attached at any available position on the alkyl group. Examples of these moieties include benzyl, 2-phenylethyl, 3-phenylpropyl, 2-phenylpropyl, 1-methyl-2-phenylethyl, 5-phenylpentyl, 4-phenylhexyl and the like.

$C_1$–$C_{10}$-alkyl-pyridyl means straight or branched chain saturated alkyl groups having from one to about ten carbon atoms where the pyridyl moiety is attached at any available position on the alkyl group. The pyridyl group may be attached to the alkyl group from any available position on the pyridine ring. Examples of these include pyridyl, 2-(2-pyridyl)ethyl, 3-(4-pyridyl)-propyl, 2-(3-pyridyl)-propyl, 1-methyl-2-(3-pyridyl)-ethyl, 5-(3-pyridyl)-pentyl, 4-(4-pyridyl)-hexyl, and the like.

$S(O)_b$-phenyl-$CO_2R^1$ means a phenylthio, a phenylsulfinyl or a phenylsulfonyl group, attached at any available position on the phenyl ring to a $CO_2R^1$ moiety.

When any moiety is described as being substituted, it may have one or more of the indicated substituents that may be located at any available position on the moiety. When there are two or more substituents on any moiety, each term shall be defined independently of any other in each occurrence. For example, $NR^1R^1$ may represent $NH_2$, $NHCH_3$, $N(CH_3)$ $CH_2CH_2CH_3$, and the like; or for example, $Ar(R)_a$, where a=3, Ar may be substituted by three (3) different substituents such as hydroxy, halo, and alkyl, and the like.

Illustrative examples of the compounds of Formula I in this invention include but are not limited to those summarized in Table 1 below:

TABLE 1
Illustrative Examples of the Invention
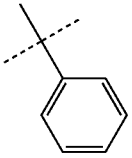
(I)
| Entry No. | R | a | Ar | R³ | X | d | Y |
|---|---|---|---|---|---|---|---|
| 1 | — | 0 | 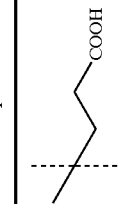 | H | O | 1 | 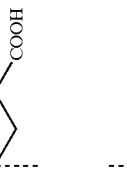 |
| 2 | 3-CONH-i-Bu | 1 | 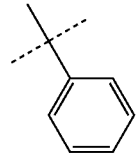 | H | O | 1 | 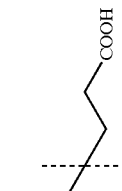 |
| 3 | 2,4-diMe-6-Cl | 3 | 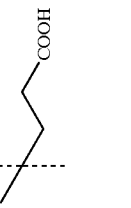 | H | O | 1 | 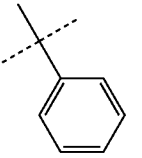 |
| 4 | 2,3,5,6-tetra-Cl | 4 | 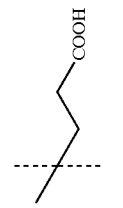 | H | O | 1 | 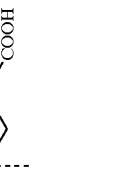 |
| 5 | 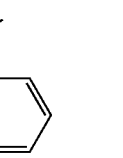 | 1 | 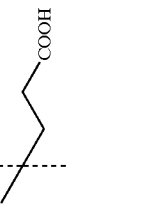 | H | O | 1 |  |

TABLE 1-continued
Illustrative Examples of the Invention
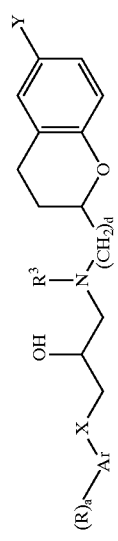
(I)
| Entry No. | R | a | Ar | R³ | X | d | Y |
|---|---|---|---|---|---|---|---|
| 6 | 2-Cl | 1 | phenyl | H | O | 1 | –C(CH₃)₂CH₂COOH |
| 7 | — | 0 | phenyl | H | O | 1 | 4-COOH-phenyl |
| 8 | — | 0 | phenyl | COO-t-Bu | O | 1 | 4-COOH-phenyl |
| 9 | — | 0 | phenyl | COO-t-Bu | S | 1 | 4-COOH-phenyl |
| 10 | — | 0 | phenyl | H | O | 2 | 4-COOH-phenyl |

TABLE 1-continued
Illustrative Examples of the Invention
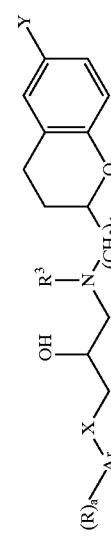
(I)
| Entry No. | R | a | Ar | R³ | X | d | Y |
|---|---|---|---|---|---|---|---|
| 11 | — | 0 | phenyl | H | O | 3 | 4-COOH-phenyl |
| 12 | — | 0 | phenyl | H | S | 1 | 4-COOH-phenyl |
| 13 | — | 0 | phenyl | COOMe | O | 1 | 4-COOH-phenyl |
| 14 | — | 0 | phenyl | CONH₂ | O | 1 | 4-COOH-phenyl |
| 15 | — | 0 | phenyl | COMe | O | 1 | 4-COOH-phenyl |

TABLE 1-continued
Illustrative Examples of the Invention
(I)
| Entry No. | R | a | Ar | R³ | X | d | Y |
|---|---|---|---|---|---|---|---|
| 16 | — | 0 | phenyl | COOMe | S | 1 | 4-COOH-phenyl |
| 17 | — | 0 | phenyl | H | SO | 1 | 4-COOH-phenyl |
| 18 | — | 0 | phenyl | H | SO₂ | 1 | 4-COOH-phenyl |
| 19 | — | 0 | phenyl | H | O | 1 | 3-COOH-phenyl |
| 20 | — | 0 | phenyl | H | O | 2 | 3-COOH-phenyl |

TABLE 1-continued

Illustrative Examples of the Invention

| Entry No. | R | a | Ar | R³ | X | d | Y |
|---|---|---|---|---|---|---|---|
| 21 | — | 0 | phenyl | H | S | 1 | 3-COOH-phenyl |
| 22 | — | 0 | phenyl | H | S | 2 | 3-COOH-phenyl |
| 23 | — | 0 | phenyl | H | SO₂ | 1 | 3-COOH-phenyl |
| 24 | — | 0 | phenyl | H | SO | 1 | 3-COOH-phenyl |
| 25 | — | 0 | phenyl | H | SO₂ | 2 | 3-COOH-phenyl |

TABLE 1-continued

Illustrative Examples of the Invention $$(R)_a\text{—Ar—X}\overset{\text{OH}}{\underset{}{\text{—}}}\overset{R^3}{\underset{}{\text{N—}(CH_2)_d}}\text{—[chroman-Y]}$$

(I)

| Entry No. | R | a | Ar | R³ | X | d | Y |
|---|---|---|---|---|---|---|---|
| 26 | — | 0 | phenyl | H | SO | 2 | 3-COOH-phenyl |
| 27 | 3-CF₃ | 1 | phenyl | H | S | 1 | 4-COOMe-phenyl |
| 28 | 4-MeO | 1 | phenyl | H | S | 1 | 4-COOH-phenyl |
| 29 | 3-i-Pr | 1 | phenyl | H | O | 1 | 4-COOH-phenyl |
| 30 | 2-F-6-MeO | 2 | phenyl | H | O | 1 | 4-COOH-phenyl |

TABLE 1-continued
Illustrative Examples of the Invention
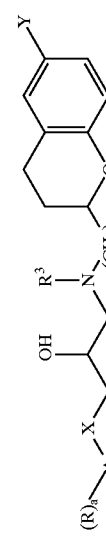
(I)
| Entry No. | R | a | Ar | R³ | X | d | Y |
|---|---|---|---|---|---|---|---|
| 31 | 2-Ph | 1 | phenyl | H | O | 1 | 4-COOH-phenyl |
| 32 | 2-CN | 1 | 7-indolyl | H | O | 1 | gem-dimethyl-COOH |
| 33 | H | 0 | carbazolyl | H | O | 1 | 4-COOH-phenyl |
| 34 | — | 0 | carbazolyl | H | S | 1 | 4-COOH-phenyl |

TABLE 1-continued

Illustrative Examples of the Invention

| Entry No. | R | a | Ar | R³ | X | d | Y |
|---|---|---|---|---|---|---|---|
| 35 | — | 0 | carbazol-1-yl | Et | O | 1 | 4-COOH-phenyl |
| 36 | — | 0 | carbazol-1-yl | H | O | 2 | 4-COOH-phenyl |
| 37 | — | 0 | carbazol-1-yl | H | O | 3 | 4-COOH-phenyl |
| 38 | 2-Me | 1 | quinolin-8-yl | H | O | 1 | 4-COOMe-phenyl |

TABLE 1-continued

Illustrative Examples of the Invention

| Entry No. | R | a | Ar | R³ | X | d | Y |
|---|---|---|---|---|---|---|---|
| 39 | — | 0 | benzothiophen-4-yl | H | O | 1 | 4-(COOMe)phenyl |
| 40 | — | 0 | pyridin-3-yl | H | O | 1 | 4-(COOH)phenyl |
| 41 | — | 0 | isoquinolin-3-yl | H | O | 1 | 4-(COOH)phenyl |
| 42 | — | 0 | benzothiophen-3-yl | H | O | 1 | 4-(COOH)phenyl |
| 43 | — | 0 | benzimidazol-2-yl | H | O | 1 | 4-(COOH)phenyl |

TABLE 1-continued

Illustrative Examples of the Invention (I) structure: (R)ₐ—Ar—X—CH(OH)—CH₂—N(R³)—(CH₂)_d—[chroman with Y substituent]

| Entry No. | R | a | Ar | R³ | X | d | Y |
|---|---|---|---|---|---|---|---|
| 44 | — | 0 | phenyl | H | O | 3 | 3-carboxyphenyl |
| 45 | — | 0 | phenyl | H | O | 1 | 6-carboxy-2-naphthyl |
| 46 | — | 0 | phenyl | H | O | 1 | 5-carboxy-2,3-dihydrobenzofuran-6-yl |
| 47 | — | 0 | phenyl | H | O | 1 | 2-carboxy-8-quinolinyl |

TABLE 1-continued

Illustrative Examples of the Invention (I)

| Entry No. | R | a | Ar | R³ | X | d | Y |
|---|---|---|---|---|---|---|---|
| 48 | — | 0 | phenyl | H | O | 1 | 2-nitro-4-methylphenyl |
| 49 | — | 0 | phenyl | H | O | 1 | 1,5-dimethyl-4-(t-butyl)-pyrazole-3-COOH |
| 50 | — | 0 | phenyl | H | S | 1 | 1,5-dimethyl-4-(t-butyl)-pyrazole-3-COOH |
| 51 | — | 0 | phenyl | H | O | 1 | 1,5-dimethyl-4-(t-butyl)-pyrazole-3-COOH |

TABLE 1-continued
Illustrative Examples of the Invention
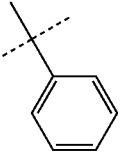
| Entry No. | R | a | Ar | R³ | X | d | Y |
|---|---|---|---|---|---|---|---|
| 52 | — | 0 | 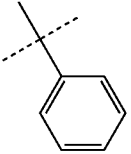 | H | O | 1 | 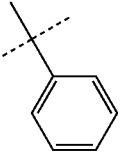 |
| 53 | — | 0 | 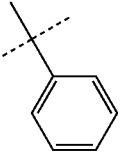 | H | O | 1 | 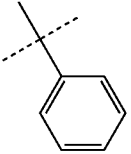 |
| 54 | — | 0 | 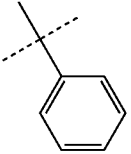 | H | O | 1 | 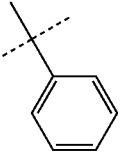 |
| 55 | — | 0 | 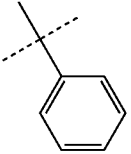 | H | O | 1 |  |

TABLE 1-continued
Illustrative Examples of the Invention
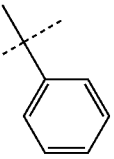
| Entry No. | R | a | Ar | R³ | X | d | Y |
|---|---|---|---|---|---|---|---|
| 56 | — | 0 | 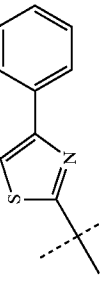 | H | O | 1 | 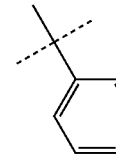 |
| 57 | — | 0 | 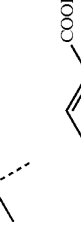 | H | O | 1 | 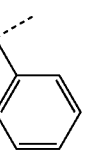 |
| 58 | 4-MeS | 1 | 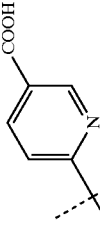 | H | O | 1 |  |
| 59 | 4-OH | 1 | 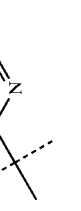 | H | O | 1 |  |
| 60 | 3-NO₂ | 0 |  | H | O | 1 | |

TABLE 1-continued

Illustrative Examples of the Invention (I)

| Entry No. | R | a | Ar | R³ | X | d | Y |
|---|---|---|---|---|---|---|---|
| 61 | — | 0 | phenyl | H | O | 1 | 2-methyl-benzothiophene-5-COOH |
| 62 | — | 0 | phenyl | H | O | 1 | 1-methyl-2-COOH-indol-3-yl |
| 63 | — | 0 | phenyl | H | O | 1 | 2-methyl-benzofuran-5-COOH |
| 64 | — | 0 | phenyl | H | O | 1 | -C(Me)₂-C(O)-N(Me)-CH₂-COOH |
| 65 | — | 0 | phenyl | H | O | 1 | -C(Me)₂-C(O)-NH-CH₂-COOH |

TABLE 1-continued
Illustrative Examples of the Invention
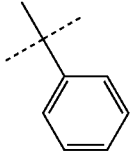
| Entry No. | R | a | Ar | R³ | X | d | Y |
|---|---|---|---|---|---|---|---|
| 66 | — | 0 | 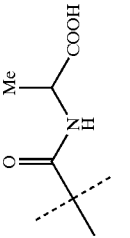 | H | O | 1 | 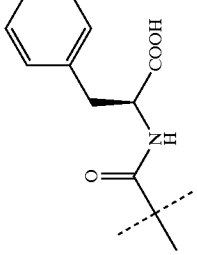 |
| 67 | — | 0 | 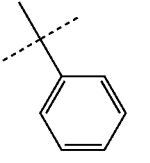 | H | O | 1 | 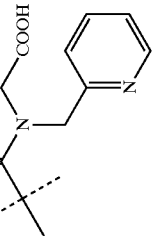 |
| 68 | — | 0 | 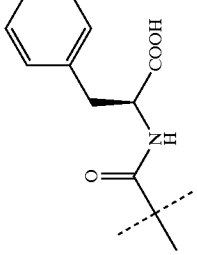 | H | O | 1 | 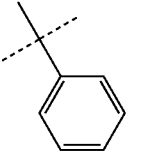 |

TABLE 1-continued

Illustrative Examples of the Invention

| Entry No. | R | a | Ar | R³ | X | d | Y |
|---|---|---|---|---|---|---|---|
| 69 | — | 0 | phenyl | H | O | 1 | N-Me, CH2Ph, COOH |
| 70 | — | 0 | phenyl | H | O | 1 | 1-(cyclopropyl)-NH-COOH |
| 71 | — | 0 | phenyl | H | O | 1 | 1-(cyclopentyl)-NH-COOH |
| 72 | — | 0 | phenyl | H | O | 1 | 1-(cyclohexyl)-NH-COOH |

TABLE 1-continued
Illustrative Examples of the Invention
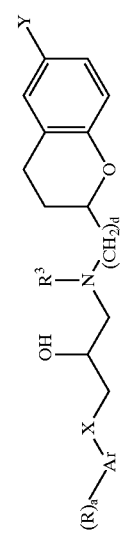
(I)
| Entry No. | R | a | Ar | R³ | X | d | Y |
|---|---|---|---|---|---|---|---|
| 73 | — | 0 | phenyl | H | O | 1 | pyrrolidine-N-acyl-2-COOH (pivaloyl linker) |
| 74 | — | 0 | phenyl | H | O | 1 | piperidine-N-acyl-2-COOH (pivaloyl linker) |
| 75 | — | 0 | phenyl | H | O | 1 | Me-CH(NHC(O)tBu)-C(O)NH-CH2-COOH |
| 76 | — | 0 | phenyl | H | O | 1 | PhCH2-CH(NHC(O)tBu)-C(O)NH-CH(iPr)-COOH |

TABLE 1-continued

Illustrative Examples of the Invention

| Entry No. | R | a | Ar | R³ | X | d | Y |
|---|---|---|---|---|---|---|---|
| 77 | — | 0 | phenyl | H | O | 1 | pivaloyl-N(Me)-CH₂-C(=O)-NH-(1-cyclopropyl-COOH) |
| 78 | — | 0 | phenyl | H | O | 1 | H |
| 79 | — | 0 | phenyl | H | O | 1 | I |
| 80 | — | 0 | phenyl | H | O | 1 | -CH₂-(4-COOH-phenyl) |
| 81 | — | 0 | phenyl | H | | | N(Me)₂ |

TABLE 1-continued

Illustrative Examples of the Invention

![Structure of formula (I): (R)_a—Ar—X—CH2—CH(OH)—CH2—N(R³)—(CH2)_d—chroman-2-yl with Y substituent on chroman ring]

(I)

| Entry No. | R | a | Ar | R³ | X | d | Y |
|---|---|---|---|---|---|---|---|
| 82 | — | 0 | phenyl | H | O | 1 | piperazin-1-yl (N-NH) |
| 83 | — | 0 | phenyl | H | O | 1 | Br |
| 84 | — | 0 | phenyl | H | O | 1 | —COOH |
| 85 | — | 0 | phenyl | H | O | 2 | —COOH |
| 86 | — | 0 | phenyl | H | S | 1 | —COOH |

TABLE 1-continued
Illustrative Examples of the Invention
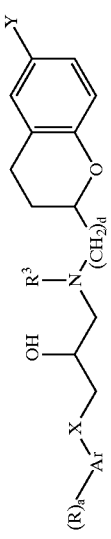
| Entry No. | R | a | Ar | R³ | X | d | Y |
|---|---|---|---|---|---|---|---|
| 87 | — | 0 | phenyl | H | O | 1 | CH=CH-C(CH₃)₂-COOH |
| 88 | — | 0 | phenyl | H | O | 1 | S-C(CH₃)₂-COOH |
| 89 | — | 0 | phenyl | H | O | 1 | C(CH₃)₂-S-(m-C₆H₄)-COOH |
| 90 | — | 0 | phenyl | H | O | 1 | C(CH₃)₂-CH(SMe)-COOH |
| 91 | — | 0 | phenyl | H | O | 1 | C≡C-C(CH₃)₂-OH |

TABLE 1-continued
Illustrative Examples of the Invention
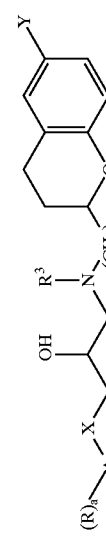
(I)
| Entry No. | R | a | Ar | R³ | X | d | Y |
|---|---|---|---|---|---|---|---|
| 92 | — | 0 | phenyl | H | O | 1 | -O-CH2-COOMe |
| 93 | — | 0 | phenyl | H | O | 1 | -O-CH2-C(Me)2-COOH |
| 94 | — | 0 | phenyl | H | O | 1 | -(CH2)5-COOH |
| 95 | — | 0 | phenyl | H | O | 1 | -(CH2)2-C(Me)2-COOH |
| 96 | — | 0 | phenyl | H | | | -Et |

TABLE 1-continued
Illustrative Examples of the Invention
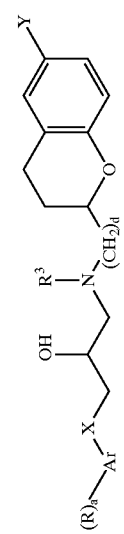
(I)
| Entry No. | R | a | Ar | R³ | X | d | Y |
|---|---|---|---|---|---|---|---|
| 97 | — | 0 | 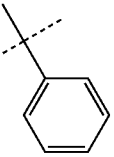 | H | O | 1 | —CF₃ |
| 98 | — | 0 | 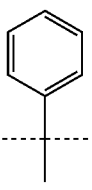 | H | O | 1 | -t-Bu |
| 99 | — | 0 | 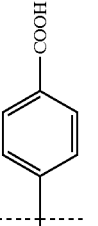 | H | O | 1 | 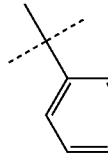 |
| 100 | 6-NH₂ | 1 | 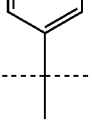 | H | O | 1 | 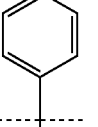 |
| 101 | 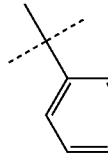 | 1 | 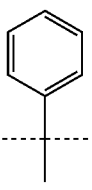 | H | O | 1 | 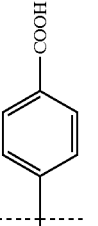 |

TABLE 1-continued

Illustrative Examples of the Invention (I)

| Entry No. | R | a | Ar | R³ | X | d | Y |
|---|---|---|---|---|---|---|---|
| 102 | 2,3,4,5,6-penta-F | 5 | phenyl | H | O | 1 | 4-COOH-phenyl |
| 103 | — | 0 | phenyl | Me | O | 1 | 2-tBu-4-phenyl-thiazol-5-yl-COOH |
| 104 | — | 0 | phenyl | Me | O | 2 | 2-tBu-4-phenyl-thiazol-5-yl-COOH |
| 105 | — | 0 | phenyl | Et | S | 1 | 2-tBu-4-phenyl-thiazol-5-yl-COOH |

TABLE 1-continued
Illustrative Examples of the Invention
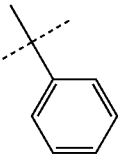
(I)
| Entry No. | R | a | Ar | R³ | X | d | Y |
|---|---|---|---|---|---|---|---|
| 106 | — | 0 | 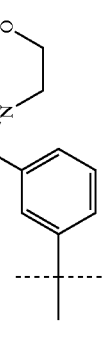 | H | O | 1 | 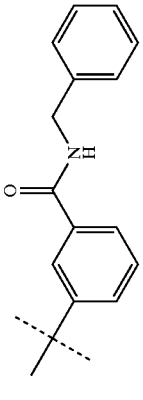 |
| 107 | — | 0 | 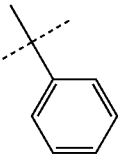 | H | O | 1 | 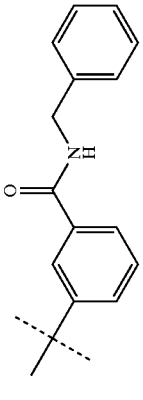 |
| 108 | — | 0 | 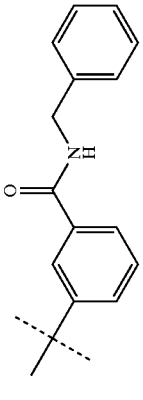 | H | O | 1 | 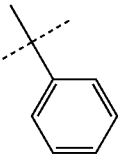 |
| 109 | — | 0 | 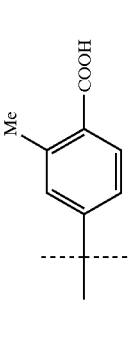 | H | O | 1 | 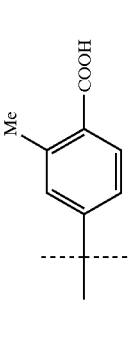 |
| 110 | — | 0 | 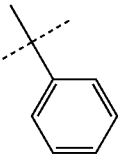 | H | O | 1 | 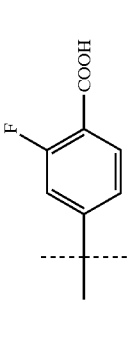 |

TABLE 1-continued
Illustrative Examples of the Invention
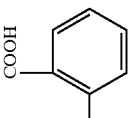
(I)
| Entry No. | R | a | Ar | R³ | X | d | Y |
|---|---|---|---|---|---|---|---|
| 111 | — | 0 | phenyl | H | O | 1 | 2-COOH-phenyl |
| 112 | — | 0 | phenyl | H | O | 1 | 2-(tetrazol-5-yl)phenyl |
| 113 | — | 0 | phenyl | H | O | 1 | 4-(tetrazol-5-yl)phenyl |
| 114 | — | 0 | phenyl | pyrrolidinyl-C(O)- | O | 1 | 4-COOH-phenyl |
| 115 | — | 0 | phenyl | piperidinyl-C(O)- | O | 1 | 4-COOH-phenyl |

TABLE 1-continued

Illustrative Examples of the Invention

| Entry No. | R | a | Ar | R³ | X | d | Y |
|---|---|---|---|---|---|---|---|
| 116 | — | 0 | phenyl | morpholine-C(=O)- | O | 1 | 4-COOH-phenyl |
| 117 | — | 0 | phenyl | thiomorpholine-C(=O)- | O | 1 | 4-COOH-phenyl |
| 118 | — | 0 | phenyl | phenyl-C(=O)- | O | 1 | 4-COOH-phenyl |
| 119 | — | 0 | phenyl | furan-2-yl-C(=O)- | O | 1 | 4-COOH-phenyl |
| 120 | — | 0 | phenyl | thiophen-2-yl-C(=O)- | O | 1 | 4-COOH-phenyl |

TABLE 1-continued

Illustrative Examples of the Invention (I)

| Entry No. | R | a | Ar | R³ | X | d | Y |
|---|---|---|---|---|---|---|---|
| 121 | — | 0 | phenyl | CH₂-phenyl | O | 1 | 4-COOMe-phenyl |
| 122 | — | 0 | phenyl | CH₂-phenyl | O | 1 | 4-COOH-phenyl |
| 123 | — | 0 | phenyl | CH₂-phenyl | O | 2 | 4-COOH-phenyl |
| 124 | — | 0 | phenyl | CH₂-phenyl | S | 1 | 4-COOH-phenyl |
| 125 | — | 0 | phenyl | CH₂-phenyl | O | 1 | pyridyl-CONH₂ |

TABLE 1-continued

Illustrative Examples of the Invention (structure I: (R)_a—Ar—X—CH2—CH(OH)—CH2—N(R^3)—(CH2)_d—[chroman with Y at 6-position])

| Entry No. | R | a | Ar | R³ | X | d | Y |
|---|---|---|---|---|---|---|---|
| 126 | — | 0 | phenyl | H | O | 1 | 4-(pyridin-2-yl-carboxamide), t-Bu-substituted |
| 127 | — | 0 | phenyl | H | S | 1 | 4-(pyridin-2-yl-carboxamide), t-Bu-substituted |
| 128 | — | 0 | phenyl | H | O | 2 | 4-(pyridin-2-yl-carboxamide), t-Bu-substituted |
| 129 | — | 0 | phenyl | H | O | 1 | 3-(CONHSO$_2$Ph)phenyl, t-Bu-substituted |
| 130 | — | 0 | phenyl | H | O | 1 | 3-(CONHSO$_2$Me)phenyl, t-Bu-substituted |

TABLE 1-continued

Illustrative Examples of the Invention

| Entry No. | R | a | Ar | R³ | X | d | Y |
|---|---|---|---|---|---|---|---|
| 131 | — | 0 | phenyl | H | O | 1 | 4-(CONHSO₂Ph)phenyl |
| 132 | — | 0 | phenyl | CH₂-phenyl | O | 1 | Br |
| 133 | — | 0 | 2-naphthyl | H | O | 1 | 4-COOH-phenyl |
| 134 | 2-EtO-5-(1-propenyl)- | 2 | phenyl | H | O | 1 | 4-COOH-phenyl |
| 135 | 2-(2-propenyl)-4-Cl | 2 | phenyl | H | O | 1 | 4-COOH-phenyl |

TABLE 1-continued
Illustrative Examples of the Invention
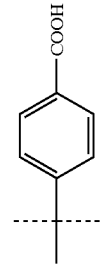
(I)
| Entry No. | R | a | Ar | R³ | X | d | Y |
|---|---|---|---|---|---|---|---|
| 136 | — | 0 | tetrahydronaphthyl | H | O | 1 | 4-COOH-phenyl |
| 137 | 2-(1-Ph)-Et-4-Cl | 2 | phenyl | H | O | 1 | 4-COOH-phenyl |
| 138 | 1-pyrrolyl- | 1 | phenyl | H | O | 1 | 4-COOH-phenyl |
| 139 | 2-AcNH— | 1 | phenyl | H | O | 1 | 4-COOH-phenyl |
| 140 | 2-i-Pr-5-Me- | 2 | phenyl | H | O | 1 | 4-COOH-phenyl |

TABLE 1-continued
Illustrative Examples of the Invention
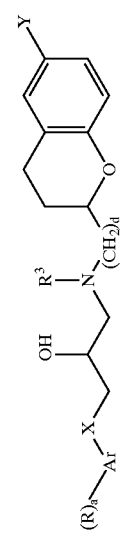
(I)
| Entry No. | R | a | Ar | R³ | X | d | Y |
|---|---|---|---|---|---|---|---|
| 141 | 2-PhC(=O)— | 1 | Ph | H | O | 1 | 4-COOH-phenyl |
| 142 | 4-Br | 1 | Ph | H | O | 1 | 4-COOH-phenyl |
| 143 | — | 0 | Ph | H | O | 1 | 2-COOH-5-NH₂-phenyl |
| 144 | — | 0 | Ph | H | O | 1 | 2-COOH-5-NEt₂-phenyl |

TABLE 1-continued
Illustrative Examples of the Invention
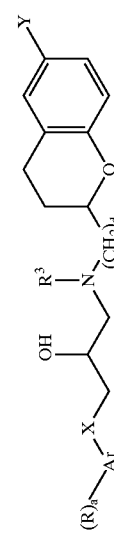
(I)
| Entry No. | R | a | Ar | R³ | X | d | Y |
|---|---|---|---|---|---|---|---|
| 145 | — | 0 | phenyl | H | O | 1 | 2-COOH-5-(NHcyclohexyl)phenyl |
| 146 | — | 0 | phenyl | H | O | 1 | 2-COOH-5-(NHCH2CH2OCH3)phenyl |
| 147 | — | 0 | phenyl | H | O | 1 | 2-COOH-5-(NHcyclobutyl)phenyl |
| 148 | — | 0 | phenyl | H | O | 1 | 2-COOH-5-(piperidinyl)phenyl |

TABLE 1-continued

Illustrative Examples of the Invention

| Entry No. | R | a | Ar | R³ | X | d | Y |
|---|---|---|---|---|---|---|---|
| 149 | — | 0 | phenyl | H | O | 1 | N-cyclohexyl 4-tert-butyl pyridine-2-carboxamide |
| 150 | — | 0 | phenyl | H | O | 1 | N-(4-fluorobenzyl) 4-tert-butyl pyridine-2-carboxamide |
| 151 | 2-EtO-5-(1-propenyl)- | 2 | phenyl | H | O | 1 | 4-tert-butyl pyridine-2-carboxamide |
| 152 | — | 0 | phenyl | H | O | 1 | 4'-chloro-5-methyl biphenyl-2-carboxylic acid |

TABLE 1-continued
Illustrative Examples of the Invention
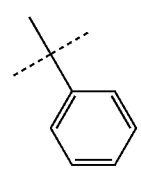
(I)
| Entry No. | R | a | Ar | R³ | X | d | Y |
|---|---|---|---|---|---|---|---|
| 153 | — | 0 | 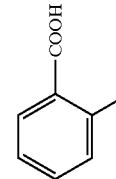 | H | O | 1 | 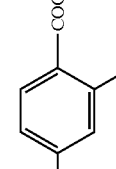 |
| 154 | — | 0 | 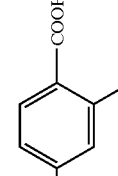 | H | O | 1 | 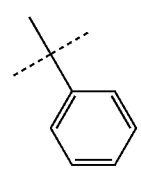 |
| 155 | — | 0 | 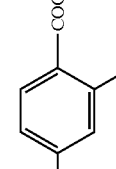 | H | O | 1 | 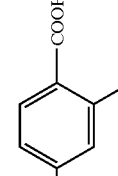 |

TABLE 1-continued
Illustrative Examples of the Invention
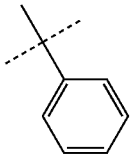
| Entry No. | R | a | Ar | R³ | X | d | Y |
|---|---|---|---|---|---|---|---|
| 156 | — | 0 | 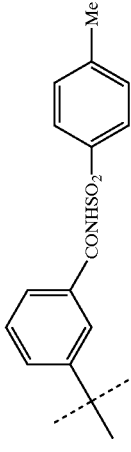 | H | O | 1 | 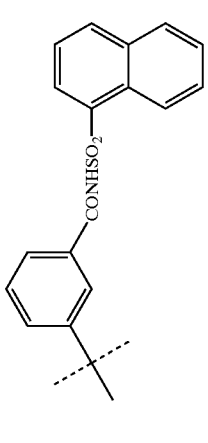 |
| 157 | — | 0 | 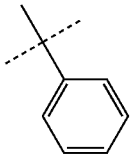 | H | O | 1 | 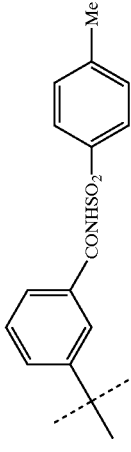 |
| 158 | — | 0 | 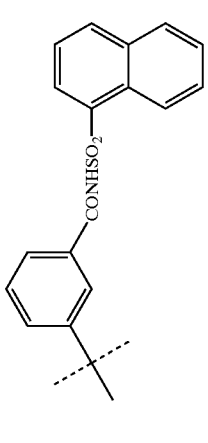 | H | O | 1 |  |

TABLE 1-continued
Illustrative Examples of the Invention
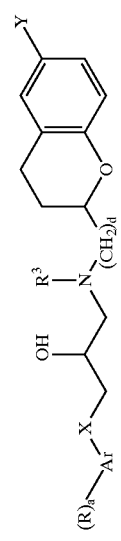
(I)
| Entry No. | R | a | Ar | R³ | X | d | Y |
|---|---|---|---|---|---|---|---|
| 159 | — | 0 | *t-Bu-phenyl* | H | O | 1 | *3-NO₂, 3-t-Bu-biphenyl-CONHSO₂* |
| 160 | — | 0 | *t-Bu-phenyl* | H | O | 1 | *4-OMe, 3-t-Bu-biphenyl-CONHSO₂* |
| 161 | — | 0 | *t-Bu-phenyl* | H | O | 1 | *3-Br, 3-t-Bu-biphenyl-CONHSO₂* |

As is true of most classes of therapeutically effective compounds, certain subclasses and certain species which are particularly effective are preferred over others. For example, one preferred set of compounds of Formula I are those wherein X is O or S; and Y is $R^1$, phenyl or a 5- or 6-membered heterocycle containing one or more heteroatoms each independently selected from N, S, and O, each cyclic moiety being optionally substituted with one or more substituents selected from $COR^2$, halo, or $C_1$–$C_{10}$ alkyl.

A more preferred set of compounds of Formula I are those wherein a is 0, 1, or 2; Ar is phenyl, a 5- or 6-membered heterocycle containing one heteroatom, phenyl fused to a 5- or 6-membered heterocycle, or carbanzolyl or carbanzolinyl; X is O; $R^3$ is hydrogen; d is 1; Y is phenyl substituted with $COR^2$; and $R^2$ is $OR^1$.

Representative salts of the compounds of Formula I include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include, for example, alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates such as dimethyl, diethyl, and dibutyl sulfate; and diamyl sulfates, long chain halides such as decyl, lauryl, myristyl and strearyl chlorides, bromides and iodides, aralkyl halides such as benzyl and phenethyl bromides and others.

The esters in the present invention are non-toxic, pharmaceutically acceptable esters such as alkyl esters, for example methyl, ethyl, propyl, isopropyl, butyl, isobutyl, or pentyl esters. Additional esters such as phenyl-$C_1$–$C_5$ alkyl may be used, although methyl ester is preferred. The compound of Formula I may be esterified by a variety of conventional procedures including reacting the appropriate anhydride, carboxylic acid, or acid chloride with the alcohol group of the Formula I compound. The appropriate anhydride is reacted with the alcohol in the presence of an acylation catalyst such as 1,8-bis[dimethylamino]naphthalene or N,N-dimethylaminopyridine. An appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water and, optionally, an acylation catalyst. Esterification can also be reached using the appropriate carboxylic acid in the presence of trifluoroacetic anhydride and, optionally, pyridine, or in the presence of N,N-carbonyldiimidazole with pyridine. Reaction of an acid chloride with the alcohol is carried out with an acylation catalyst such as 4-DMAP or pyridine.

Sensitive or reactive groups on the compound of Formula I may need to be protected during any of the above methods for forming esters, and protecting groups may be added and removed by conventional methods well known in the art.

One skilled in the art would readily know how to successfully carry out these as well as other methods of esterification of alcohols.

The compounds of this invention may, either by nature of asymmetric centers or by restricted rotation, be present in the form of isomers. Any isomer may be present in the (R)-, (S)-, or (R,S) configuration, preferably in the (R)- or (S)-configuration, whichever is most active. The configurational isomers of Formula I, in which both 1. the hydroxyl group attached to the side chain containing the Ar—X— moiety and
2. the $(CH_2)_d$ group attached to the dihydrochromenyl ring are above the plane as depicted below

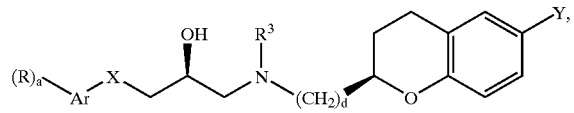

are preferred.

All isomers of the compounds of this invention, whether separated, pure, partially pure, or in a diastereomeric or racemic mixture, are encompassed within the scope of this invention. The purification of said isomers and the separation of said isomeric mixtures can be accomplished by standard techniques known in the art.

Geometric isomers by nature of substituents about a double bond or a ring may be present in cis (═Z—) or trans (═E—) form, and are each encompassed within the scope of this invention.

The particular process to be utilized in the preparation of the compounds of this invention depends upon the specific compound desired. Such factors as the selection of the specific Ar, X, and Y moieties, and the specific substituents on the various moieties, all play a role in the path to be followed in the preparation of the specific compounds of this invention. These factors are readily recognized by one of ordinary skill in the art.

For synthesis of any particular compound, one skilled in the art will recognize that the use of protecting groups may be required for the synthesis of compounds containing certain substituents. A description of suitable protecting groups and appropriate methods of removing such groups may be found in: *Protective Groups in Organic Synthesis*, Second Edition, T. W. Greene, John Wiley and Sons, New York, 1991. For example, after preparation of a compound according to Reaction Scheme 1, in order to enable purification of the end product by, for instance, flash chromatography, compounds of Formula I wherein $R^3$ is H, can be selectively protected, for example, as a carbamate derivative obtained by, for example, treatment with a reagent such as di-tert-butyl dicarbonate or other means known in the art. After purification, the carbamate group can easily be removed by treatment with an acid such as HCl or trifluoroacetic acid by methods known in the art.

In the Reaction Schemes below, one skilled in the art will recognize that reagents and solvents actually used may be selected from several reagents and solvents well known in the art to be effective equivalents. When specific reagents or solvents are shown in a Reaction Scheme, therefore, they are meant to be illustrative examples of specific but not limiting conditions for the execution of that particular Reaction Scheme.

General Methods of Preparation of Formula I Compounds

In general, Formula I compounds may be prepared by standard techniques known in the art and by known processes analogous thereto. In particular, three such standard methods may be used, the selection of which may be based, among other considerations, upon the commercial availability of the required individual starting materials. These three methods are illustrated in Reaction Schemes 1, 2, and 3 below.

The compounds of Formula I where each variable may be any moiety within that variable's definition may be synthesized according to Reaction Scheme 1 by coupling an appropriate epoxide 1 with an appropriate amine 2 where $R^3$ is hydrogen or alkyl. The epoxide 1 is either commercially available, known in the art, or for Formula I compounds where X is O or S, may be readily prepared from known hydroxy or thiol compounds as exemplified in Reaction Scheme 10. Formula I compounds in which X is SO or $S(O)_2$ may be generally prepared from other Formula I compounds where X is S by oxidation with reagents such as Oxone® or mCPBA. Preparation of 2 is described in Reaction Schemes 15, 16, 17, 20, 21, and 22 below. The reaction of Reaction Scheme 1 is typically carried out in an aprotic solvent such as dimethyl sulfoxide, dimethyl formamide, acetonitrile, or in an alcohol such as ethanol, isopropanol, or propanol at a temperature of from about –10° C. to reflux. Compounds in which $R^3$ is other than hydrogen may be prepared by reaction of compound I in which $R^3$ is H, by selective N-alkylation or N-acylation reactions with known compounds of formula $R^3$-halo (where $R^3$ is alkyl, benzyl, or acyl; or $[R^3]_2O$ where $R^3$ is acyl). Protection of the hydroxyl group, for example as a Cbz ester, may be required prior to N-alkylation reactions; O-deprotection is carried out under standard conditions well known in the art.

REACTION SCHEME 1

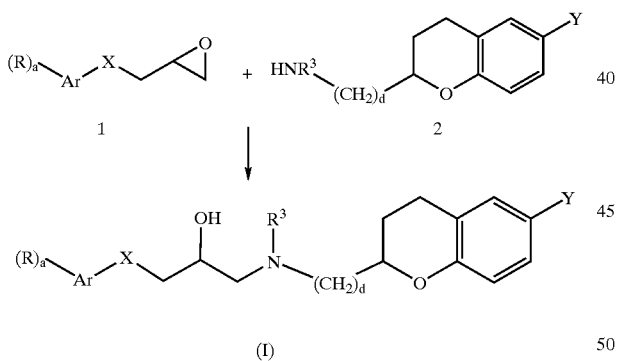

Alternatively, Formula I compounds, where each variable may be any moiety within that particular variable definition except that d=1 may be prepared by a reductive amination as shown in Reaction Scheme 2, involving reaction of an aldehyde of Formula 4 (preparation described below in Reaction Scheme 11) with an amino alcohol of Formula 3 (preparation described below in Reaction Scheme 10). Compounds in which $R^3$ is other than hydrogen may be prepared by reaction of compound Ia in which $R^3$ is H, by selective N-alkylation or N-acylation reactions with known compounds of formula $R^3$-halo (where $R^3$ is alkyl, benzyl, or acyl; or $[R^3]_2O$ where $R^3$ is acyl). Protection of the hydroxyl group, for example as a Cbz ester, may be required prior to N-alkylation reactions; O-deprotection is carried out under standard conditions well known in the art.

REACTION SCHEME 2

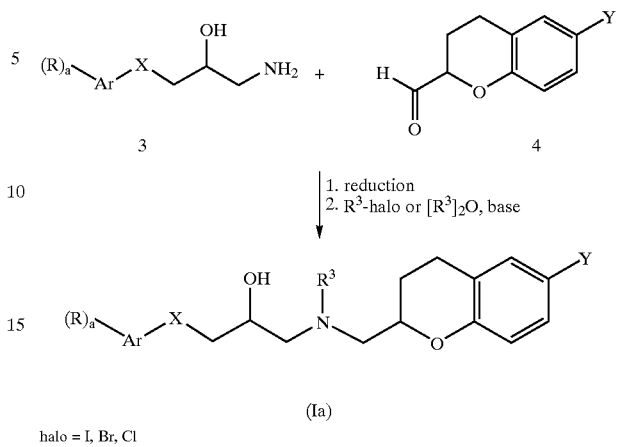

A third general route to Formula I compounds, where each variable may be any moiety within that particular variable definition except that d=1 is shown in Reaction Scheme 3, in which an amino alcohol 3 and a carboxylic acid 5 (preparation described in Reaction Schemes 12 and 13) are coupled to provide an amide of Formula 6. Reduction of the Formula 6 amides with an appropriate reagent such as borane-dimethylsulfide complex provides the Formula I compounds where $R^3$ is H. Formula I compounds in which $R^3$ is other than H may be similarly prepared as described above for Reaction Schemes 1 and 2.

REACTION SCHEME 3

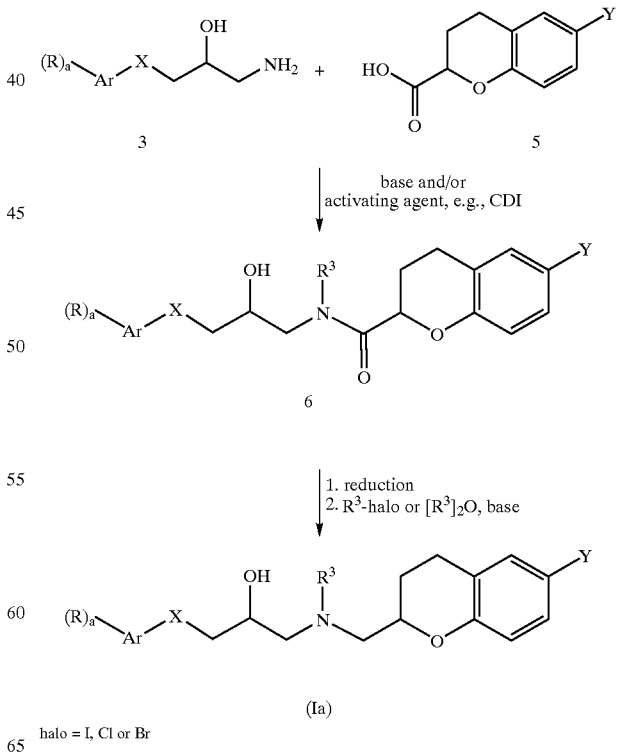

Compounds of Formula I or Formula Ia where Y is any alkyl, cycloalkyl, phenyl or a 5-or 6-membered heterocyclic ring, may be prepared from compounds of Formula I or Formula Ia where Y is a halogen, using the methods described below. For example, a compound of Formula I, wherein Y is iodo, may be prepared by Reaction Scheme 1 using corresponding starting materials 2 or 4, where Y is iodo, each of which may be prepared by Reaction Schemes 14 or 12, respectively. The resulting Formula I compound is then protected by standard methods to give a compound of Formula II, as shown in Reaction Scheme 4. The compound of Formula II is then converted to the boronic ester III, which is then subjected to Suzuki coupling reactions with a Y-halo or Y—$OSO_2CF_3$ compound, in which Y is any alkyl, cycloalkyl, —$(CH_2)_d$—O—$(CH_2)_dR^5$, phenyl, naphthyl, or a 5- or 6-membered heterocycle, to provide Formula IV compounds. Deprotection of Formula IV compounds by acid or fluoride-catalyzed hydrolysis provides the corresponding Formula I compounds.

REACTION SCHEME 4

(II)

pg = protecting group, e.g., Cbz or TBDMS
halo = I, Cl, Br pinacol borane or bispinacol borane
Palladium catalyst, e.g., $Pd(dppf)Cl_2$
anhyd. base, e.g., $Na_2CO_3$ (III)

Y-halo or Y—$OSO_2CF_3$
Palladium catalyst, e.g., $Pd(dppf)Cl_2$
anhyd. base, e.g., $Na_2CO_3$ (IV)

removal of protecting group (I)

The coupling may also be performed in the reverse manner, that is, a boronic acid or boronic ester derivative 14, prepared from a halophenyl or phenyltriflate compound 13a, may be added to the halo compound of Formula IIa, as shown in Reaction Scheme 5, to give Formula Id compounds.

REACTION SCHEME 5

13a pinacol borane or bispinacol borane
Pd Catalyst and base, e.g., $Pd(dppf)Cl_2$
$Et_3N$

14

(IIa)

1. Pd catalyst and base, e.g., $Pd(dppf)Cl_2$ or $Pd(OAc)_2$
   $Na_2CO_3$
2. deprotection (Id)

Z = $CO_2R^1$, F, $R^1$, $OR^1$, phenyl or tetrazolo
halo = I, Cl or Br

Formula 1 compounds wherein Y is $CO_2R^1$ or

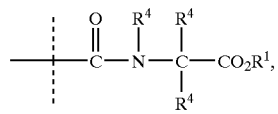

where $R^1$ and $R^4$ are as described above, may be prepared, for example, by a sequence shown in Reaction Scheme 6. The iodo compound of Formula II may be converted to the carboxylic acid of Formula IIb by palladium-catalyzed carboxylation which may then be coupled with any amino acid using standard peptide synthesis techniques, deprotected and hydrolyzed to give compounds of Formula If. This method may be repeated to give Formula I compounds where Y is

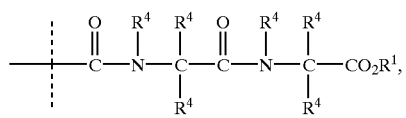

by an analogous sequence of reactions performed on the Formula If compounds.

Other Formula I compounds wherein Y is $NR^1R^1$ or a nitrogen heterocycle may be prepared from the nitro compound of Formula Im by reduction to Ig followed by alkylation to Ih (Reaction Scheme 7). Formula Im compounds may be prepared according to Reaction Scheme 1 or 3, starting from the known Formula 5 or Formula 2 compounds in which $Y=NO_2$.

REACTION SCHEME 7

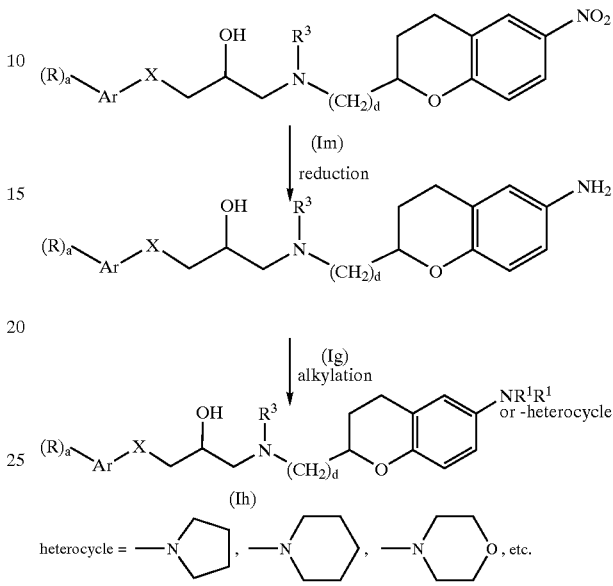

REACTION SCHEME 6

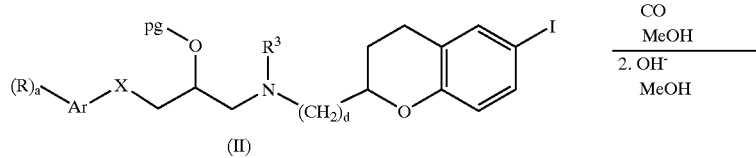

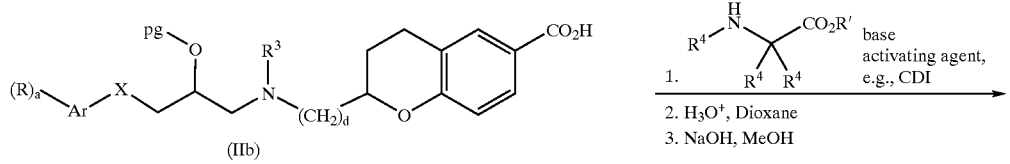

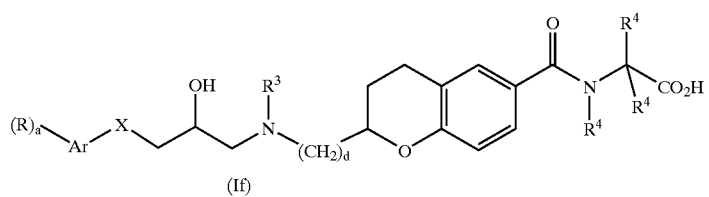

Other Formula I compounds in which Y is —S(O)$_b$Ph—CO$_2$R$^1$, X is O or S(O)$_2$, and b is 0 may be prepared by reduction followed by diazotization and nucleophilic displacement of the diazonium intermediate with an arylthiol to give arylthioethers of Formula Ii (Reaction Scheme 8). Oxidation of the Formula Ii compound with mCPBA or Oxone® generates the Formula Ij compound in which Y is —S(O)$_b$Ph—CO$_2$R$^1$ and b=1 or Formula Ik compound in which Y is —S(O)$_b$Ph—CO$_2$R$^1$ and b=2, depending on the number of equivalents of oxidant used in the reaction.

Formula I compounds in which Y is SR$^1$ or OR$^1$ may be similarly prepared by methods analogous to Reaction Scheme 8, by substituting HSR$^1$ or HOR$^1$ in place of the arylthiol.

Formula I compounds where X is SO or S(O)$_2$ may be prepared by oxidation of Formula I compounds where X is S by using reagents well known in the art for such oxidation such as Oxone® and mCPBA.

Formula I compounds, in which Y is phenyl substituted by a PhSO$_2$NH— or alkylSO$_2$NH— group, may be prepared from the corresponding carboxylic acids as shown in Reaction Scheme 9. An example of dehydrating/acylation conditions useful in this scheme is a mixture of 1-3-dimethylaminopropyl-3-ethylcarbociimide (EDCl) and 4-dimethylaminopyridine (DMAP) in an inert solvent such as dichloromethane.

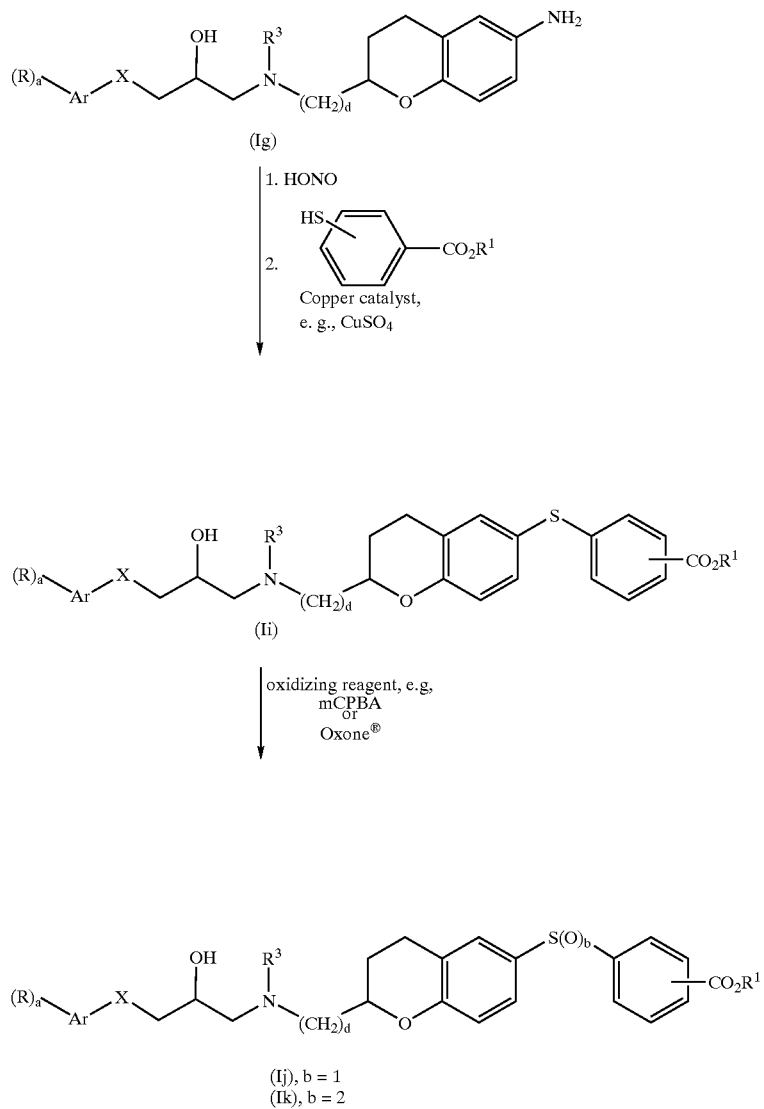

REACTION SCHEME 9

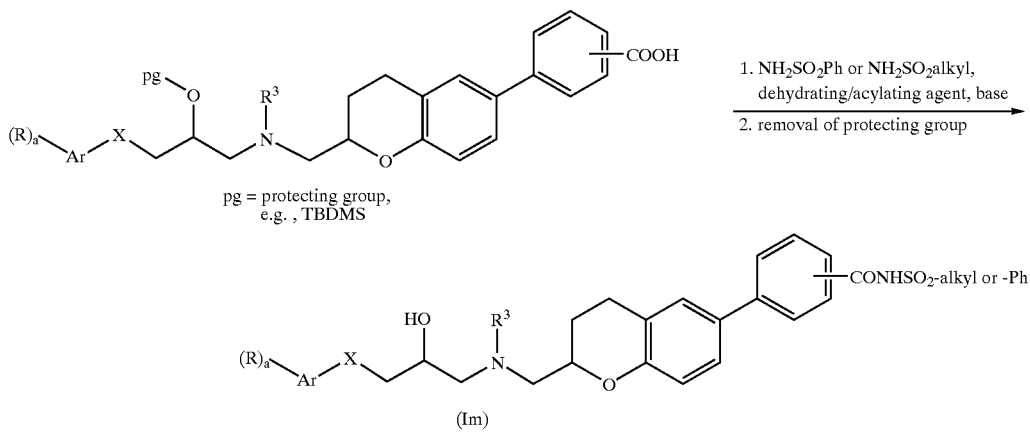

pg = protecting group, e.g., TBDMS

1. $NH_2SO_2Ph$ or $NH_2SO_2alkyl$, dehydrating/acylating agent, base
2. removal of protecting group Other compounds of Formula I may be prepared by standard methods starting from other Formula I compounds, by interchanging the functional groups attached to the Y moiety. Reactions useful for carrying out such interchanges include, but are not limited to esterification, saponification, oxidation, reduction, O- and N-alkylation, acylation, aromatic nucleophilic substitution, and Suzuki coupling reactions. Procedures to carry out such reactions are well nown to those in the art.

The salts and esters of the Formula I compounds of the invention may be readily prepared by conventional chemical processes well known in the art.

General Method of Preparation of Intermediates

The starting materials required to carry out the above described reactions (e.g., epoxides 1, amines 2, amino alcohols 3, aldehydes 4, and carboxylic acids 5) are in many cases commercially available or may be readily prepared by methods known to those skilled in the art. The following routes are exemplary of such methods, but are not intended to be limiting in any way.

The epoxides 1 of Reaction Scheme 1 are commercially available or may be prepared according to one of the many procedures described in the literature known to those skilled in the art, from starting materials which are themselves either commercially available or known in the art. One such general method of preparation is illustrated in Reaction Scheme 10, in which a substituted aryl or heteroaryl hydroxy or thiol compound (i.e., where X is S or O), such as a phenol, thiophenol, hydroxypyridine, hydroxybenzofuran, thiopyridine, hydroxyindole, hydroxyquinoline, thioquinoline and the like is allowed to react with a glycidyl-, alkyl- or arylsulfonate in the presence of a strong base such as sodium hydride. The alkyl or aryl sulfonate used in this reaction may be racemic or an enantiomerically pure compound, such as (2S)-(+)- or (2R)-(−)-glycidyl tosylate, both of which are commercially available.

REACTION SCHEME 10

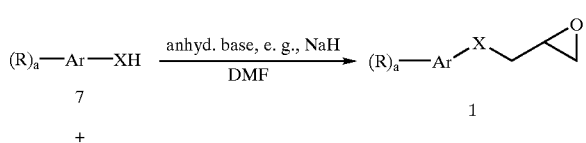

-continued

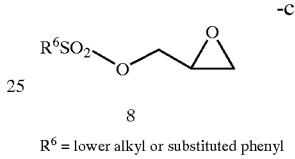

$R^6$ = lower alkyl or substituted phenyl

The amino alcohols 3 are either commercially available, known in the art, or may be prepared by ring opening of the epoxides 1 with a nitrogen nucleophile, such as dibenzylamine or phthalimide, in the presence of a base. Removal of the phthalimide by cleavage with hydrazine or the benzyl groups by hydrogenolysis provides the desired amino alcohol of Formula 3. An example of this is shown in Reaction Scheme 11.

REACTION SCHEME 11

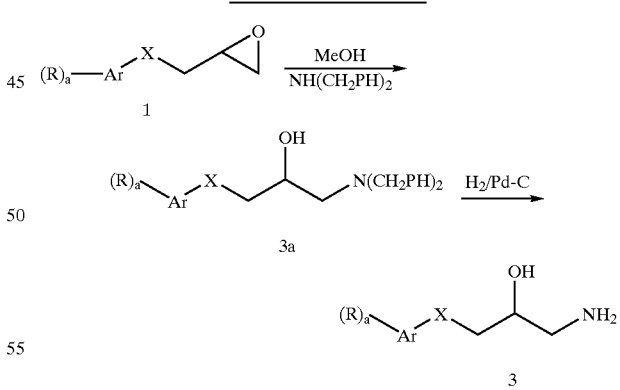

Synthesis of aldehyde starting materials of Formula 4 may be accomplished from the carboxylic acids of Formula 5 by reduction with borane followed by an oxidation, for example, under Swern conditions as shown in Reaction Scheme 12. This method is compatible with a wide variety of Y groups, although in some cases a protection group may also be employed and removed in a subsequent step.

REACTION SCHEME 12

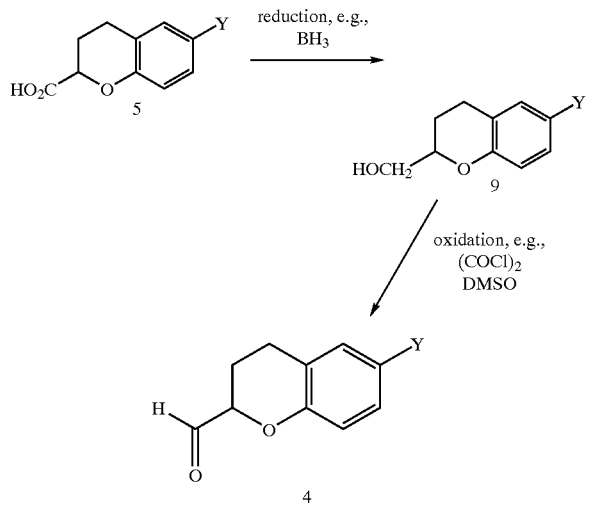

The carboxylic acids of Formula 5 are generally available from the known unsubstituted chroman carboxylic acid, 5a (WO 99/32476), by various aromatic substitution reactions at the 6-position of the chroman ring and further elaboration of these products. For example, halogenation, e.g., iodination of 5a gives the 6-iodo compound 5b and nitration gives predominantly the 6-nitro analog, 5c (U.S. Pat. No. 6,051,586) as shown in Reaction Scheme 13.

REACTION SCHEME 13

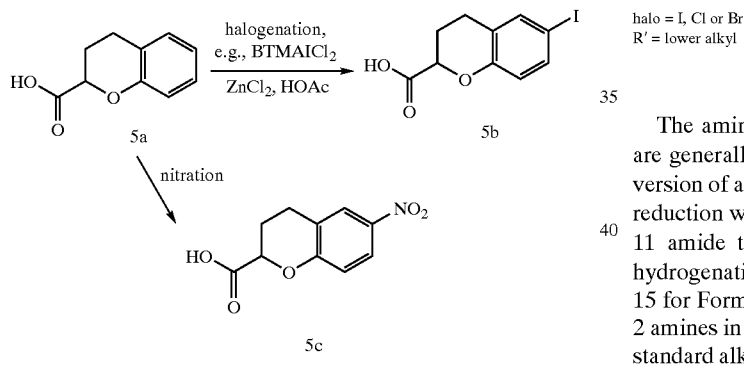

Conversion of 5b or 5c to other carboxylic acids of general Formula 5 where Y is $-(CH_2)_nCOR^2$ and n is 0, 1 or 2 has been described in the art (U.S. Pat. No. 6,051,586). Other compounds of Formula 5 where Y is any alkyl, cycloalkyl, $-(CH_2)_d-O-(CH_2)_dR^5$, phenyl, naphthyl, or a 5- or 6-membered heterocycle, may be prepared by Suzuki coupling of a halo-Y group to a iodo chroman ester, prepared by standard esterification methods from the iodo chroman acid 5b.

REACTION SCHEME 14

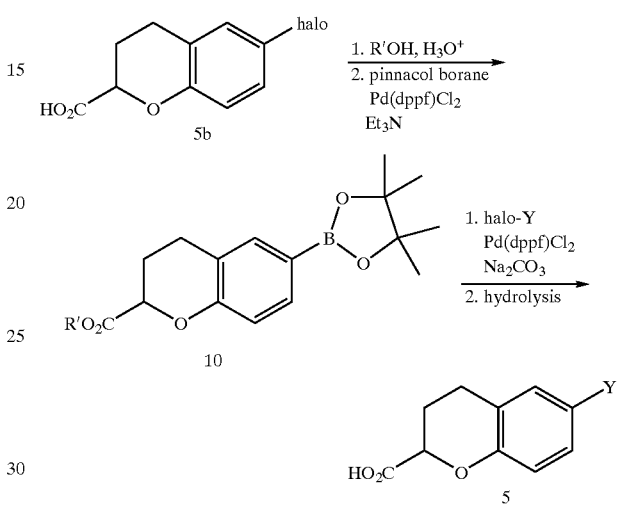

halo = I, Cl or Br
R' = lower alkyl

The amine starting materials of Formula 2 in which d=1 are generally available by standard methods involving conversion of a carboxylic acid 5 to an amide of Formula 11 and reduction with borane, or further conversion of the Formula 11 amide to the nitrile of Formula 12 and reduction by hydrogenation. This sequence is shown in Reaction Scheme 15 for Formula 2 amines wherein d=1 and $R^3$ is H. Formula 2 amines in which $R^3$ is other than H may be prepared by the standard alkylation or acylation methods known in the art, as described above.

REACTION SCHEME 15

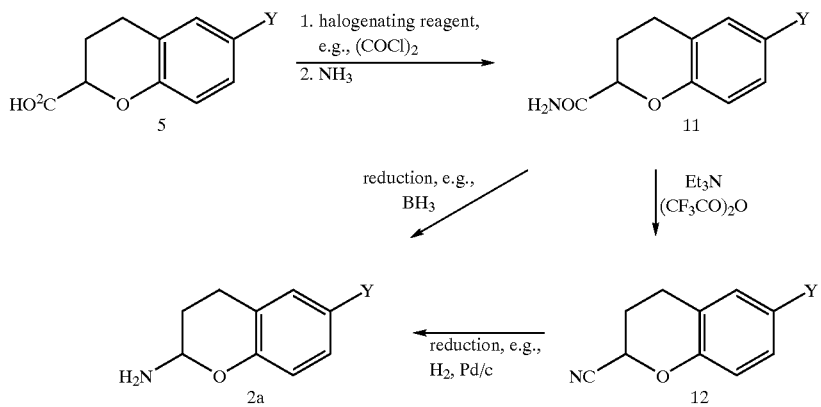

Formula 2 amines in which d is 2 or 3 may be prepared by standard homologation sequences of known intermediates where d=1. For example, aldehydes of Formula 4 can undergo an alkyl chain extension according to well known procedures such as that described by Wittig, G. et al., in *Chem. Ber.,* 1962, 2514, and the process may be repeated in order to prepare the acetic and propionic acid homologues of Formula 5. These chain-extended acids may used in place of the acid of Formula 5 by a method analogous to Reaction Scheme 15, to provide a variety of Formula 2 amines in which d=2 or 3.

Formula 2 amines in which Y is other than hydrogen or halo may be prepared by palladium-catalyzed coupling reactions on the N-protected amine of Formula 15a, followed by deprotection, as shown in Reaction Scheme 16. Formula 2 amines prepared in this way in which the Y group is substituted by an acid, ester, alcohol, ketone, sulfide, or nitro group can also provide additional Formula 2 amines by manipulation of that functional group by directed hydrolysis, esterification, reduction, oxidation, and/or reduction reactions and the like.

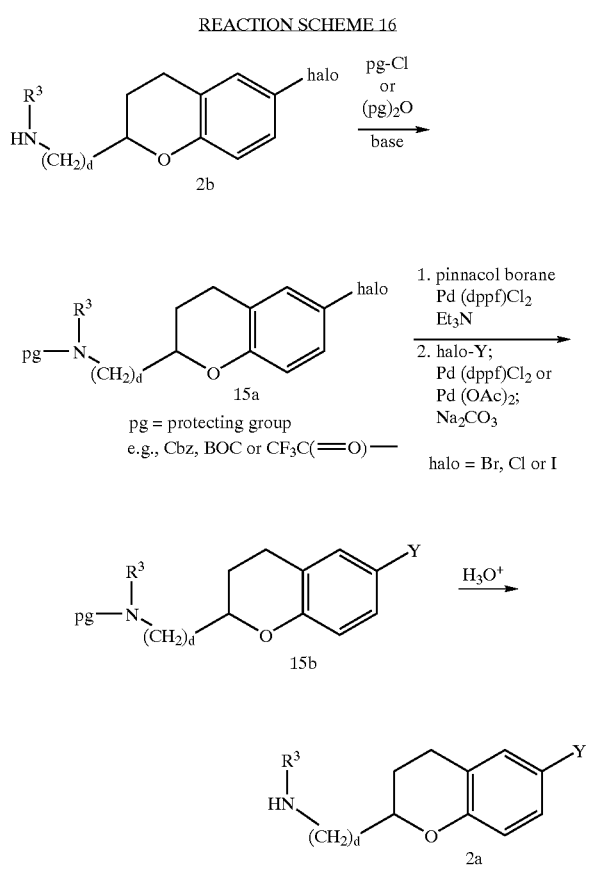

Similarly, the unsubstituted amine 2c, after protection may be directly substituted at the 6-position of the chroman under Friedel-Crafts alkylation or acylation conditions to provide compounds of Formula 15b in which Y is any alkyl, cycloalkyl, or $CO_2R^1$ group. An example of this where Y is an optionally substituted alkanoic acid group is shown in Reaction Scheme 17.

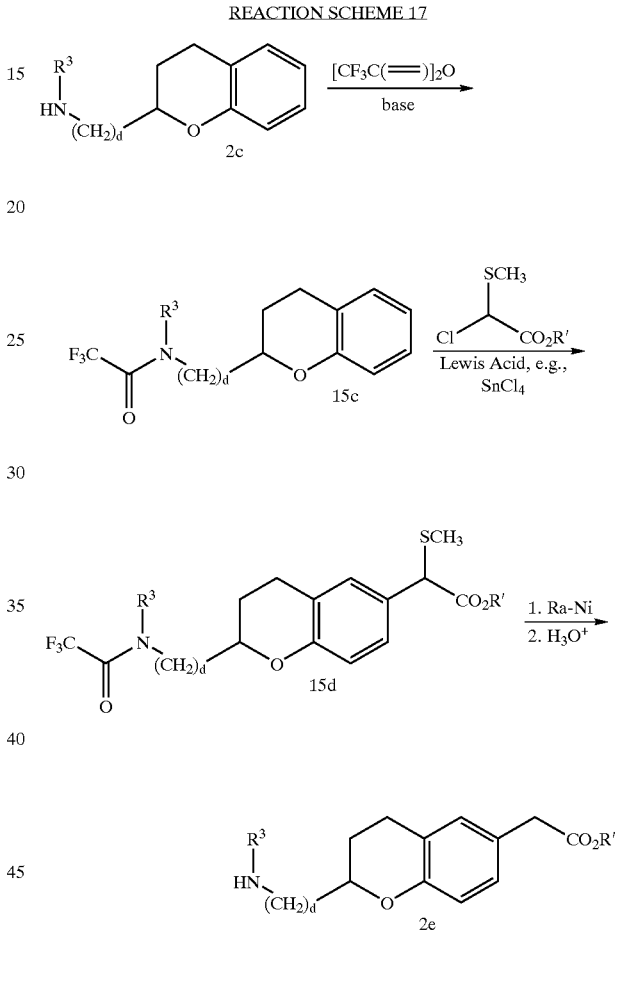

Alcohol intermediates of Formula 9 in which Y is other than hydrogen or halo may also be prepared from the iodo alcohol, 9a, by the previously described Suzuki coupling methodology as shown in Reaction Scheme 18. This may be accomplished either directly on 9a, or via a 4-step sequence involving protection of the alcohol to 16a, for example as the t-butyltrimethylsilyl ether, conversion of the halide to the boronic ester, Suzuki coupling to 16b, and finally deprotection to 9.

REACTION SCHEME 18

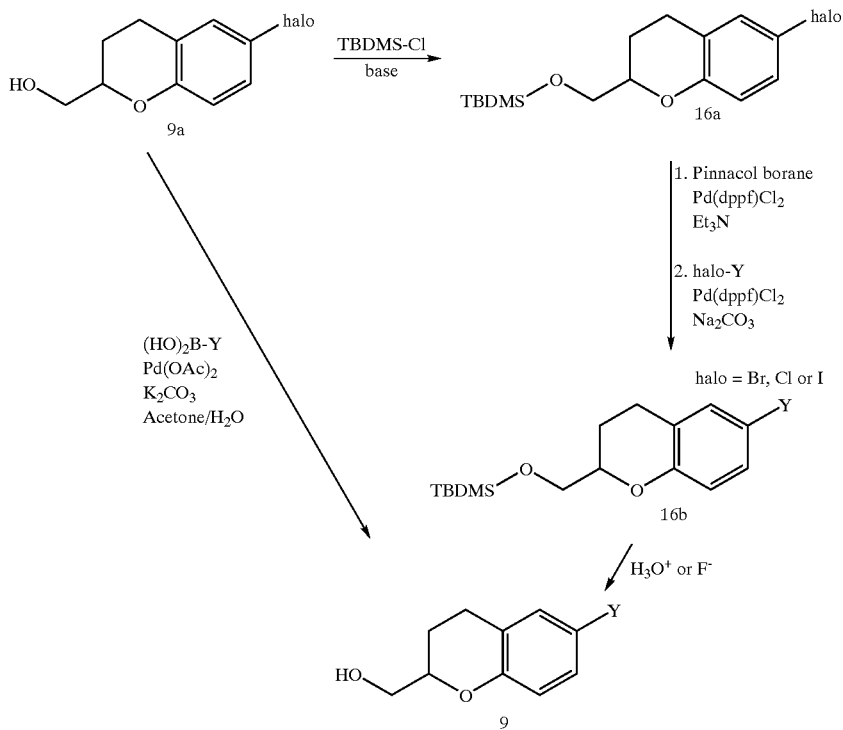

The halo-Y compounds used in Reaction Schemes 14, 16, and 18 where halo is iodo, chloro, or bromo, and Y is any alkyl, cycloalkyl, —$(CH_2)_d$—O—$(CH_2)_dR^5$, phenyl, naphthyl, or a 5- or 6-membered heterocycle, are either commercially available or synthesized by standard methods known to those skilled in the art. One such standard method is direct halogenation of a known H—Y compound with a halogenating agent; other methods include the functional group conversion of HO—Y, $NH_2$—Y compounds to halo-Y compounds by standard substitution methods. Y-halo compounds containing a fluoro substituent may be converted to Y-halo compounds containing alkylamino moiety by nucleophilic aromatic substitution catalyzed by cesium carbonate.

An illustration of the preparation of halo of halo-Y compounds of Formula 13a and 13b, where Y represents an oxazole or a thiazole, prepared by direct halogenation of the unsubstituted compound 17, or by diazotization of a $NH_2$—Y compound 18 as shown in Reaction Scheme 19.

REACTION SCHEME 19

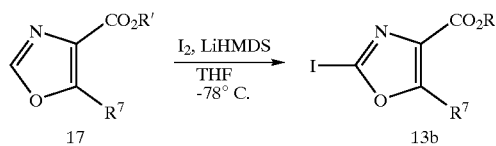

-continued

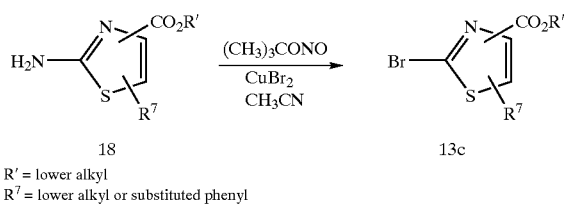

R' = lower alkyl
$R^7$ = lower alkyl or substituted phenyl

The heterocyclic intermediates, 17, and 18, used to prepare 13a and 13b are accessible by standard methods from acyclic materials, for example, as shown in Reaction Schemes 20, 21, and 22.

REACTON SCHEME 20

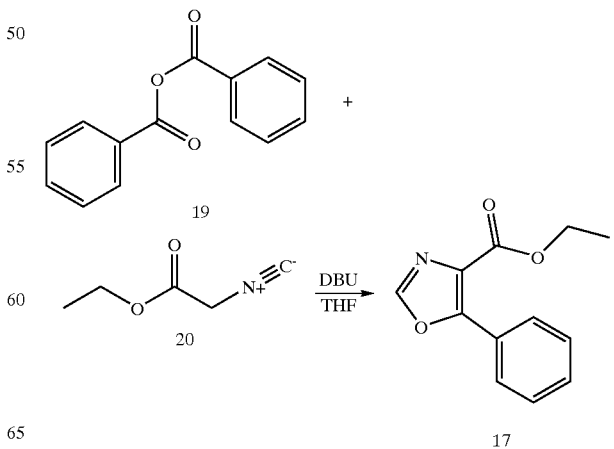

REACTION SCHEME 21

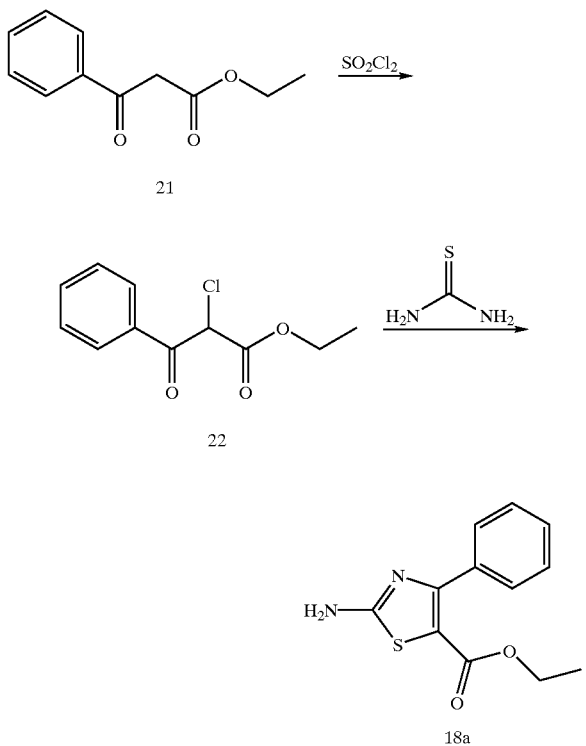

REACTION SCHEME 22

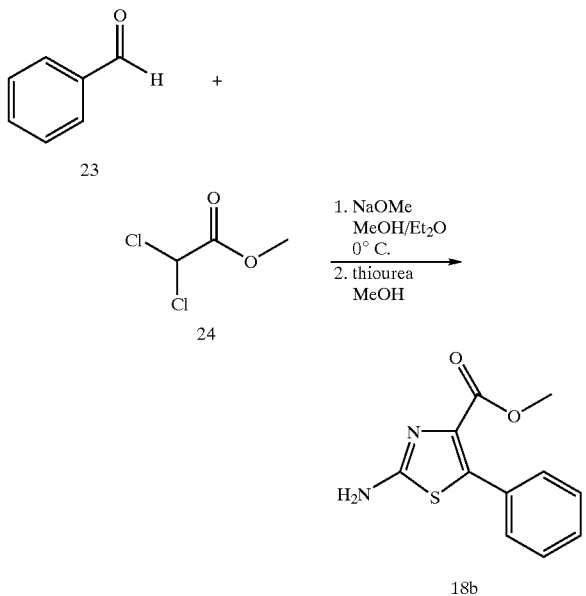

Using a combination of the above Reaction Schemes, a wide variety of compounds of Formula I may be prepared. Further illustration of these methods are in the specific Examples described hereinbelow. These examples are not intended nor should they be construed to limit the invention in any way.

ABBREVIATIONS AND ACRONYMS

When the following abbreviations are used herein, they have the following meaning:

| Abbreviation | Meaning |
|---|---|
| $Ac_2O$ | acetic anhydride |
| anhy | anhydrous |
| BOC | tert-butyloxycarbonyl |
| $BTMAICl_2$ | benzyltrimethylammonium dichioriodate |
| n-BuLi | n-butyllithium |
| Cbz | benzyloxycarbonyl |
| CDI | carbonyldiimidazole |
| Cl-MS | chemical ionization mass spectroscopy |
| conc. | concentrated |
| mCPBA | 3-chloroperoxybenzoic acid |
| de | diastereomeric excess |
| dec. | decomposition |
| DBU | 1,8-diazabicyclo[5.4.0]undec-7-ene |
| DMAP | 4-dimethylaminopyridine |
| DME | dimethoxyethane |
| DMF | N,N-dimethylformamide |
| DMSO | dimethylsulfoxide |
| EDCl | 1-(3-dimethylaminopropyl)-3-ethylcarbodiimide |
| EtOAc | ethyl acetate |
| EtOH | ethanol (100%) |
| $Et_2O$ | diethyl ether |
| $Et_3N$ | triethylamine |
| HPLC ES-MS | high performance liquid chromatography-electrospray mass spectroscopy |
| KOt-Bu | potassium tert-butoxide |
| LC-MS | liquid chromatography-mass spectroscopy |
| $LiAlH_4$ | lithium aluminum hydride |
| $LiBH_4$ | lithium borohydride |
| LiHMDS | lithium bis(trimethylsilyl)amide |
| MeOH | methanol |
| MS | mass spectroscopy |
| MSTFA | N-methyl-N-(trimethylsilyl)trifluoroacetamide |
| $NaBH_4$ | sodium borohydride |
| NMM | 4-methylmorpholine |
| Oxone ® | potassium peroxymonosulfate |
| $Ph_3P$ | triphenylphosphine |
| $Pd(dppf)Cl_2$ | 1,1'-bis(diphenylphosphino)ferrocene] dichloropalladium(II) |
| $Pd(PPh_3)_4$ | tetrakis(triphenylphosphine)palladium(0) |
| $Pd(OAc)_2$ | palladium acetate |
| RT | retention time |
| rt | room temperature |
| TBAF | tetrabutylammonium fluoride |
| TBDMSCI | tert-butyldimethylsilyl chloride |
| TBDMSOTf | ted-butyldimethylsilyl triflate |
| THF | tetrahydrofuran |
| TFA | trifluoroacetic acid |

General Experimental Procedures

HPLC-electrospray mass spectra (HPLC ES-MS) were obtained using a Hewlett-Packard 1100 HPLC equipped with a quaternary pump, a variable wavelength detector, a YMC Pro C18 2.0 mm×23 mm column, and a Finnigan LCQ ion trap mass spectrometer with electrospray ionization. Gradient elution from 90% A to 95% B over 4 minutes was used on the HPLC. Buffer A was 98% water, 2% acetonitrile, and 0.02% TFA. Buffer B was 98% acetonitrile, 2% water, and 0.018% TFA. Spectra were scanned from 140–1200 amu using a variable ion time according to the number of ions in the source.

Combinatorial/parallel reactions were carried out in 8-mL glass vials with Teflon-lined screw caps, or in a polypropylene reaction block consisting of an 8×12 matrix of ninety-six 2.0-mL reaction wells, with each reaction well incorporating a 15–45 micron polyethylene frit; reaction blocks of this type are commercially available as FlexChem™ reactor blocks from Robbins Scientific Corporation, Sunnyvale, Calif. The reactor blocks are sealed with rubber gaskets and a clamping device, and can be heated with mixing by rotation in an oven (Robbins Scientific). LC/MS analyses were carried out with electrospray ionization, by using a YMC Pro C18 3 μm column, 4.0 mm×23 mm, at 1.5 mL/min, with 0.5 min at 90% solvent A, then gradient elution at 0.5 to 4.0 min from 90% A to 5% A, then 0.5 min at 5% solvent A. Solvent A was 98% water and 2% acetonitrile, containing 0.02% trifluoroacetic acid; solvent B was 98% acetonitrile and 2% water, containing 0.02% trifluoroacetic acid.

The following examples are presented to illustrate the invention described herein, but should not be construed as limiting the scope of the invention in any way.

EXAMPLE 1

Preparation of (2R)-3,4-dihydro-2H-chromene-2-carboxamide

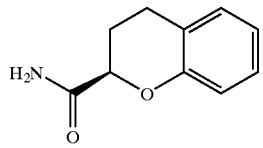

To a solution of (2R)-3,4-dihydro-2H-chromene-2-carboxylic acid (WO 99/32476) (17.8 g, 0.1 mol) in anhydrous dichloromethane (170 mL) cooled in an ice-water bath containing 4 drops of N, N-dimethylformamide were added oxalyl chloride (13.4 mL, 0.16 mol) via a syringe in 10 minutes under argon. The resulting mixture was then stirred at room temperature for 15 h. Solvent was removed in vacuo to afford the acid chloride cleanly: $^1$H NMR (CDCl$_3$) δ2.31–2.51 (m, 2H), 2.72–2.91 (m, 2H), 5.01 (t, J=4.2 Hz, 1H), 7.04–7.06(t, J=8.7 Hz, 2H), 7.03–7.06 (d, J=6.9 Hz, 1H); 7.13–7.18 (t, J=8.1 Hz, 1H).

To a 2-L 3-necked round-bottomed flask containing ethyl acetate (633 mL) and ammonium hydroxide (158.2 mL) cooled in an ice-water bath with vigorous stirring was added a solution of the above acid chloride in ethyl acetate (159 mL) dropwise in 15 minutes. The reaction mixture was stirred for additional 20 minutes. The organic layer was separated and washed with water (200 mL), brine (200 mL), and dried over anhydrous sodium sulfate. Removal of the solvent in vacuo afforded the chroman amide as a white solid (16.9 g, 95% yield): $^1$H NMR (CDCl$_3$)δ2.01–2.14 (m, 1H), 2.37–2.46 (m, 1H), 2.75–2.95 (m, 2H), 4.53–4.57 (dd, J=9.3, 2.7 Hz, 1H), 5.75 (s, broad, 1H), 6.60(s,broad, 1H), 6.86–6.93 (m, 2H), 7.07–7.16 (m, 2H), CI-MS m/z 178 (M+H$^+$).

EXAMPLE 2

Preparation of (2R)-3,4-dihydro-2H-chromen-2-ylmethylamine Hydrochloride

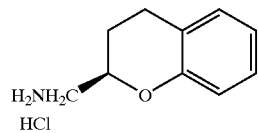

The amide of Example 1 (16.9 g, 95 mmol) and tetrahydrofuran (100 mL) were charged in a dry 1-L 3-necked round-bottomed flask. The mixture was heated to reflux under argon with stirring to obtain a clear solution. To this solution was then added borane/dimethyl sulfide complex (95 mL, 2M in THF) in about 30 minutes. After completion of this addition, the reaction was further refluxed for 1 h. Additional borane/dimethyl sulfide (80 mL) was added to the reaction and the mixture was further refluxed for 1 h. Heating was removed and replaced with an ice-water bath to cool the reaction mixture to room temperature. Methanol (43 mL) was then added to the reaction and it was stirred for 30 minutes. The reaction mixture was then concentrated in vacuo to remove 140 mL of liquid. The residue was then treated with ether/HCl (1 M) carefully to obtain a white suspension which was cooled in an ice-water bath for 30 minutes before vacuum filtration to obtain the product as a white powder (16.3 g, 87% yield): $^1$H NMR (DMSO-d6) δ1.60–1.77 (m, 1H), 2.00–2.08 (m, 1H), 2.65–2.85 (m, 2H), 2.95–3.20 (m, 2H), 4.20–4.30 (m, 1H), 6.75–6.85 (m,2H), 704–7.09 (m, 2H); 8.30 (s, broad, 3H); CI-MS m/z 164 (M+H$^+$).

EXAMPLE 3

Preparation of N-[(2R)-3,4-dihydro-2H-chromen-2-ylmethyl]-2,2,2-trifluoroacetamide

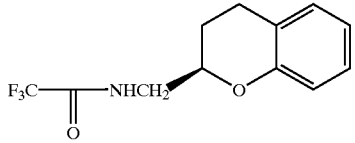

The amine HCl salt of Example 2 (16.3 g, 82.6 mmol) was dissolved in 1N aqueous sodium hydroxide solution (91 mL) followed by extraction with dichloromethane (90 mL×3). The combined organic layer was washed with brine (50 mL) and dried over anhydrous sodium sulfate. Removal of solvent in vacuo afforded the free base chroman amine as colorless oil which was mixed with pyridine (14.2 mL) in dichloromethane (136 mL) under argon.

This mixture was cooled in an ice-water bath and trifluoroacetic anhydride (23.3 mL) was then added carefully in about 10 minutes. The cooling bath was removed and the reaction was stirred at room temperature for 4 hours. It was then poured onto crushed ice (130 g). The organic layer was separated, washed with brine (50 mL) and dried over anhydrous sodium sulfate. Removal of solvent in vacuo afforded the product cleanly (19.7 g, 92% yield): $^1$H NMR (CDCl$_3$) δ1.75–1.86 (m, 1H), 1.99–2.12 (m, 1H), 2.76–2.97 (m, 2H), 3.46–4.26 (m, 3H), 6.80–6.91 (m, 2H), 7.03–7.14 (m, 2H); CI-MS m/z 260 (M+H$^+$). The crude product was used for the next step without further purification.

EXAMPLE 4

Preparation of ethyl (methylsulfanyl)[(2R)-2-(3,3.3-trifluoro-2-oxopropyl)-3,4-dihydro-2H-chromen-6-yl]acetate

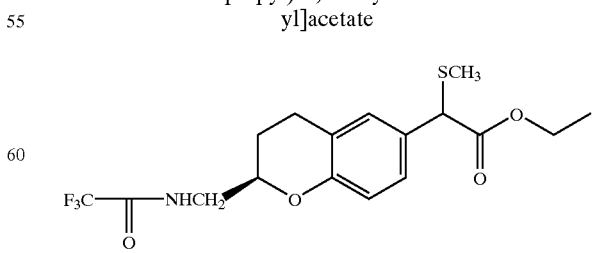

To a solution of N-[(2R)-3,4-dihydro-2H-chromen-2-ylmethyl]-2,2,2-trifluoroacetamide (12.96 g, 50 mmol) and α-chloro-2-(methylthio) acetate (9.28 g, 55 mmol) in dichloromethane (75 mL) at 0° C. was added tin(IV) chloride (55 mL, 1M in CH$_2$Cl$_2$) via a syringe slowly. The mixture became yellow rapidly and precipitation started to form. After completion of addition, the reaction was stirred at room temperature for 30 minutes. It was then quenched by addition of water (100 mL). The organic layer was separated and dried over anhydrous sodium sulfate and concentrated in vacuo to afford the crude product as a brown oil (diastereomeric mixture): $^1$H NMR (CDCl$_3$) δ1.30 (m, 3H), 1.76 (m, 2H), 2.18 (m, 4H), 2.90 (m, 2H), 4.20 (m, 5H), 6.65–6.79 (dd, J=8.1, 7.8 Hz, 1H), 7.18 (m, 2H); CI-MS m/z 392 (M+H$^+$). The crude was used for next step without further purification.

EXAMPLE 5

Preparation of ethyl [(2R)-2-(3,3,3-trifluoro-2-oxopropyl)-3,4-dihydro-2H-chromen-6-yl]acetate

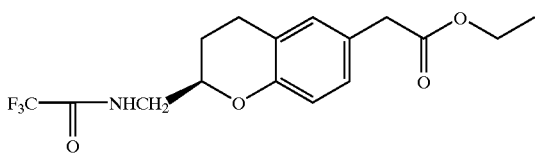

The above crude thiomethyl compound of Example 4 was dissolved in absolute ethanol (340 mL) under argon and mixed with Raney nickel (17 teaspoons) freshly washed with water and ethanol (3 times). The resulting mixture was stirred vigorously at room temperature for 1 hours. Stirring was stopped, and the liquid layer was removed by decanting. The catalyst was then washed with ethanol (250 mL) and dichloromethane (250 mL). The liquid was removed by decanting in each case. The combined liquid layer was concentrated in vacuo. The residue was dissolved in methyl t-butyl ether (300 mL), washed with water (200 mL), and brine (200 mL) and dried over anhydrous sodium sulfate. Removal of solvent in vacuo afforded the crude product as a colorless oil (14.3 g, 83%): $^1$H NMR (CDCl$_3$) δ1.26 (t, J=7.2 Hz, 3H), 1.80 (m, 1H), 2.00 (m, 1H), 2.70–2.95 (m, 2H), 3.50 (m, 3H), 3.80–3.85 (m, 1H), 4.15 (m, 4H), 6.76 (d, J=8.4 Hz, 1H), 6.98 (s,1H), 7.02 (d, J=8.7 Hz, 1H); CI-MS m/z 346 (M+H$^+$). The crude was used for next step without further purification.

EXAMPLE 6

Preparation of [(2S)-2-methyl-3,4-dihydro-2H-chromen-6-yl]acetic Acid Hydrochloride

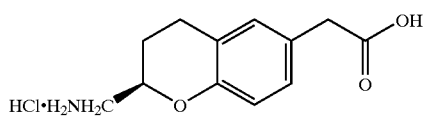

The crude trifluoroacteyl protected amine of Example 5 was heated in 6N HCl (200 mL) at 80–95° C. for 2 hours under argon. The reaction became a white suspension after it was cooled down to room temperature. The solid was collected by vacuum filtration and dried by suction (5.95 g, 56%): $^1$H NMR (DMSO-d6) δ1.63 (m, 1H), 2.00 (m, 1H), 2.70 (m, 2H), 3.00 (m, 1H), 3.11 (m, 1H), 4.20 (m, 1H), 6.70 (d, J=8.7 Hz, 1H), 6.95 (d, J=9.0 Hz, 1H), 6.96 (s, 1H), 8.25 (s, broad, 3H); CI-MS m/z 222 (M+H$^+$).

EXAMPLE 7

Preparation of (2R)-6-iodo-3,4-dihydro-2H-chromene-2-carboxylic Acid

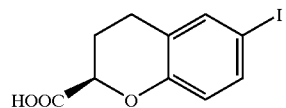

(2R)-3,4-Dihydro-2H-chromene-2-carboxylic acid (WO 99/32476) (26.7 g, 150 mmol), benzyltrimethyl-ammonium dichloroiodate (50.1 g, 144 mmol) and zinc chloride (25.3 g, 186 mmol) were stirred in glacial acetic acid (500 mL) under argon at room temperature for 18 hours. The solid was removed by vacuum filtration and then washed with acetic acid (100 mL). The filtrate was concentrated in vacuo to obtain a solid which was slurried in water (300 mL). The crude product was obtained as a pink solid after vacuum filtration and dried (38.3 g, 84%): $^1$H NMR (DMSO-d6) δ1.95–2.10 (m, 1H), 2.60 (m, 1H), 2.70–2.80 (m, 1H), 4.79 (dd, J=6.0, 3.9 Hz, 1H), 6.63 (d, J=8.4 Hz, 1H), 7.36 (dd, J=8.1, 1.8 Hz, 1H), 7.38 (d, J=1.8 Hz, 1H). CI-MS m/z 305 (M+H$^+$). The crude was used for next step directly.

EXAMPLE 8

Preparation of [(2R)-6-iodo-3,4-dihydro-2H-chromen-2-yl]methanol

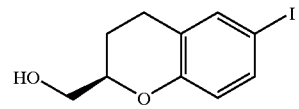

A solution of borane-THF complex (1M in THF, 23.4 mmol, 1.2 eq) was added dropwise to a solution of (2R)-6-iodo-3,4-dihydro-2H-chromene-2-carboxylic acid (Example 7, 19.5 mmol, 1.0 eq.) in THF (45 mL) at 10° C. The resulting reaction mixture was stirred at 45° C. for 1.5 hours and was then cooled to 10° C. Next, water was added followed by saturated NaHCO$_3$ solution. The resulting two-phase mixture was separated and aqueous phase was extracted with ethyl acetate. The combined organic extracts were washed with brine, dried over anhydrous sodium sulfate, concentrated to afford the product as a white solid in quantitative yield that was used without further purification.

EXAMPLE 9

Preparation of (2R)-6-iodo-3,4-dihydro-2H-chromene-2-carboxamide

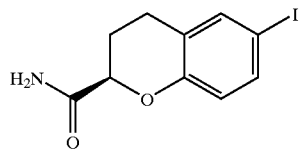

The crude carboxylic acid of Example 7 (30.4 g, 100 mmol) and CDI (19.5 g, 120 mmol) were stirred in N,N-dimethylformamide (300 mL) at room temperature for 2 hours to obtain a yellow solution. To this solution was then added ammonium acetate (23.1 g, 300 mmol). The resulting mixture was stirred for 3 hours. It was then cooled in an ice-water bath and water (400 mL) was then added dropwise to the reaction mixture to obtain a fine white precipitation which was stirred for 12 hours. The solid was collected by vacuum filtration, washed with water and dried by suction (25.8 g, 85%): $^1$H NMR (DMSO-d6) δ1.75–1.90 (m, 1H), 2.00–2.15 (m, 1H), 2.55–2.80 (m, 2H), 4.43–4.47 (dd, J=8.7, 3.3 Hz, 1H), 6.65 (d, J=8.1 Hz, 1H), 7.35 (m, 2H). CI-MS m/z 304 (M +H$^+$).

EXAMPLE 10

Preparation of [(2R)-6-iodo-3,4-dihydro-2H-chromen-2-yl]methylamine Hydrochloride

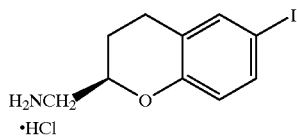

The carboxamide of Example 9 (25.0 g, 82.5 mmol) was suspended in anhydrous tetrahydrofuran (200 mL) at reflux under argon. To this suspension was then added borane/dimethyl sulfide complex (83 mL, 2M in THF) dropwise. The reaction became a clear solution after the addition which was stirred at reflux for 1 h hour. Additional borane reagent (70 mL) was added and the reaction was further refluxed for 1 h hour. Heating was removed and the reaction was cooled to 0° C. with an ice-water bath. Methanol (38 mL) was added slowly to quench the reaction. The reaction mixture was concentrated in vacuo to about 40% of its initial volume. The residue was then treated with ether/HCl (1 M) to obtain white precipitate which was filtered, washed with ether, and dried by suction (11.7 g, 44%): $^1$H NMR (DMSO-d6) δ1.65 (m, 1H), 2.00 (m, 1H), 2.75 (m, 2H), 2.99 (dd, J=13.2, 8.1 Hz, 1H), 3.09–3.1.

EXAMPLE 11

Preparation of benzyl [(2R)-6-iodo-3,4-dihydro-2H-chromen-2-yl]methylcarbamate

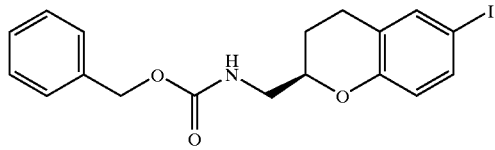

To a mixture of (R)-6-iodo-chroman-2-methylamine hydrochloride of Example 10 (3.3 g, 10 mmol) and benzylchloroformate (1.57 mL, 11 mmol) in tetrahydrofuran (30 mL), cooled in an ice-water bath, was added slowly 1N aqueous sodium hydroxide in 20 minutes. The resulting mixture was stirred for 1 hour. The organic layer was separated and concentrated in vacuo. The aqueous layer was extracted with ethyl acetate (50 mL×2). The combined ethyl acetate layer was combined with the above residue and washed with water (50 mL), brine (50 mL), and dried over anhydrous sodium sulfate. Removal of the solvent in vacuo afforded the crude product as a white solid (4.2 g, 99%).

EXAMPLE 12

Preparation of tert-butyl (2E)-3-[(2R)-2-({[(benzyloxy)carbonyl]amino}methyl)-3,4-dihydro-2H-chromen-6-yl]-2-propenoate

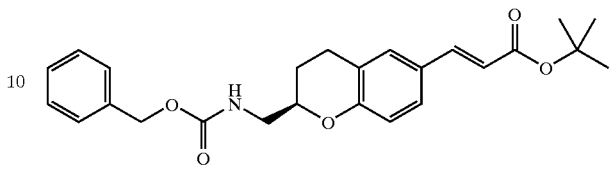

Palladium acetate (224 mg, 1 mmol) was added to a mixture of the carbamate of Example 11 (4.2 g, 10 mmol), triethylamine (2.1 mL, 15 mmol), and t-butyl acrylate (1.76 mL, 12 mmol) in acetonitrile (50 mL) previously degassed with argon for 20 minutes. The resulting mixture was heated at gentle reflux for 26 hours. It was cooled to room temperature. The catalyst was removed by filtration. The filtrate was concentrated in vacuo. The residue was dissolved in ethyl acetate (50 mL), washed with water (50 mL), brine (50 mL), dried over anhydrous sodium sulfate, and filtered over a pad of silica gel. Removal of solvent in vacuo afforded the product as an oil (4.0 g, 95%): $^1$H NMR (CDCl$_3$) δ1.50 (s, 9H), 1.70 1.85 (m, 1H), 200 (m, 1H), 2.80 (m, 2H), 3.40(m, 1H), 3.65 (m, 1H), 5.12 (s, 2H), 5.25 (m, 1H), 6.21 (d, J=15.3 Hz,1H), 6.76 (d, J=8.4 Hz, 1H), 7.20–7.40 (m, 7H), 7.49 (d, J=15.9 Hz, 1H); CI-MS m/z 424 (M+H$^+$).

EXAMPLE 13

Preparation of tert-butyl 3-[(2R)-2-(aminomethyl)-3.4-dihydro-2H-chromen-6-yl]propanoate

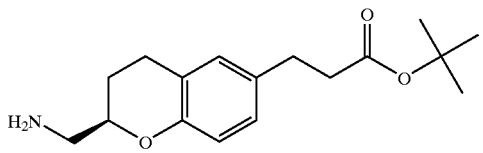

A mixture of carbamate of Example 12 (10.8 g, 23.6 mmol), ammonium formate (29 g, 460 mmol) and palladium hydroxide on carbon (Pearlman's catalyst) (4.3 g) in absolute ethanol (250 mL) was heated at 50° C. for 4 hours under argon. Some white solid appeared in the condenser. The reaction mixture was vacuum filtered through a pad of Celite. The filtrate was concentrated in vacuo to obtain an off-white solid which was subsequently dissolved in 1 N sodium hydroxide solution (200 mL). The mixture was extracted with ethyl acetate (200, 200, 100 mL). The combined organic layer was washed with brine (100 mL) and dried over anhydrous sodium sulfate. Removal of solvent in vacuo afforded the desired product cleanly as an oil (6.0 g, 88%): $^1$H NMR (CDCl$_3$) δ1.40 (s, 9H), 1.70–1.81 (m, 1H), 1.90–2.00 (m, 1H), 2.46–2.51 (t, J=6.9 Hz, 2H), 2.70–2.85 (m, 4H), 2.93 (d, J=5.4 Hz, 2H), 3.90–4.00 (m, 1H), 6.73 (d, J=8.4 Hz, 1H), 6.87 (s, 1H), 6.90 (d, J=8.1 Hz, 1H); CI-MS m/z 292 (M+H$^+$).

EXAMPLE 14

Preparation of tert-butyl 3-[(2S)-2-(aminomethyl)-3,4-dihydro-2H-chromen-6-yl]propanoate

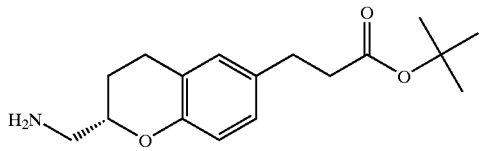

The (S)-enantiomer was synthesized in the same fashion as described for the (R)-enantiomer (Example 13) starting from (2S)-3,4-dihydro-2H-chromene-2-carboxylic acid (WO 99/32476).

EXAMPLE 15

Preparation of (2S)-2-(phenoxymethyl)oxirane

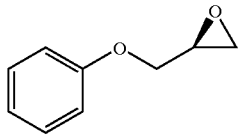

This compound was prepared by a procedure similar to that described by Sharpless, et al. (*J. Org. Chem.* 1989, 54, pp 1295–1304). A solution of phenol (24.1 mmol, 1.1 eq.) in dry DMF (20 mL) was added to a suspension solution of sodium hydride (60% in mineral oil, 28.5 mmol, 1.3 eq.) in dry DMF (80 mL) slowly at room temperature. Within a period of 10 minutes, the turbid mixture became a clear solution. This clear solution was stirred for 30 minutes at which time a solution of (2S)-(+)-glycidyl tosylate (21.9 mmol, 1.0 eq.) was added slowly. The resulting mixture was stirred at room temperature overnight and quenched with saturated ammonium chloride solution. The two-phase mixture was diluted with water and extracted with diethyl ether. The combined organic extracts were washed with saturated NaHCO$_3$, brine, dried over anhydrous sodium sulfate, concentrated and purified by medium pressure column chromatography (Biotage 40S normal phase silica gel column, hexanes:EtOAc=6:1). The product was obtained as a colorless oil in 96% yield. R$_f$=0.24 (hexanes:EtOAc=6:1), retention time (HPLC*)=2.611 min.

*Reverse phase analytical HPLC conditions:

Column: YMC CombiScreen, Pro C18, CCASS05-05110WT, AS-320-5

Guard column: ODS-A prep guard cartridge, GCAA210110UCA

Solvents: solvent A: acetonitrile with 0.1% TFA (v/v); solvent B: water with 0.1% TFA (v/v)

Conditions:

| Time (min) | 0:00 | 0:01 | 3:45 | 5:00 | 5:05 |
|---|---|---|---|---|---|
| % B | 10.0 | 10.0 | 98.0 | 98.0 | 10.0 |
| Flow (mL/min) | 10.00 | | | | 10.00 |

EXAMPLE 16

Preparation of (2S)-2-{[4-(2-Methoxyethyl)phenoxy]methyl}oxirane

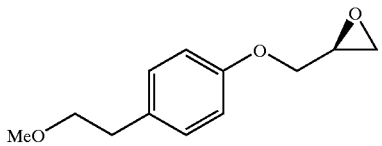

To a solution of 4-(2-methoxyethyl)phenol (42 mg, 0.275 mmol) and (2S)-(+)-glycidyl tosylate (57 mg, 0.25 mmol) in 2 mL of DMF was added 15 mg (0.625 mmol) of sodium hydride (60% in mineral oil). The resulting mixture was allowed to stir for 16 hours at room temperature. The solution was then extracted three times with ethyl acetate, and the organic phase was washed sequentially with sodium hydroxide, water and brine, dried over sodium sulfate, and concentrated in vacuo to provide the product which was used without further purification. m/z 208 [M+H]$^+$.

EXAMPLE 17

Preparation of 5-[(2S)-2-oxiranylmethoxy]isoquinoline

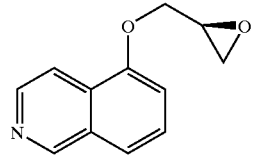

5-Hydroxyisoquinoline (4.0 mmol) was dissolved in 16 mL of N,N-dimethylformamide, followed by the addition of potassium carbonate (1.66 g, 12 mmol) and (S)-(+)-glycidyl nosylate (1.14 g, 1.1 eq). The mixture was heated at 40° C. for 22 hours with stirring. The mixture was then combined with 16 mL of water and 32 mL of ethyl acetate. The organic phase was separated and washed with water (3×16 mL) and brine (10 mL). The organic phase was dried (magnesium sulfate), filtered, and concentrated in vacuo. This procedure generally gave the desired epoxide in over 95% yield which was used without further purification. m/z 203 [M+H]$^+$.

EXAMPLE 18

Preparation of 3-[(2S)-2-oxiranylmethoxy]pyridine

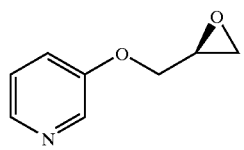

3-Hydroxypyridine (2.5 mmol) was dissolved in 1.0 mL dimethyl sulfoxide and cooled to 15° C. Lithium bis(trimethylsilyl)amide/tetrahydrofuran solution (2.2 mL, 1.0 M) was added, and the mixture was stirred for 5 minutes. (S)-(+)-glycidyl nosylate (2.0 mmol) was added in one portion as a solid, and the resulting mixture was stirred at room temp for 30–45 minutes. Three mL of water was added to quench the reaction, which was then extracted with ethyl acetate (3×10 mL). The organic phase was washed with brine (10 mL), dried (magnesium sulfate), filtered, and concentrated in vacuo. This procedure generally gave the desired epoxide in over 90% yield and the product was used without further purification. m/z 151 [M+H]+.

EXAMPLE 19

Preparation of (2S)-2-{[[(4-ethyl)phenyl]sulfanyl]methyl}oxirane

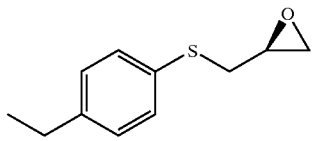

To a suspension of sodium hydride (44 mg of 60% dispersion in mineral oil, 1.1 mmol) in DMF was added slowly a solution of 4-ethylthiophenol (138.2 mg, 1 mmol) in DMF (2.5 ml) at room temperature under argon. Immediately, bubbles were observed and the reaction mixture became clear after 5 minutes and was stirred at room temperature for 30 minutes. This solution was added to a solution of (2S)-(+) glycidyl tosylate (456 mg, 2 mmol) in DMF (2.5 ml) cooled in an ice-water bath via a syringe in 5 minutes under argon. The resultant mixture was stirred at 0–5° C. for 30 minutes and TLC indicated 4-ethylthiophenol has been consumed. The reaction mixture was quenched with saturated ammonium chloride (5 ml), diluted with water (5 ml), and extracted with diethyl ether (3×20 ml). The organic layers were separated and washed with saturated sodium carbonate solution (10 ml), brine (10 ml), and dried over anhydrous magnesium sulfate. Filtration and concentration of the organic phase afforded a colorless oil residue which was chromatographed with hexane/ethyl acetate (=3/1) to obtain colorless oil. (135 mg, 69.6% yield): $^1$H NMR (CDCL$_3$) δ1.19–1.25 (t, 3H), 2.48–2.50 (m, 1H), 2.59–2.66 (m, 2H), 2.75–2.78 (m, 1H), 2.86–2.91 (m, 1H), 3.11–3.16 (m, 2H), 7.12–7.15 (d, 2H), 7.35–738 (d, 2H); GC/MS m/z 194 (M +).

By substituting the appropriate starting materials and utilizing the procedures described for Examples 15–19, the following epoxides intermediates were also prepared and are summarized in Table 2.

TABLE 2

Epoxide Intermediates

| Example No. | Structure | Method of Example No. |
|---|---|---|
| 20 |  | 15, 17 |
| 21 |  | 15, 17 |
| 22 | 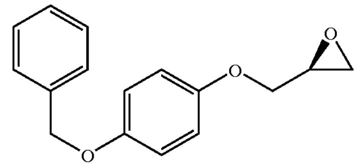 | 15 |
| 23 | 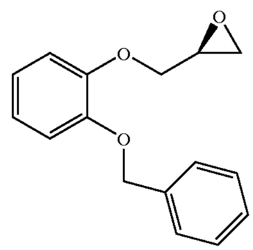 | 15 |
| 24 | 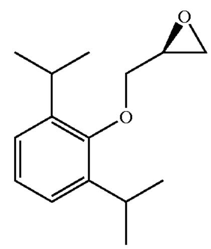 | 16 |
| 25 | 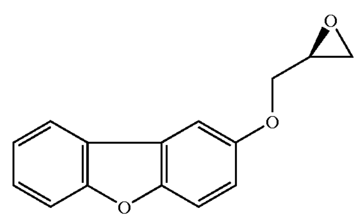 | 17 |
| 26 | 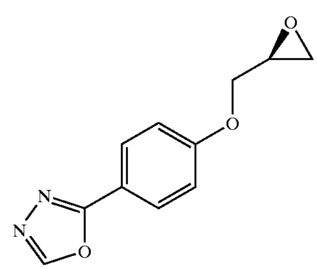 | 17 |
| 27 | 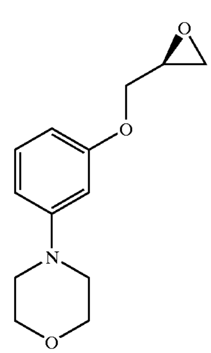 | 17 |

TABLE 2-continued

Epoxide Intermediates

| Example No. | Structure | Method of Example No. |
|---|---|---|
| 28 | 2-methylbenzothiazol-5-yl glycidyl ether | 17 |
| 29 | 4-(1H-pyrrol-1-yl)phenyl glycidyl ether | 17 |
| 30 | 3-(dimethylamino)phenyl glycidyl ether | 17 |
| 31 | 4-(1H-imidazol-1-yl)phenyl glycidyl ether | 17 |
| 32 | 3-(diethylamino)phenyl glycidyl ether | 17 |
| 33 | 2-amino-3-(glycidyloxy)pyridine | 18 |
| 34 | 2-(pyrrolidin-1-ylmethyl)-3-(glycidyloxy)pyridine | 18 |
| 35 | 2-(piperidin-1-ylmethyl)-3-(glycidyloxy)pyridine | 18 |
| 36 | 2-(2,5-dimethyl-1H-pyrrol-1-yl)-3-(glycidyloxy)pyridine | 18 |
| 37 | 2,6-dimethyl-3-(glycidyloxy)pyridine | 18 |

TABLE 2-continued

Epoxide Intermediates

| Example No. | Structure | Method of Example No. |
|---|---|---|
| 38 | (oxiranylmethoxy-pyridin-2-yl)methyl-diethylamine | 18 |
| 39 | 2,6-bis[(dimethylamino)methyl]-3-(oxiranylmethoxy)pyridine | 18 |
| 40 | 2-(2-chlorophenoxymethyl)oxirane | 17 |
| 41 | 2-(3-chlorophenoxymethyl)oxirane | 17 |
| 42 | 2-(4-chlorophenoxymethyl)oxirane | 17 |
| 43 | N-[4-(oxiranylmethoxy)phenyl]phthalimide | 17 |
| 44 | 2-(naphthalen-1-yloxymethyl)oxirane | 17 |
| 45 | 3-(oxiranylmethoxy)-9H-carbazole | 17 |
| 46 | 5-(oxiranylmethoxy)-1H-indole | 17 |
| 47 | 2-(5,6,7,8-tetrahydronaphthalen-2-yloxymethyl)oxirane | 17 |

EXAMPLE 48

Preparation of (2S)-1-(dibenzylamino)-3-phenoxy-2-propanol

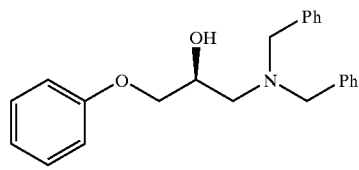

A reaction mixture containing (2S)-2-(phenoxymethyl)oxirane (Example 15, 20.6 mmol, 1.0 eq.) and dibenzylamine (22.7 mmol, 1.1 eq.) in MeOH (100 mL) was heated at reflux overnight. The resulting solution was concentrated in vacuo and the crude product was purified by medium pressure column chromatography (Biotage 40S normal phase silica gel column, hexanes:EtOAc=10:1). The product was obtained as a colorless oil in 88% yield. $MH^+$=348.3, $R_f$=0.42 (hexanes:EtOAc 6:1), retention time (LC-MS)=2.22 min.

By using the appropriately substituted epoxide in place of (2S)-2-(phenoxymethyl)oxirane, the following compounds were prepared and characterized according to method of Example 48.

TABLE 3

Dibenzylamino alcohols

| Example No. | Structure | MS [M + H$^+$] | TLC Rf | LC-MS RT (min) |
|---|---|---|---|---|
| 49 | 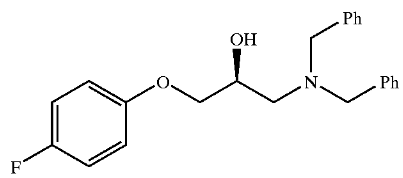 | 366.3 | | 2.29 |
| 50 | 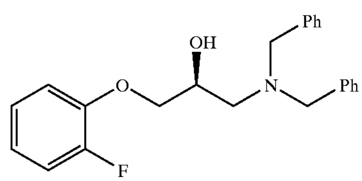 | 366.3 | | 2.32 |
| 51 | 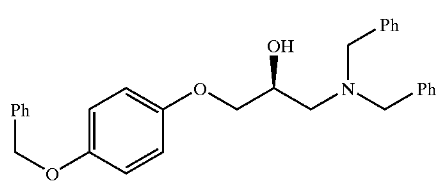 | 454.3 | | 2.68 |
| 52 | 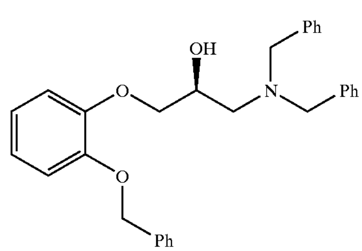 | | 0.54 hexanes:EtOAc 6:1 | |

EXAMPLE 53

Preparation of (2S)-1-amino-3-phenoxy-2-propanol

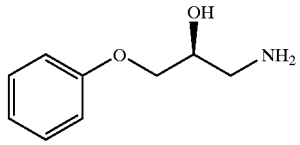

A suspension of (2S)-1-(dibenzylamino)-3-phenoxy-2-propanol (Example 48, 17.6 mmol, 1.0 eq.), palladium hydroxide (20 wt. % Pd (dry basis) on carbon, Pearlman's catalyst, 0.23 g/mmol) in MeOH/EtOAc (157 mL/157 mL) was stirred under hydrogen atmosphere ($H_2$ balloon) for 5 hours. The resulting mixture was filtered through a Celite® pad and the pad was washed with MeOH. The filtrate was concentrated in vacuo to afford a yellow solid that was washed with diethyl ether. The resulting residue was purified by medium pressure column chromatography (Biotage 40S normal phase silica gel column, EtOAc: 2M $NH_3$ in MeOH= 95:5). The product was obtained in 90% yield (2.63). $MH^+$=168.1, $R_f$=0.12 (EtOAc: 2M $NH_3$ in MeOH=5:1), retention time (LC-MS)=0.76 min.

By substituting the appropriate starting materials, the following compounds were prepared and characterized according to the method described for Example 53.

TABLE 4

Amino Alcohol Intermediates

| Example No. | Structure | MS [M + H$^+$] | LC-MS RT (min) |
|---|---|---|---|
| 54 | ![](OH, F-phenoxy, NH2) | 186.1 | 0.78 |
| 55 | ![](OH, o-F-phenoxy, NH2) | 186.1 | 0.78 |
| 56 | ![](OH, HO-phenoxy, NH2) | 184.2 | 0.62 |
| 57 | ![](OH, o-OH-phenoxy, NH2) | 184.2 | 0.63 |

EXAMPLE 58

Preparation of tert-butyl [(2R)-6-iodo-3,4-dihydro-2H-chromen-2-yl]methylcarbamate

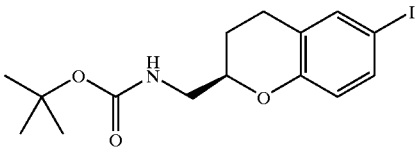

[(2R)-6-iodo-3,4-dihydro-2H-chromen-2-yl] methylamine hydrochloride (Example 10, 3.52 g, 10.83 mmol) was dissolved in 20 mL of THF, and treated with sodium bicarbonate (0.91 g, 10.83 mmol) in 2 mL of water, followed by the addition of di-t-butyldicarbonate (2.36 g, 10.83 mmol). The resulting solution was allowed to stir for 16 hours at room temperature. At this point the solution was concentrated in vacuo and the resulting residue was treated with water and extracted with ethyl acetate. The dried ($Na_2SO_4$) ethyl acetate layers were concentrated in vacuo to obtain 4.02 g of product as a yellowish solid. m/z 389.8 [$M^+$].

EXAMPLE 59

Preparation of tert-butyl(dimethyl)silyl [(2R)-6-iodo-3,4-dihydro-2H-chromen-2-yl]methyl ether

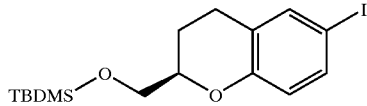

A reaction mixture containing [(2R)-6-iodo-3,4-dihydro-2H-chromen-2-yl]methanol (Example 8, 5 g, 17.2 mmol, 1.0 eq), tert-butyldimethylsilyl chloride (20.6 mmol, 1.2 eq), and imidazole (43 mmol, 2.5 eq) in anhydrous DMF (35 mL) was stirred at 27° C. overnight. The resulting mixture was then cooled to room temperature, poured into water, and extracted with diethyl ether. The organic extract was washed with water, brine, dried over anhydrous sodium sulfate, concentrated, and purified by medium pressure column chromatography (Biotage 40S normal phase silica gel column, providing the product in 79% yield; M/z 405 [$MH^-$].

EXAMPLE 60

Preparation of tert-butyl(dimethyl)silyl [(2R)-6-(4,4,5,5-tetramethyl-1,3,2-dioxaborolan-2-yl)-3,4-dihydro-2H-chromen-2-yl]methyl ether

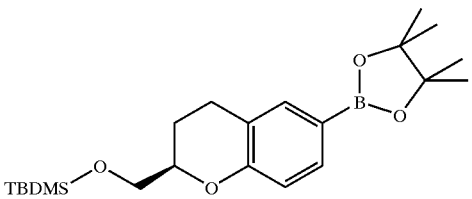

Argon was bubbled through a solution of tert-butyl (dimethyl)silyl [(2R)-6-iodo-3,4-dihydro-2H-chromen-2-yl]methyl ether (Example 59, 11.1 mmol, 1.0 eq.) in dioxane (45 mL) for 10 minutes before Pd(dppf)Cl$_2$ (0.306 mmol, 0.03 eq.), triethylamine (33.4 mmol, 3.0 eq.), and 4,4,5,5-tetramethyl-1,3,2-dioxaborolane (17.8 mmol, 1.6 eq.) were added. The resulting reaction mixture was stirred at 80° C. overnight. The resulting reaction mixture was filtered through a Celite pad. The filtrate was concentrated and purified by medium pressure column chromatography (Biotage 40S normal phase silica gel column, hexanes:EtOAc=10:1). The product was obtained as a pale brown waxy solid in 94% yield. MH$^+$=405.3, retention time (LC-MS) =4.79 min.

EXAMPLE 61

Preparation of Methyl 4-(4,4,5.5-tetramethyl-1,3,2-dioxaborolan-2-yl)benzoate

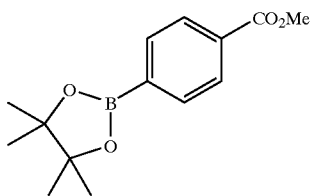

A solution of methyl 4-iodobenzoate (2.00 g, 7.63 mmol) in 30 mL of dioxane was degassed with argon for 10 minutes. Then, Pd(dppf)Cl$_2$ (171 mg, 3 mol %), triethylamine (3.27 mL), and pinacolborane (1.47 g, 11.45 mmol) were added. The resulting solution was stirred at 85° C. for 16 hours. The mixture was allowed to cool to ambient temperature, filtered through a pad of Celite, and concentrated in vacuo to obtain 3.97 g of product which was used without further purification. m/z 263 [M+H]$^+$.

EXAMPLE 62

Preparation of Methyl 4-[(2R)-2-(hydroxymethyl)-3,4-dihydro-2H-chromen-6-yl]benzoate

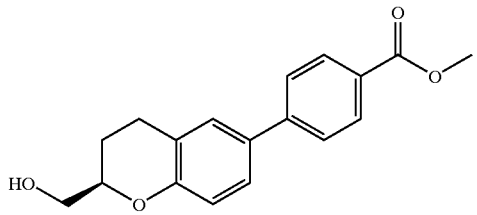

Method (1)

Argon was bubbled through a solution of tert-butyl (dimethyl)silyl [(2R)-6-(4,4,5,5-tetramethyl-1,3,2-dioxaborolan-2-yl)-3,4-dihydro-2H-chromen-2-yl]methyl ether (Example 60, 2.47 mmol, 1.0 eq.) in toluene (60 mL) for 10 minutes. Next, Pd(dppf)Cl$_2$ (0.164 mmol, 0.07 eq.) and methyl 4-iodobenzoate (3.71 mmol, 1.5 eq.) were added in a single portion. The resulting reaction mixture was degassed with argon for an additional 5 minutes before aqueous Na$_2$CO$_3$ (2 M, 26 mmol, 10.5 eq.) was added, and the solution was heated at 85° C. overnight. The product mixture was allowed to cool to room temperature, water was added and the two-phase mixture was extracted with ethyl acetate. The combined organic extracts were dried over anhydrous sodium sulfate, concentrated, and purified by medium pressure column chromatography (Biotage 40S normal phase silica gel column, hexane:ethyl acetate 10:1). The purified product was dissolved in THF (10 mL) and tetrabutylammonium fluoride (1M, 5 mL) was added in a single portion. The resulting mixture was stirred at room temperature for 1 hour. The solvents were evaporated and the resulting residue was purified by medium pressure column chromatography (Biotage 40S normal phase silica gel column, hexanes:EtOAc=5:1 to 2:1). The product was obtained as a white solid in yield of 46% (two step yield). MH$^+$=299.2, retention time (LC-MS)=2.79 min.

Method (2)

To a 5-L 3-necked round-bottomed flask were charged 4-methoxycarbonyl phenylboronic acid (72.0 g, 0.4 mol), potassium carbonate (124.4 g, 0.9 mol), and water (900 mL) to obtain a suspension. To this suspension was then added a solution of [(2R)-6-iodo-3,4-dihydro-2H-chromen-2-yl]methanol (105.5 g, 0.36 mol) in acetone (720 mL). The resultant mixture became a near homogeneous solution (internal temperature rose from 20 to 28° C.). Palladium acetate (1.5 g, 0.0067 mol) was then added in one portion. The reaction mixture was then heated at 65° C. under argon for 2 hours. It turned into a suspension. Heating was removed and the reaction was allowed to cool to room temperature. The solid (metallic color) was then collected by filtration and dried by suction. The crude was then dissolved in chloroform (2 L) and filtered through a pad of Celite (100 g) under vacuum slowly to remove palladium. Removal of solvent in vacuo afforded the desired compound as a white solid (90 g, 84% yield): $^1$H NMR (CDCl$_3$) δ1.82–2.12 (m, 3 H), 2.80–3.02 (m, 2H), 3.75–3.90 (m, 2H), 3.92 (s, 3H), 4.20 (m, 1H), 6.91 (d, J=8.1 Hz, 1H), 7.33 (s, 1H), 7.37 (dd, J=8.1, 2.7 Hz, 1H), 7.60 (d, J=9 Hz, 2H), 8.06 (d, J=8.7 Hz, 2H).

EXAMPLE 63

Preparation of Methyl 3-[(2R)-2-(hydroxymethyl)-3,4-dihydro-2H-chromen-6-yl]benzoate

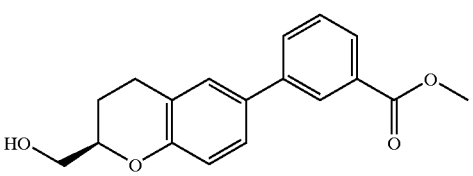

Using essentially the same procedure as Example 62, Method (1), and substituting appropriate starting materials, methyl 3-[(2R)-2-(hydroxymethyl)-3,4-dihydro-2H-chromen-6-yl]benzoate was prepared in yield of 68% (two steps). MH$^+$=313.1, retention time (LC-MS)=3.00 min.

EXAMPLE 64

Preparation of Methyl 4-((2R)-2-{[(tert-butoxycarbonyl)amino]methyl}-3,4-dihydro-2H-chromen-6-yl) benzoate

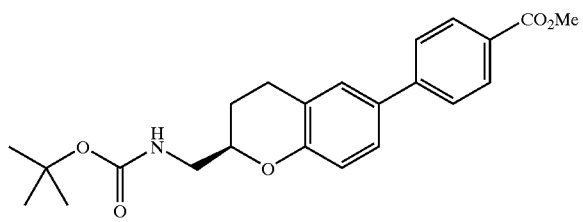

A solution of methyl 4-(4,4,5,5-tetramethyl-1,3,2-dioxaborolan-2-yl)benzoate (1.67 g, 6.36 mmol) in toluene (130 mL) and 1,4-dioxane (27 mL) was degassed with argon for 10 minutes. tert-Butyl [(2R)-6-iodo-3,4-dihydro-2H-chromen-2-yl]methylcarbamate (1.65 g) and Pd(dppf)Cl$_2$ (265 mg, 3 mol %) were then added, and the solution was degassed with argon for an additional 5 minutes. Finally, 2M aqueous sodium carbonate (26.5 mL) was added and the solution was stirred at 85° C. for 16 hours. This mixture was then cooled to ambient temperature, filtered through a pad of Celite, and concentrated in vacuo. The product was then purified by Biotage (100% methylene chloride to 3% MeOH:methylene chloride) to obtain 1.40 g of product. m/z 397.9 [M+].

EXAMPLE 65

Preparation of Methyl 4-[(2R)-2-(aminomethyl)-3,4-dihydro-2H-chromen-6-yl]benzoate

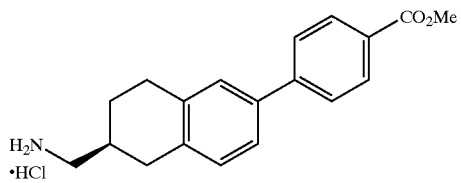

To a solution of methyl 4-((2R)-2-{[(tert-butoxycarbonyl)amino]methyl}-3,4-dihydro-2H-chromen-6-yl) benzoate (Example 64, 0.94 g, 2.37 mmol) in 1,4-dioxane (5 mL) was added 4 M hydrochloric acid (1 mL) in 1,4-dioxane dropwise. The resulting solution was allowed to stir at room temperature for 16 hours, followed by concentration in vacuo. At this point, diethyl ether was added and the solid was collected to provide 587 mg of (V) as a white solid. m/z 298.2 [MH+].

EXAMPLE 66

Preparation of Methyl 4-[(2R)-2-formyl-3,4-dihydro-2H-chromen-6-yl]benzoate

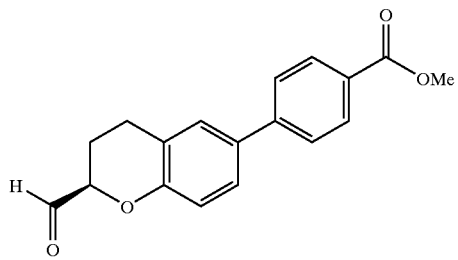

To a solution of dimethyl sulfoxide (33 mg, 0.425 mmol) in methylene chloride (2 mL) at −78° C., was added 0.14 mL of 2 M oxalyl chloride (0.272 mmol). After the solution had stirred at this temperature for 10 minutes, a solution of methyl 4-[(2R)-2-(hydroxymethyl)-3,4-dihydro-2H-chromen-6-yl]benzoate (50 mg, 0.17 mmol) in methylene chloride (2 mL) was added dropwise and the resulting mixture was stirred at −78° C. for an additional 1.6 hours. At this time, triethylamine (0.14 mL, 1.02 mmol) was added to the mixture slowly, and then it was allowed to warm to room temperature over 15 minutes. The solution of desired product was used directly in following steps.

EXAMPLE 67

Preparation of Ethyl 2-chloro-3-oxo-3-phenylpropanoate

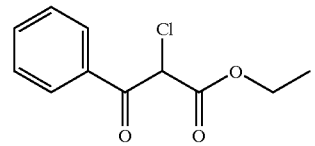

A solution of sulfuryl chloride (12.4 mmol) in toluene (5 mL) was added dropwise via an additional funnel to a solution of ethyl isobutyrylacetate (12.4 mmol) in toluene (20 mL) over 5 minutes at room temperature. The resulting mixture was stirred at room temperature overnight. Water was added slowly and resulting two-phase mixture was basified with saturated NaHCO$_3$ and extracted with ethyl acetate. The combined organic extracts were washed with brine, dried over anhydrous sodium sulfate, and evaporated to afford 2.2 g (84%) of product as a pale yellow oil: MH+=227.0, retention time (LC-MS)=2.77 min.

EXAMPLE 68

Preparation of Ethyl 2-chloro-4-methyl-3-oxopentanoate

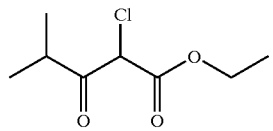

Utilizing the method described for Example 67, the product was obtained in 67% yield (crude). MH+=193.0, retention time (LC-MS)=2.45 min.

EXAMPLE 69

Preparation of Methyl 2-amino-5-phenyl-1,3-thiazole-4-carboxylate

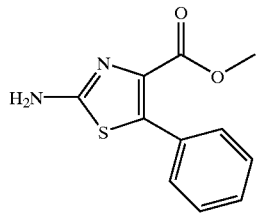

A solution of NaOMe (25 wt %) in MeOH (13.4 mmol) was added to a solution of methyl dichloroacetate (13.4 mmol) and benzaldehyde (14.8 mmol, 1.1 eq.) in diethyl ether (8 mL) dropwise at 0° C. The reaction mixture was stirred at 0° C. for 1 hour before diethyl ether and brine were added. The organic layer was separated, dried over anhydrous sodium sulfate, and evaporated to give a crude material which was dissolved in MeOH (16 mL) containing thiourea (11.4 mmol, 0.85 eq.). The resulting reaction mixture was heated to reflux for 18 hours. The crude product mixture was concentrated in vacuo, neutralized with 18M-$NH_4OH$ at which time the product precipitated as a white solid. The product was washed with $CH_2Cl_2$ (2×), water and was collected by filtration to afford 1.88 g (70%) of product; $MH^+$=235.1, $R_f$=0.18 (Hexanes:EtOAc=1:1), retention time (LC-MS)=1.86 min.

EXAMPLE 70

Preparation of methyl 2-amino-5-isopropyl-1,3-thiazole-4-carboxylate

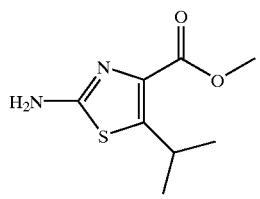

Example 70 was prepared according to method of Example 69 in 88% yield. $MH^+$=201.0, retention time (LC-MS)=1.48 min.

EXAMPLE 71

Preparation of ethyl 2-amino-4-phenyl-1,3-thiazole-5-carboxylate

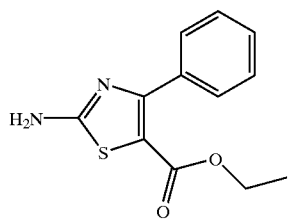

A solution of ethyl 2-chloro-3-oxo-3-phenylpropanoate (9.73 mmol) and thiourea (9.73 mmol) in EtOH (25 mL) was heated at reflux overnight. The resulting mixture was concentrated in vacuo, neutralized with 18M-$NH_4OH$, and extracted with $CH_2Cl_2$. The organic phase was washed with brine, dried over anhydrous sodium sulfate, and concentrated to afford a yellow solid that was washed with MeOH (3 mL) and dried to afford the product in 89% yield as a pale yellow solid. $MH^+$=249.1, $R_f$=0.29 (Hexanes:EtOAc=1:1). $MH^+$=249.1, retention time (LC-MS)=2.37 min.

EXAMPLE 72

Preparation of ethyl 2-amino-4-isopropyl-1,3-thiazole-5-carboxylate

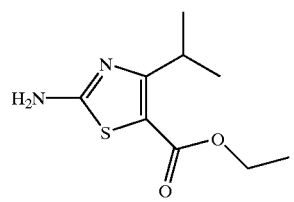

The title compound was prepared according to method of Example 71 in 65% yield. $MH^+$=215.1, $R_f$=0.66 (hexanes:EtOAc=1:1), retention time (LC-MS)=1.98 min.

EXAMPLE 73

Preparation of Ethyl 5-phenyl-1,3-oxazole-4-carboxylate

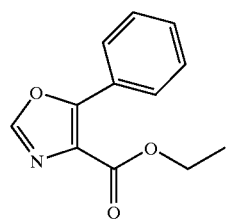

To a mixture of ethyl isocyanoacetate (8.74 mmol) and 1,8-diazabicyclo(5.4.0)undec-7-ene (8.84 mmol) in THF (12 mL) was added a solution of benzoic anhydride (8.84 mmol) in THF (2 mL) at 10° C. with stirring. The resulting mixture was maintained with vigorous stirring for 18 hours at room temperature. The solvent was evaporated to afford a residue that was partitioned between EtOAc and water. The organic extract was dried over anhydrous sodium sulfate and concentrated to afford an amber oil which was purified by medium pressure column chromatography (Biotage 40S normal phase silica gel column, hexanes:EtOAc=6:1 to 4:1 to 2:1). The product was obtained as a clear oil in 42%. MH+=218.1, retention time (LC-MS)=2.52 min.

EXAMPLE 74

Preparation of Methyl 2-bromo-5-phenyl-1,3-thiazole-4-carboxylate

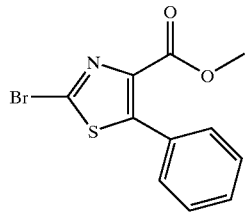

To a dark brown solution of copper(II) bromide (3.85 mmol, 3 eq.) in acetonitrile (5 mL) in a two-neck round-bottomed flask equipped with a condenser was added tert-butyl nitrite (1.92 mmol, 1.5 eq.) slowly at room temperature. The resulting mixture was heated to 60° C. at which time a suspension of methyl 2-amino-5-phenyl-1,3-thiazole-4-carboxylate (1.28 mmol) in acetonitrile (7 mL) was added dropwise. The resulting reaction mixture was heated at 60° C. for 3 hours, allowed to cool to room temperature, poured onto 1M NaOH aqueous and extracted with EtOAc. The organic extracts were dried over anhydrous sodium sulfate, concentrated and purified by medium pressure column chromatography (Biotage 40S normal phase silica gel column, hexanes:EtOAc=5:1). The product was obtained as a pale yellow oil in 88%. MH+=298.0, $R_f$=0.74 (hexanes:EtOAc= 2:1), retention time (LC-MS)=3.01 min.

EXAMPLES 75–77

Preparation of Methyl 2-bromo-5-isopropyl-1,3-thiazole-4-carboxylate, ethyl 2-bromo4-phenyl-1,3-thiazole-5-carboxylate, and ethyl 2-bromo-4-isopropyl-1,3-thiazole-5-carboxylate Using essentially the same procedure and substituting the appropriate starting materials, the following were prepared and characterized according to method of Example 74:

TABLE 5

Bromo-substituted Heterocycles

| Example No. | Structure | MS [M + H+] | TLC Rf | LC-MS RT (min) |
|---|---|---|---|---|
| 75 | 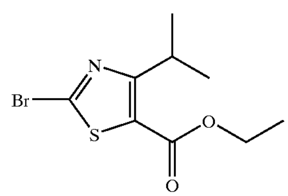 | 264.0 | 0.51 hexanes:EtOAc 6:1 | 2.83 |
| 76 | 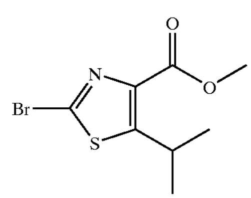 | 312.1 | 0.65 hexanes:EtOAc 6:1 | 3.46 |
| 77 | 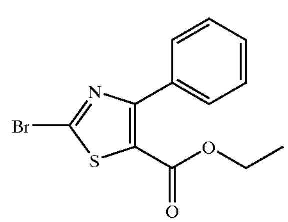 | 278.2 | 0.74 hexanes:EtOAc 6:1 | 3.54 |

EXAMPLE 78

Preparation of Ethyl 2-iodo-5-phenyl-1,3-oxazole-4-carboxylate

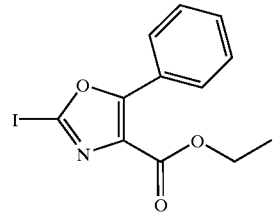

To a solution of ethyl 5-phenyl-1,3-oxazole-4-carboxylate (Example 73, 0.921 mmol, 1 eq.) in THF (7 mL) at −78° C. was added a solution of lithium (trimethylsilyl)amide in THF (1 M in THF, 1.11 mmol, 1.2 eq.) dropwise by syringe. The resulting solution was stirred at −78° C. for 1 hour at which time a solution of iodine (1.38 mmol, 1.5 eq. in 2 mL of THF) was added dropwise by a syringe. The reaction mixture was allowed to warm to room temperature and stirred at this temperature for 1.5 hours. The resulting solution was poured onto 10% aqueous $NaS_2O_3$ (15 mL) and extracted with ethyl acetate. The organic extracts were washed with brine, dried over anhydrous sodium sulfate, concentrated in vacuo and purified by medium pressure column chromatography (Biotage 40S normal phase silica gel column, hexanes:EtOAc=9:1). The product was obtained as a pale yellow solid in 82% yield. $MH^+$=344.0, $R_f$=0.31 (hexanes:EtOAc=6:1), retention time (LC-MS)=3.01 min.

EXAMPLE 79

Preparation of (2R)-N-[(2S)-2-hydroxy-3-phenoxypropyl]-6-iodo-3,4-dihydro-2H-chromene-2-carboxamide

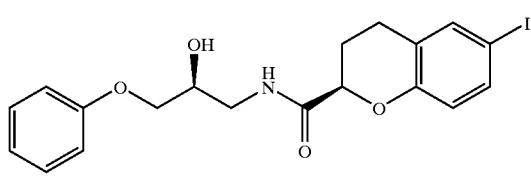

A solution containing (2S)-1-amino-3-phenoxy-2-propanol (Example 53, 11.97 mmol, 1.0 eq.), (2R)-6-iodo-3,4-dihydro-2H-chromene-2-carboxylic acid (Example 7, 11.97 mmol, 1.0 eq.), 1-(3-dimethylaminopropyl)-3-ethylcarbodiimide hydrochloride (23.98 mmol, 2.0 eq.), 1-hydroxybenzotriazole hydrate (23.94 mmol, 2.0 eq.), and triethylamine (23.94 mmol, 2.0 eq.) in $CH_2Cl_2$ (200 mL) was stirred at room temperature for 3 hours. To the resulting solution was added water and two-phase mixture was extracted with $CH_2Cl_2$. The organic extracts were washed with water and brine, dried over anhydrous sodium sulfate, concentrated and purified by medium pressure column chromatography (Biotage 40S normal phase silica gel column, hexanes:EtOAc=2:1). The product was obtained as a white solid in 77% yield. $MH^+$=454.1, retention time (LC-MS)=3.03 min.

EXAMPLE 80

Preparation of (2S)-1-({[(2R)-6-iodo-3,4-dihydro-2H-chromen-2-yl]methyl}amino)-3-phenoxy-2-propanol

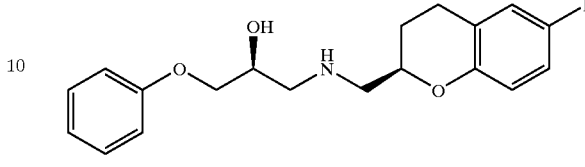

To a solution containing (2R)-N-[(2S)-2-hydroxy-3-phenoxypropyl]-6-iodo-3,4-dihydro-2H-chromene-2-carboxamide (Example 79, 9.204 mmol, 1 eq.) in THF (140 mL) at room temperature was slowly added borane-methyl sulfide complex (2 M in THF, 46.07 mmol, 5.0 eq.). After completion of addition, reaction solution was heated to reflux, maintained at that temperature for 2 hours, and then cooled to room temperature. The resulting solution was quenched with EtOH (5 mL) dropwise, then with 2 M HCl (20 mL) slowly. The resulting mixture was heated at reflux for 1 hour and was then allowed to cool to room temperature. This solution was basified with 1 N NaOH and extracted with ethyl acetate. The organic extract was washed with brine, dried over anhydrous sodium sulfate, and concentrated in vacuo. The resulting residue was dissolved in MeOH and EtOAc and filtered. The filtrate was concentrated and dried in vacuo to afford the product as a white solid in 99% yield. $MH^+$=440.2, retention time (LC-MS)=2.24 min.

EXAMPLE 81

Preparation of tert-butyl (2S)-2-hydroxy-3-phenoxypropyl{[(2R)-6-iodo-3,4-dihydro-2H-chromen-2-yl]methyl}carbamate

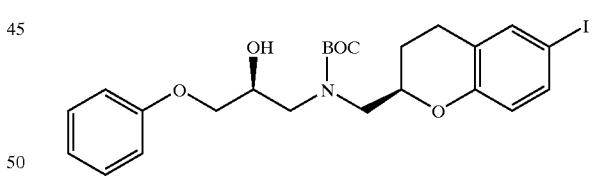

A reaction mixture containing (2S)-1-({[(2R)-6-iodo-3,4-dihydro-2H-chromen-2-yl]methyl}amino)-3-phenoxy-2-propanol (Example 80, 8.905 mmol, 1.0 eq.) and di-tert-butyl dicarbonate (9.3506 mmol, 1.05 eq.) in THF (90 mL) was stirred at room temperature for 5 hours. To this solution was added water and the resulting two-phase mixture was extracted with ethyl acetate. The organic extract was washed with brine, dried over anhydrous sodium sulfate, concentrated and purified by medium pressure column chromatography (Biotage 40S normal phase silica gel column, hexanes:EtOAc=3.5:1). The product was obtained as a colorless oil in yield of 97%. $MH^+$=539.9, retention time (LC-MS)=3.99 min.

EXAMPLE 82

Preparation of tert-butyl (2S)-2-{[tert-butyl (dimethyl)silyl]oxy}-3-phenoxypropyl{[(2R)-6-iodo-3,4-dihydro-2H-chromen-2yl]methyl}carbamate

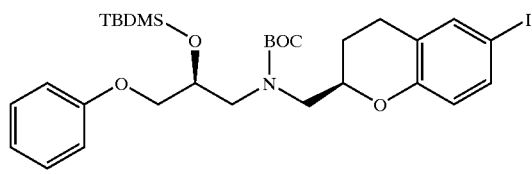

A reaction mixture containing tert-butyl (2S)-2-hydroxy-3-phenoxypropyl{[(2R)-6-iodo-3,4-dihydro-2H-chromen-2-yl]methyl}carbamate (Example 81, 8.625 mmol, 1.0 eq.), tert-butyldimethylsilyl chloride (10.35 mmol, 1.2 eq.), and imidazole (21.5625 mmol, 2.5 eq.) in anhydrous DMF (18 mL) was stirred at 27° C. overnight. The resulting mixture was then cooled to room temperature, poured into water, and extracted with diethyl ether. The organic extract was washed with water, brine, dried over anhydrous sodium sulfate, concentrated, and purified by medium pressure column chromatography (Biotage 40S normal phase silica gel column, hexanes:EtOAc=100:5). The product was obtained as a colorless oil in 97% yield. MH$^+$=654.0, retention time (LC-MS)=5.29 min.

EXAMPLE 83

Preparation of tert-butyl (2S)-2-{[tert-butyl (dimethyl)silyl]oxy}-3-phenoxypropyl{[(2R)-6-(4,4,5,5-tetramethyl-1,3,2-dioxaborolan-2-yl)-3,4-dihydro-2H-chromen-2-yl]methyl}carbamate

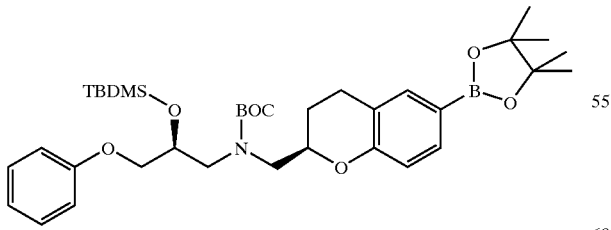

The compound was prepared from Example 82 in 75% yield according to the method of Example 60. MH$^+$=653.9, retention time (LC-MS)=5.30 min.

EXAMPLE 84

Preparation of Methyl 4-[(2R)-2-({[(2S)-2-hydroxy-3-phenoxypropyl]amino}methyl)-3,4-dihydro-2H-chromen-6-yl]benzoate

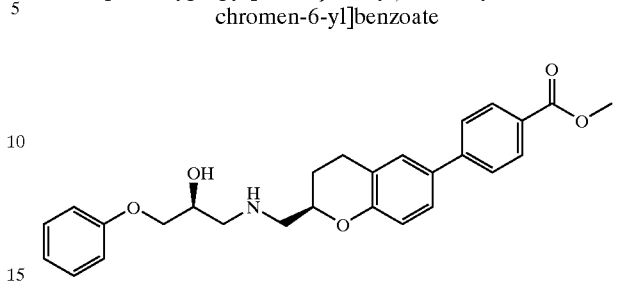

To a solution of anhydrous DMSO (0.839 mmol, 2.5 eq.) in CH$_2$Cl$_2$ (4 mL) at −78° C. was added oxalyl chloride (2M in CH$_2$Cl$_2$, 0.536 mmol, 1.6 eq.) dropwise by syringe. The resulting mixture was stirred at −78° C. for 10 minutes before a solution of methyl 4-[(2R)-2-(hydroxymethyl)-3,4-dihydro-2H-chromen-6-yl]benzoate (Example 62, 0.335 mmol, 1.0 eq.) in CH$_2$Cl$_2$ (4 mL) was added very slowly by syringe. The resulting reaction mixture was stirred at −78° C. for 2 hours, at which time triethylamine (2.01 mmol, 6.0 eq.) was added. The cooling bath was removed and the reaction mixture was allowed to warm to room temperature (about 10 minutes). To the resulting crude aldehyde was added (2S)-1-amino-3-phenoxy-2-propanol (0.67 mmol, 2.0 eq.) in a single portion followed by acetic acid (6.03 mmol, 18.0 eq.). The resulting mixture was stirred for 5 minutes before sodium triacetoxyborohydride (1.005 mmol, 3.0 eq.) was added in a single portion. The reaction mixture was stirred at room temperature for 3 hours. The triacetoxyborohydride was quenched by the addition of 1N NaOH until the pH reached 9–10. The resulting two-phase mixture was extracted with CH$_2$Cl$_2$. The organic extracts were dried over sodium sulfate, concentrated and purified by medium pressure column chromatography (Biotage 40S normal phase silica gel column, CH$_2$Cl$_2$ to CH$_2$Cl$_2$:MeOH=100:3). The product was obtained as a pale yellow solid in 99% yield (two steps). MH$^+$=448.3, retention time (LC-MS)=2.46 min.

EXAMPLE 85

Preparation of N-benzyl-N-{[(2R)-6-bromo-3,4-dihydro-2H-chromen-2-yl]methyl}amine

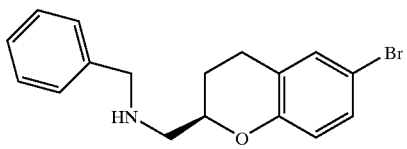

In a 500-mL round bottom flask, N-benzyl[(2R)-3,4-dihydro-2H-chromen-2-yl]methanamine hydrobromide (33.4 g, 0.1 mole, 1.0 eq.) was suspended in 240 mL of acetic acid. The suspension was cooled to 16° C., then bromine (16 g, 0.1 mole, 1.0 eq.) was added over 20 minutes, maintaining the reaction temperature between 15–16° C. After 60 minutes, an HPLC analysis indicated the reaction was complete. The reaction mixture was then stirred for 30 minutes at room temperature, and the product was collected by filtration. The light gray moist product was suspended in dichloromethane (200 mL) and to this suspension was added 0.5M NaHCO$_3$ (350 mL). Foaming ensued and the suspension became a bi-phasic solution. The aqueous phase was separated (14.5 L; pH=8) and the organic phase was washed with 50 mL water. The phases were separated and the organic phase concentrated in vacuo at 45° C. to yield 31.6 g of N-benzyl-N-{[(2R)-6-bromo-3,4-dihydro-2H-chromen-2-yl]methyl}amine. NMR (DMSO-d$_6$) δ1.56 (m, 1H), 2.02 (m, 1H), 2.25 (bs, 1H), 2.73 (m, 4H), 3.75 (s, 2H), 4.05 (m, 1H), 6.70 (d, J=8.8 Hz, 1H), 7.25–7.40 (m, 7H); MS (El): m/z 232 (MH+), 234 (M+2).

EXAMPLE 86

(2S)-1-(benzyl{[(2R)-6-bromo-3,4-dihydro-2H-chromen-2-yl]methyl}amino)-3-phenoxy-2propanol-hydrobromide

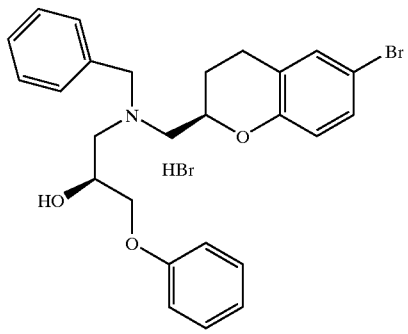

In a 500-mL round bottom flask, Example 85 (29.5 g, 0.089 mole, 1.0 eq.) and (2S)-2-(phenoxymethyl)oxirane (Example 15, Sharpless, et al., *J. Org. Chem.* 1989, 54, pp 1295–1304.) (13.3 g, 0.089 mole, 1.0 eq.) were dissolved in 45 mL isopropanol. To this stirred solution was added K$_2$CO$_3$ (9 g, 0.107 moles, 1.2 eq.). The reaction mixture was then heated to reflux (inner reflux temperature=85° C.; maximum mantle temperature=100° C.) for 7 hours when an HPLC analysis indicated the reaction to be complete. Isopropanol (50 mL) was added, the reaction filtered, and the filter cake was washed with an additional 120 mL of isopropanol. The organic filtrate was transferred to a 500-mL vessel to which was added 48% hydrobromic acid (18 mL) (no temperature increase was noted). The suspension was stirred for 60 minutes as the mixture was heated at reflux for 2.5 hours (the mixture did not form a complete solution; inner temperature=69° C.; mantle temperature=100° C.). The mixture was cooled to room temperature over a 15-hour period. The crystalline product was collected by filtration and dried to yield 45.8g of (2S)-1-(benzyl{[(2R)-6-bromo-3,4-dihydro-2H-chromen-2-yl]methyl}amino)-3-phenoxy-2-propanol hydrobromide. NMR (DMSO-d$_6$) δ1.67 (m, 1H), 2.04 (m, 1H,), 2.80 (m, 2H), 3.34 (m, 1H), 3.55(m, 3, CH), 3.96 (br s, 2H), 4.45 (m, 1H), 4.67 (m, 3H), 5.95 (bs, 1H), 6.90 (m, 4H, Ar,), 7.27 (m, 4, ArH), 7.45 (m, 3H, ArH), 7.66 (m, 2H); MS (EI): m/z 483 (MH+). HPLC: >98% de and 97% pure by Chiralpak OD column using racemic standard as reference.

EXAMPLE 87

Preparation of (2S)-N-{[(2R)-6-bromo-3,4-dihydro-2H-chromen-2-yl]methyl}-2-{[(1,1-dimethylethyl)(dimethyl)silyl]oxy}-N-(phenylmethyl)-3-(phenyloxy)-1-propanamine

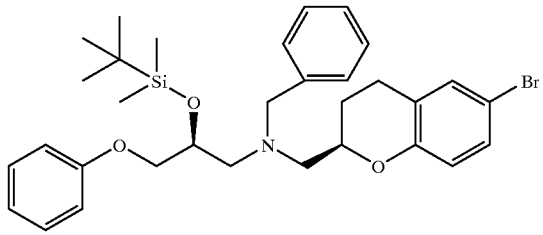

The compound of Example 86 (5.0 g, 10.4 mmol) and imidazole (1.06 g, 15.6 mmol, 1.5 eq.) were dissolved in dichloromethane. tert-Butyldimethylsilylchloride (2.03 g, 13.5 mmol, 1,3 eq.) was added, and the mixture was stirred for 15 hours. Solids were removed by filtration, and the filtrate was concentrated in vacuo. The resulting oil was purified by flash chromatography on silica gel eluted with 90:10 hexanes/ethyl acetate. The title compound was obtained as a yellow oil (5.3 g, 85%): $^1$H NMR (300 MHz, CDCl$_3$) δ7.30–7.26 (m, 5 H), 7.25–7.20 (m, 3 H), 7.09 (s, 1 H), 6.91 (t, 1 H), 6.80 (d, 2 H), 6.63 (d, 1 H), 4.07–4.00 (m, 2 H), 3.81 (s, 2 H), 3.73 (dd, 1 H), 2.88–2.77 (m, 2 H), 2.64–2.56 (m, 4 H), 1.96–1.90 (m, 1 H), 1.61–1.55 (m, 1 H), 0.85 (s, 9 H), 0.07 (s, 3 H), 0.04 (s, 3 H); MS m/z 596.3 (MH+).

EXAMPLE 88

Preparation of (2S)-N-{[(2R)-6-(4,4,5,5-tetramethyl-1,3,2-dioxaborolan-2-yl)-3,4-dihydro-2H-chromen-2-yl]methyl}-2-{[(1,1-dimethylethyl)(dimethyl)silyl]oxy}-N-(phenylmethyl)-3-(phenyloxy)-1-propanamine

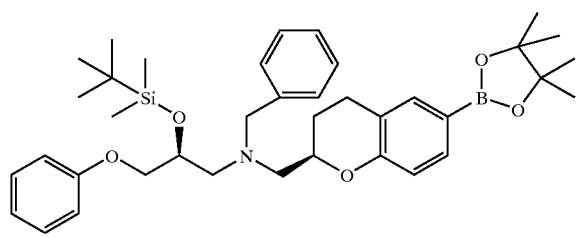

(2S)-N-{[(2R)-6-Bromo-3,4-dihydro-2H-chromen-2-yl]methyl}-2-{[(1,1-dimethylethyl)(dimethyl)silyl]oxy}-N-(phenylmethyl)-3-(phenyloxy)-1-propanamine (Example 87, 5.3 g, 8.9 mmol), bis(pinacolato)diboron (2.5 g, 9.8 mmol, 1.1 eq.), and potassium acetate (2.62 g, 26.7 mmol, 3.0 eq.) were dissolved in anhydrous methyl sulfoxide. Argon gas was bubbled through the solution for 5 minutes before Pd(dppf)Cl$_2$ (0.22 g, 0.3 mmol, 0.03 equivalent) was added. The solution was heated at 80° C. for 18 hours, cooled, and filtered through a plug of silica gel with ethyl acetate. The filtrate was concentrated in vacuo, and the resulting residue was purified by flash chromatography on silica gel eluted with 95:5 hexanes/ethyl acetate. The title compound was collected as a yellow oil (3.5 g, 60%): $^1$H NMR (300 MHz, CDCl$_3$) δ7.51–7.47 (m, 2 H), 7.33–7.26 (m, 4 H), 7.23–7.20 (m, 3 H), 6.90 (t, 1 H), 6.82–6.74 (m, 3 H), 4.16–4.06 (m, 2 H), 3.80 (s, 2 H), 3.73 (dd, 1 H), 2.90–2.76 (m, 2 H), 2.71–2.64 (m, 4 H), 1.98–1.93 (m, 1 H), 1.61–1.56 (m, 1 H), 1.31 (s, 12 H), 0.85 (s, 9 H), 0.07 (s, 3 H), 0.04 (s, 3 H); MS m/z 644.1 (MH$^+$).

EXAMPLE 89

Preparation of 4-((2R)-2-{[[(2S)-2-{[(1,1-dimethylethyl)(dimethyl)silyl]oxy}-3-(phenyloxy)propyl](phenylmethyl)amino]methyl}-3,4-dihydro-2H-chromen-6-yl)-2-pyridinecarboxamide

Argon was bubbled through a mixture of (2S)-N-{[(2R)-6-(4,4,5,5-tetramethyl-1,3,2-dioxaborolan-2-yl)-3,4-dihydro-2H-chromen-2-yl]methyl}-2-{[(1,1-dimethylethyl)(dimethyl)silyl]oxy}-N-(phenylmethyl)-3-(phenyloxy)-1-propanamine (Example 88, 100 mg, 0.16 mmol) and 4-chloro-2-pyridinecarboxamide in toluene (1 mL), ethanol (1 mL), and 2M aqueous sodium carbonate (1 mL) for 10 minutes. Triphenylphosphine (4 mg, 0.016 mmol, 0.1 eq.) and palladium (II) acetate (1.0 mg, 0.004 mmol, 0.025 eq.) were added, and the mixture was stirred vigorously under argon at 85° C. overnight. The reaction was cooled and filtered through a pad of Celite® with the aid of ethyl acetate. The filtrate was concentrated in vacuo to remove excess solvents, and the resulting oil was purified by flash chromatography on silica gel eluted on a gradient from 75:25 to 25:75 hexanes/ethyl acetate. The title compound was obtained as a pale yellow oil (45 mg, 44%): $^1$H NMR (300 MHz, acetone-d$_6$) δ8.57 (d, 1 H), 8.31 (d, 1 H), 7.96 (broad s, 1 H), 7.76 (dd, 1 H), 7.56–7.53 (m, 2 H), 7.45–7.41 (m, 2 H), 7.34–7.21 (m, 5 H), 6.91–6.86 (m, 4H), 6.80 (broad s, 1 H), 4.35–4.30 (m, 1 H), 4.26–4.18 (m, 2 H), 3.93–3.77 (m, 3 H), 2.98–2.87 (m, 4 H), 2.15–2.08 (m, 1 H), 1.73–1.59 (m, 1 H), 1,30–1.25 (m, 1 H), 0.88 (s, 9 H), 0.12 (s, 3 H), 0.08 (s, 3 H); MS m/z 638.4 (MH$^+$).

EXAMPLE 90

Preparation of 4-((2R)-2-{[[(2S)-2-{[(1,1-dimethylethyl)(dimethyl)silyl]oxy}-3-(phenyloxy)propyl](phenylmethyl)amino]methyl}-3,4-dihydro-2H-chromen-6-yl)-2-pyridinecarboxylic acid

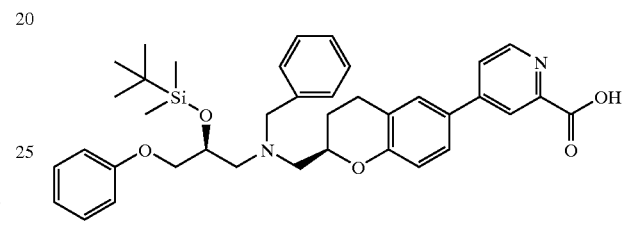

The title compound was prepared in 31% yield according to the method described in Example 89 by replacing the pyridinecarboxamide with methyl 4-chloro-2-pyridinecarboxylate of Example 1. MS m/z 639.2 (MH$^+$), retention time (LC-MS)=2.94 minutes.

EXAMPLE 91

Preparation of 4-((2R)-2-{[[(2S)-2-{[(1,1-dimethylethyl)(dimethyl)silyl]oxy}-3-(phenyloxy)propyl](phenylmethyl)amino]methyl}-3,4-dihydro-2H-chromen-6-yl)-N-[(4-fluorophenyl)methyl]-2-pyridinecarboxamide

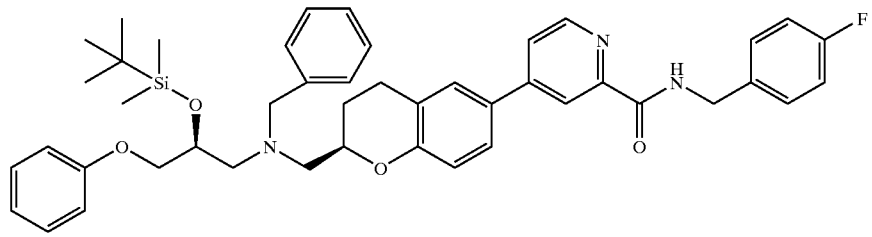

Into a solution of 4-((2R)-2-{[[(2S)-2-{[(1,1-dimethylethyl)(dimethyl)silyl]oxy}-3-(phenyloxy)propyl](phenylmethyl)amino]methyl}-3,4-dihydro-2H-chromen-6-yl)-2-pyridinecarboxylic acid (Example 90, 82 mg, 0.13 mmol) in dichloromethane (2 mL) was added 4-fluorobenzylamine (33 mg, 0.26 mmol, 2.0 eq.), 1-[3-(dimethylamino)propyl]-3-ethylcarbodiimide hydrochloride (50 mg, 0.26 mmol, 2.0 eq.), and 1-hydroxybenzotriazole (35 mg, 0.26 mmol, 2.0 eq.). The solution was stirred overnight at room temperature before being concentrated in vacuo to remove volatile components. The crude residue was purified by flash chromatography on silica gel eluted with 75:25 hexanes/ethyl acetate. The title compound was obtained as a yellow oil (34 mg, 35%): $^1$H NMR (300 MHz, CDCl$_3$) δ8.47 (d, 1 H), 8.40 (s, 2 H), 7.55 (dd, 1 H), 7.44–7.39 (m, 2 H), 7.34–7.29 (m, 4 H), 7.25–7.20 (m, 4 H), 7.01 (t, 2 H), 6.93–6.80 (m, 4 H), 4.64 (d, 2 H), 4.22–4.16 (m, 1 H), 4.11–4.05 (m, 1 H), 3.83 (s, 2 H), 3.75 (dd, 1 H), 2.94–2.80 (m, 2 H), 2.73–2.67 (m, 4 H), 1.71–1.57 (m, 2 H), 0.86 (s, 9H), 0.09 (s, 3 H), 0.05 (s, 3 H); MS m/z 746.5 (M$^+$).

EXAMPLE 92

Preparation of N-cyclohexyl-4-((2R)-2-{[[(2S)-2-{[(1,1-dimethylethyl)(dimethyl)silyl]oxy}-3-(phenyloxy)propyl](phenylmethyl)amino]methyl}-3,4-dihydro-2H-chromen-6-yl)-2-pyridinecarboxamide

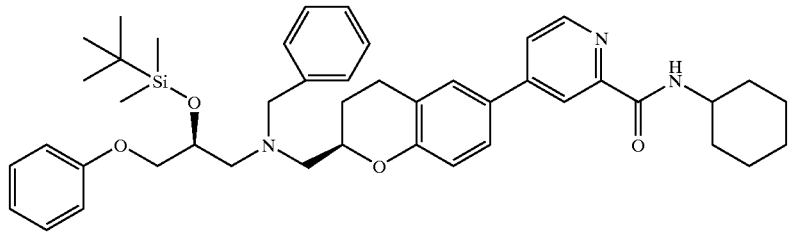

The title compound was prepared according to the method of Example 89 (33% yield): MS m/z 720.4 (MH$^+$), retention time (LC-MS)=3.94 minutes.

EXAMPLE 93

Preparation of 4-[(2R)-2-({[(2S)-2-{[(1,1-dimethylethyl)(dimethyl)silyl]oxy}-3-(phenyloxy)propyl]amino}methyl)-3,4-dihydro-2H-chromen-6-yl]-2-pyridinecarboxamide

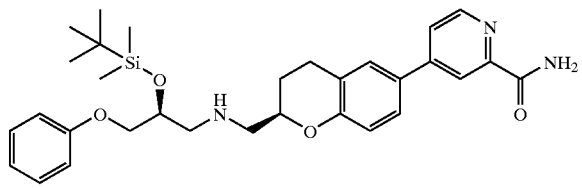

4-((2R)-2-{[[(2S)-2-{[(1,1-Dimethylethyl)(dimethyl)silyl]oxy}-3-(phenyloxy)propyl](phenylmethyl)amino]methyl}-3,4-dihydro-2H-chromen-6-yl)-2-pyridinecarboxamide (Example 89, 44 mg, 0.07 mmol) was added to a suspension of 10% Pd/C (44 mg) in methanol (3 mL). Ammonium formate (22 mg, 0.35 mmol, 5.0 eq.) was added, and the mixture was heated at reflux for 30 minutes. Solids were removed by filtration through Celite®, and the filtrate was concentrated in vacuo. The title compound was collected as a pale yellow oil (25 mg, 66%): $^1$H NMR (300 MHz, acetone-d$_6$) δ8.58 (d, 1 H), 8.32 (d, 1 H), 7.96 (broad s, 1 H), 7.78 (dd, 1 H), 7.60–7.56 (m, 2 H), 7.30–7.24 (m, 2 H), 6.95–6.81 (m, 4 H), 6.80 (broad s, 1 H), 4.25–4.19 (m, 2 H), 4.15–4.07 (m, 1 H), 3.99–3.92 (m, 1 H), 2.99–2.86 (m, 6 H), 2.13–2.06 (m, 1 H), 1.90–1.80 (m, 1 H), 0.92 (s, 9 H), 0.16 (s, 3 H), 0.13 (s, 3 H); MS m/z 548.3 (MH$^+$).

EXAMPLE 94

Preparation of 4-[(2R)-2-({[(2S)-2-hydroxy-3-(phenyloxy)propyl]amino}methyl)-3,4-dihydro-2H-chromen-6-yl]-2-pyridinecarboxamide

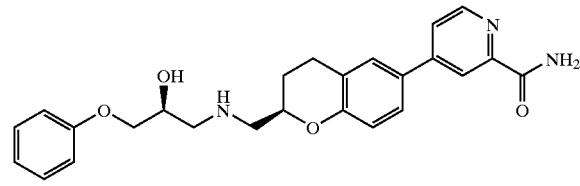

4-[(2R)-2-({[(2S)-2-{[(1,1-Dimethylethyl)(dimethyl)silyl]oxy}-3-(phenyloxy)propyl]amino}methyl)-3,4-dihydro-2H-chromen-6-yl]-2-pyridinecarboxamide (Example 93, 20 mg, 0.04 mmol) was stirred in an excess of 4M HCl in dioxane at room temperature for 30 minutes. The volatile components were removed by rotary evaporation, and the residue was washed with dichloromethane. After drying under vacuum, the title compound was collected as the dihydrochloride salt (8 mg, 43%): MS m/z 434.3 (MH$^+$ of the free base); retention time (LC-MS)=2.02 minutes.

EXAMPLES 95–96

By employing the methods described above for Examples 93–94, the following were similarly prepared and characterized:

TABLE 6

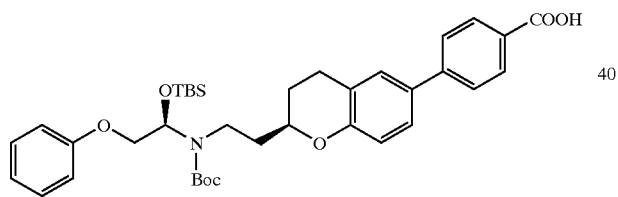

| Example No. | R⁸ | MS [M + H⁺] | LC-MS RT (min) |
|---|---|---|---|
| 95 | ![4-fluorobenzyl with gem-dimethyl] | 542.3 | 2.49 |
| 96 | ![cyclohexyl with gem-dimethyl] | 516.4 | 2.55 |

EXAMPLE 97

Preparation of 4-((2S)-2-{[(tert-butoxycarbonyl)((2S)-2-{[tert-butyl(dimethyl)silyl]oxy}-3-phenoxypropyl)amino]methyl}-3,4-dihydro-2H-chromen-6-yl)benzoic acid To a degassed solution of Example 83 (0.36 g, 0.55 mmol, 1.0 eq.) in toluene (4.0 mL) were added methyl 4-iodobenzoate (0.22 g, 0.83 mmol, 1.5 eq.), dichloro[1,1'-bis(diphenylphosphino)ferrocene]palladium(II) dichloromethane adduct (0.032 g, 0.038 mmol, 0.07 eq.), and 2M sodium carbonate (2.8 mL, 5.51 mmol, 10.0 equiv.) under argon atmosphere at room temperature. The reaction mixture was heated to 85° C. under argon atmosphere and stirred for 18 hours. The mixture was diluted with distilled water (5 mL) and extracted with diethyl ether (3×5 mL). The combined extracts were dried over magnesium sulfate, filtered and concentrated under reduced pressure. Purification by flash chromatography on a silica gel column (5%–10% ethyl acetate/hexanes) yielded the intermediate the desired product, 0.23 g. The pure intermediate was then treated with 1N sodium hydroxide (1.0 mL) in the presence of methanol (4.0 mL) and distilled water (1.0 mL) and stirred at room temperature for 24 hours. The mixture was acidified by 1N hydrochloric acid and then extracted with ethyl acetate (3×4 mL). The extracts were washed with brine, dried over magnesium sulfate, filtered and concentrated under reduced pressure to yield the expected product as white solid (0.16 g, 44%). ¹H NMR (CDCl₃) δ8.02 (d, 2H), 7.53 (d, 2H), 7.29–7.18 (m, 5H), 6.87–6.77 (m, 3H), 4.25–4.14 (m, 2H), 3.79–3.56 (m, 4H), 3.28–3.19 (m, 2H), 2.82–2.72 (m 2H), 1.98–1.90 (m, 1H), 1.67–1.58 (m, 1 H), 1.38 (s, 9H), 0.81 (s, 9H), 0.001 (s, 6H).

EXAMPLE 98

Preparation of 3-((2S)-2-{[(tert-butoxycarbonyl)((2S)-2-{[tert-butyl(dimethyl)silyl]oxy}-3-phenoxypropyl)amino]methyl}-3,4-dihydro-2H-chromen-6-yl)benzoic acid

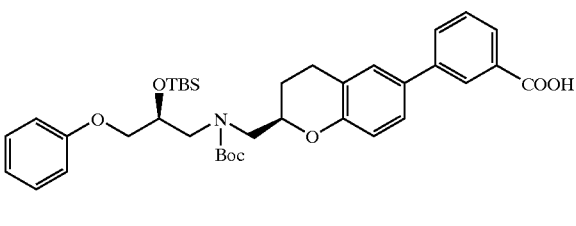

By using a synthetic route identical to that of Example 97 and substituting methyl 3-bromobenzoate for methyl 4-iodobenzoate, the title compound was prepared. LC-MS: 548.4 (MH⁺-Boc), retention time: 5.01 min.

EXAMPLE 99

Preparation of N-{4-[(2S)-2-{[(2S)-2-hydroxy-3-phenoxypropyl]amino}methyl)-3,4-dihydro-2H-chromen-6-yl]benzoyl}benzenesulfonamide

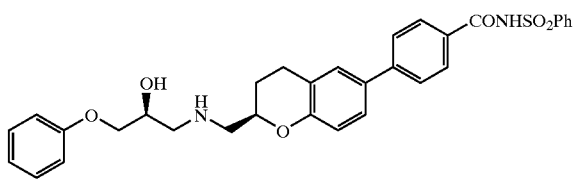

To a solution of Example 97 (0.058 g, 0.09 mmol, 1.0 eq.) in dichloromethane (1.5 mL) were added benzenesulfonamide (0.015 mg, 0.095 mmol, 1.05 eq.), 1-[3-(dimethylamino)propyl]-3-ethylacrbodiimide hydrochloride (0.021 mg, 0.11 mmol, 1.2 eq.), and 4-(dimethylamino)-pyridine (0.011 mg, 0.09 mmol, 1.0 equiv.). The reaction mixture was stirred at room temperature for 36 hours and then treated with hydrochloric acid in 1,4-dioxane (2 mL). The resulting mixture was stirred at room temperature for 3 hours and basified with 1 N sodium hydroxide. The mixture was extracted with ethyl acetate/methanol (3×2 mL). The combined extracts were dried over magnesium sulfate, filtered and concentrated under reduced pressure to give clear oil. Purification by HPLC yielded the desired TFA salt as a white solid (0.011g, 22%). $^1$H NMR (CDCl$_3$) δ8.21 (d, 2H), 7.78 (d, 2H), 7.65–7.47 (m, 4H), 7.41 (d, 2H), 7.28–7.11 (m, 2H), 6.98–6.80 (m, 5H), 4.85–4.51 (m, 2H), 4.11–3.92 (m, 4H), 3.60–3.22 (m, 2H), 2.78–2.70 (m, 2H), 2.15–2.03 (m, 1H), 1.86–1.71 (m, 1H); LC-MS: 573.1 (MH$^+$), retention time: 2.70 min.

Using the procedures outlined in Examples 97–99 the following compounds were prepared and characterized:

EXAMPLE 102

Methyl 4-[(2R)-2-{[(2S)-3-(9H-carbazol-4-yloxy)-2-hydroxypropyl]amino}methyl)-3,4-dihydro-2H-6-yl]benzoate

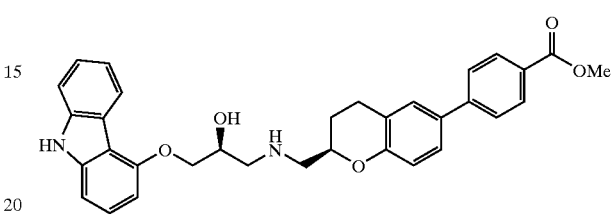

The crude methylene chloride solution of aldehyde from Example 66 was treated with 50 mg (0.187 mmol) of (2S)-1-amino-3-(9H-carbazol-4-yloxy)-2-propanol (preparation described in WO 9809625), followed by the addition of 0.18 mL (3.06 mmol) of glacial acetic acid. This solution was stirred at room temperature for 5 minutes, then 108 mg (0.51 mmol) of sodium triacetoxy borohydride was added. The resulting solution was stirred at room temperature for 16 hours. After this time the solution was quenched with 2M potassium carbonate to pH 9–10, extracted with methylene chloride, dried over sodium sulfate, and concentrated in vacuo. The crude product was purified by Biotage (100% methylene chloride to 3% methanol/methylene chloride) to provide product. m/z 537.4 [M+H]$^+$.

TABLE 7

| Example No. | R$^9$ | MS [MH$^+$] | HPLC RT (min) |
|---|---|---|---|
| 100 | Ph | 573.5 | 2.55 |
| 101 | Me | 511.4 | 2.28 |

EXAMPLE 103

Preparation of methyl 6-[(2R)-2-({[(2S)-2-hydroxy-3-phenoxypropyl]amino}methyl)-3,4-dihydro-02H-chromen-6-yl]-2-naphthoate

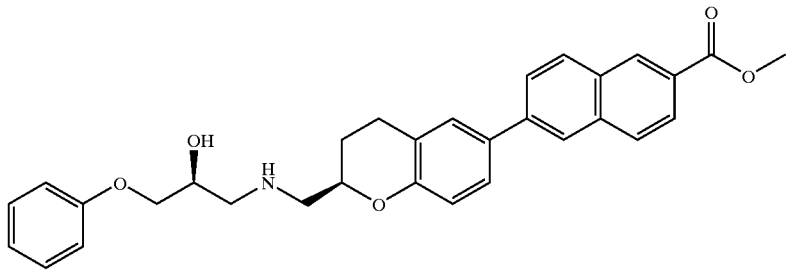

Argon was bubbled through a solution of Example 83 (0.153 mmol, 1.0 eq.) in toluene (3 mL) for 10 minutes. To this solution was added [1,1'-bis(diphenylphosphino)ferrocene]dichloropalladium (II) (0.0107 mmol, 0.07 eq.) and methyl 6-bromo-2-naphthoate (0.230 mmol, 1.5 eq.) in a single portion. The resulting reaction mixture was bubbled degassed with argon again for an additional 5 minutes before aqueous $Na_2CO_3$ (2M, 1.53 mmol, 10.0 eq.) was added. The mixture was heated to 85° C. overnight. The resulting solution was cooled to room temperature, water was added and the two-phase mixture was extracted with ethyl acetate. The organic extracts were dried over anhydrous sodium sulfate and concentrated in vacuo. The resulting residue was dissolved in 4M HCl in dioxane (3 mL) and was stirred at room temperature for 2 hours. The solution was basified with 1 N NaOH and extracted with ethyl acetate. The organic extract was dried over anhydrous sodium sulfate, concentrated and purified by reverse phase HPLC[#] conditions. Example 103 was obtained as a white solid in 66% yield. $MH^+$=498.4, retention time (LC-MS)=2.72 min.

[#] Reverse phase preparative HPLC conditions:

Column: YMC-Guardpack, Pro C18, AS12S05-L530WT, GAS-3605-5

Guard column: ODS-A prep guard cartridge, GCAAS210110UCA

Solvents: solvent A: acetonitrile with 0.1% TFA (v/v); solvent B: water with 0.1% TFA (v/v)

| Conditions: | | | | | | | |
|---|---|---|---|---|---|---|---|
| Time (min) | 0:00 | 1:00 | 19:00 | 21:00 | 23:00 | 24:00 | 25:00 |
| % B | 10.0 | 10.0 | 80.0 | 98.0 | 98.0 | 10.0 | 10.0 |
| Flow (mL/min) | 24.90 | | | | | | 24.90 |

Substituting the appropriate starting materials, the compounds shown in Tables 8–11 were prepared and characterized utilizing the methods of Examples 84, 102, and 103.

TABLE 8

Methyl 4-[(2R)-2-({[(2S)-2-hydroxy-3-aryloxypropyl]amino}methyl)-3.4-dihydro-2H chromen-6-yl]benzoates

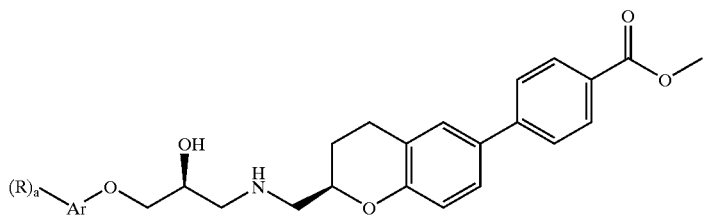

| Example No. | $(R)_a$—Ar— | HPLC RT (min) or LC-MS RT (min) | MS [source] | Method of Example No. | salt |
|---|---|---|---|---|---|
| 104 | 2-Cl—Ph— | 2.57 | 482(M + H) + (electrospray) | 103 | HCl |
| 105 | 2-CF₃—Ph— | 2.65 | 516(M + H) + (electrospray) | 84 | HCl |
| 106 | 3-CF₃—Ph— | 2.60 | 516(M + H) + (electrospray) | 84 | HCl |
| 107 | 4-CF₃—Ph— | 2.74 | 516(M + H) + (electrospray) | 84 | HCl |
| 108 | Pyridin-3-yl | 1.88 | 449(M + H) + (electrospray) | 84 | 2 HCl |
| 109 | 4-F—Ph— | 2.48 | 466.3 | 84 | |
| 110 | 2-F—Ph— | 2.57 | 466.3 | 84 | |
| 111 | 4-HO—Ph— | 2.18 | 464.3 | 84 | TFA |
| 112 | 2-HO—Ph— | 2.44 | 464.3 | 84 | TFA |

TABLE 9

Ethyl 3-[(2R)-2-({[(2S)-2-hydroxy-3-aryloxypropyl]amino}methyl)-3,4-dihydro-2H-chromen-6-yl]benzoates

| Example No. | (R)ₐ—Ar— | LC-MS RT (min) | MS [MH+] | Method of Example No. |
|---|---|---|---|---|
| 113 | Ph— | 2.70 | 462.3 | 84 |
| 114 | 4-F—Ph— | 2.61 | 480.3 | 84 |
| 115 | 2-F—Ph— | 2.69 | 480.3 | 84 |

TABLE 10

Methyl 4-[(2R)-2-({[(2S)-2-hydroxy-3-arylthiopropyl]amino}methyl)-3,4-dihydro-2H-chromen-6-yl]benzoates

| Example No. | (R)ₐ—Ar— | HPLC RT (min) | MS [source] | Method of Example No. | salt |
|---|---|---|---|---|---|
| 116 | Ph— | 2.68 | 464(M + H) + (electrospray) | 84 | TFA |
| 117 | 2-Et—Ph— | 2.77 | 492(M + H) + (electrospray) | 84 | TFA |
| 118 | 4-Et—Ph | 2.80 | 492(M + H) + (electrospray) | 84 | TFA |
| 119 | 2-i-Pr—Ph— | 2.87 | 505.6(M + H) + (electrospray) | 84 | TFA |
| 120 | 2-Cl—Ph— | 2.71 | 498(M + H) + (electrospray) | 84 | TFA |
| 121 | 4-Cl—Ph— | 2.76 | 498(M) + (electrospray) | 84 | TFA |
| 122 | 2-F—Ph— | 2.65 | 482(M + H) + (electrospray) | 84 | TFA |
| 123 | 3-F—Ph— | 2.71 | 482(M + H) + (electrospray) | 84 | TFA |
| 124 | 4-F—Ph— | 2.64 | 482(M + H) + (electrospray) | 84 | TFA |
| 125 | 2-MeO—Ph— | 2.60 | 494(M + H) + (electrospray) | 84 | TFA |
| 126 | 3-MeO—Ph— | 2.63 | 494(M + H) + (electrospray) | 84 | TFA |
| 127 | 4-MeO—Ph— | 2.59 | 494(M + H) + (electrospray) | 84 | TFA |
| 128 | 3-CF₃—Ph— | 2.81 | 532(M + H) + (electrospray) | 84 | TFA |
| 129 | 4-CF₃—Ph— | 2.80 | 532(M + H) + (electrospray) | 84 | TFA |

TABLE 11

2-Hydroxy-3-aryloxypropyl[amino}methyl)-3,4-dihydro-2H-chromen-6-yl]
arylcarboxylates

| Example No. | Y | LC-MS RT (min) | MS [MH+] | Method of Example No. | salt |
|---|---|---|---|---|---|
| 130 | methyl 2,3-dihydrobenzofuran-7-carboxylate, 5-yl | 2.32 | 490.4 | 103 | TFA |
| 131 | ethyl 1,5-dimethyl-1H-pyrazole-3-carboxylate, 4-yl | 2.11 | 480.3 | 103 | 2TFA |
| 132 | methyl thiophene-4-carboxylate, 2-yl | 2.41 | 454.3 | 103 | TFA |
| 133 | methyl thiophene-2-carboxylate, 4-yl | 2.43 | 454.3 | 103 | TFA |
| 134 | ethyl 5-phenyloxazole-4-carboxylate, 2-yl | 2.71 | 529.3 | 103 | |
| 135 | methyl 5-phenylthiazole-4-carboxylate, 2-yl | 2.66 | 531.3 | 103 | TFA |

TABLE 11-continued

2-Hydroxy-3-aryloxypropyl[amino}methyl)-3,4-dihydro-2H-chromen-6-yl] arylcarboxylates

| Example No. | Y | LC-MS RT (min) | MS [MH+] | Method of Example No. | salt |
|---|---|---|---|---|---|
| 136 | (2-phenyl-thiazol-5-yl ethyl ester) | 2.78 | 545.4 | 103 | TFA |
| 137 | (2-isopropyl-thiazol-5-yl ethyl ester) | 2.98 | 511.4 | 103 | TFA |
| 138 | (5-isopropyl-thiazol-4-yl methyl ester) | 2.70 | 497.4 | 103 | TFA |

EXAMPLE 139

Preparation of 4-{(2R)-2-[({(2S)-2-hydroxy-3-[4-(2-methoxyethyl)phenoxy]propyl}amino)methyl]-3,4-dihydro-2H-chromen-6-yl}benzoic acid

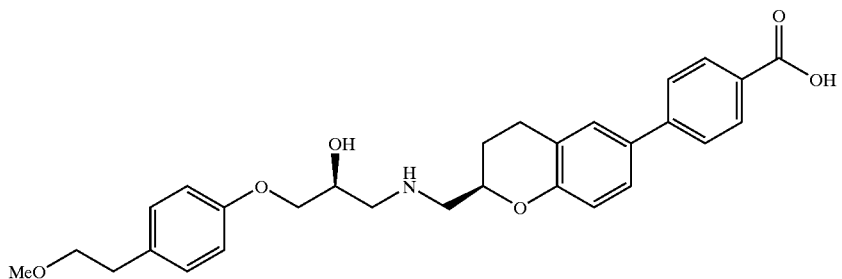

To a solution of epoxide (Example 16, 0.25 mmol) in 2 mL of aqueous 1,4-dioxane (10% water) was added methyl 4-[(2R)-2-(aminomethyl)-3,4-dihydro-2H-chromen-6-yl] benzoate (40 mg, 0.13 mmol). The mixture was stirred at 80° C. for 72 hours and allowed to cool to room temperature. When ambient temperature was achieved, 1N aqueous sodium hydroxide (1 mL) was added to the solution at room temperature, and stirring continued for another 0.5 hour. The

EXAMPLE 140

Preparation of 4-[(2R)-2-({[(2S)-3-(2,6-diisopropylphenoxy)-2-hydroxypropyl]amino}methyl)-3,4-dihydro-2H-chromen-6-yl]benzoic acid

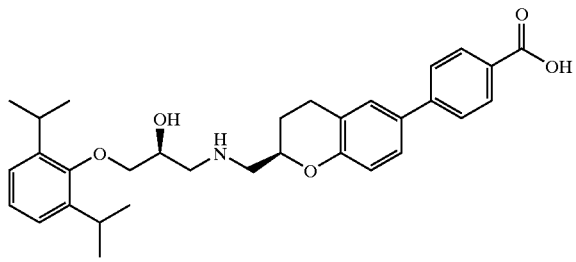

Crude (2S)-2-[(2,6-diisopropylphenoxy)methyl]oxirane (Example 17, 0.55 mmol), was diluted in 2 mL of isopropanol (10% water), and treated with methyl 4-[(2R)-2-(aminomethyl)-3,4-dihydro-2H-chromen-6-yl]benzoate (Example 39, 88 mg, 0.26 mmol). This mixture was stirred at 80° C. for 72 hours, then 1N sodium hydroxide (2 mL) was added to the solution at room temperature, and stirred for another 0.5 hour. The product was then purified by preparative HPLC (Gradient 0–70% Acetonitrile/0.1% aq. TFA) to obtain 56.3 mg of product (as a TFA salt) MH+518.3 (free base).

EXAMPLE 141

Preparation of 4-[(2R)-2-({[(2S)-3-(9H-Carbazol-4-yloxy)-2-hydroxypropyl]amino}methyl)-3,4-dihydro-2H-chromen-6-yl]benzoic acid

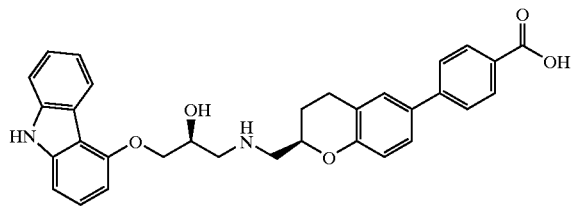

To the ester prepared in Example 102 (30 mg, 0.056 mmol) of) was added 1 mL of 2N sodium hydroxide. The solution was stirred at room temperature for 16 hours, and was then purified by preparative HPLC (Gradient 0–70% Acetonitrile/0.1% aq. TFA) to obtain 1.2 mg of product (as aTFA salt). m/z 523.3 [M+H]+ (free base).

EXAMPLE 142

Preparation of 4-[(2R)-2-({[(2S)-2-Hydroxy-3-phenoxyropyl]amino}methyl)-3,4-dihydro-2H-chromen-6-yl]benzoic acid

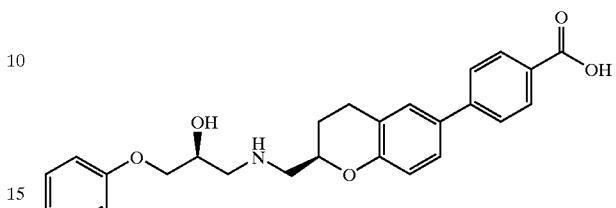

Method (1). A solution of methyl 4-[(2R)-2-({[(2S)-2-hydroxy-3-phenoxypropyl]amino}methyl)-3,4-dihydro-2H-chromen-6-yl]benzoate (0.250 mmol) and 1 M NaOH (0.75 mmol, 3.0 eq.) in EtOH/H$_2$O (4 mL/1.5 mL) was heated to reflux and maintained at that temperature for 1.5 hours. The solvents were evaporated and the resulting residue was dissolved in THF/H$_2$O. To this solution was added an excess of 2N HCl and at which time a precipitate was formed. The precipitate was collected by filtration, washed with water and diethyl ether, and dried in vacuo. The product was obtained as pale yellow solid in 72% yield. MH$^+$=434.3, retention time (LC-MS)=2.20 min.

Method (2). Methyl 4-[(2R)-2-({[(2S)-2-hydroxy-3-phenoxypropyl]amino}methyl)-3,4-dihydro-2H-chromen-6-yl]benzoate methanesulfonate (Example 287, 25 g, 0.046 mmol., 1.0 eq.) was dissolved in 350 mL methanol and 100 mL water, then heated to reflux. To this solution was added a solution of NaOH (11.1 g, 40.0 mmol., 6.0 eq.) dissolved in 60 mL of water (dropwise addition over a period of two hours). The reaction was refluxed for an additional 3 hours, cooled to 15° C., and the sodium salt was filtered. The wet sodium salt was then dissolved in a 1:1 solution of THF water (325 mL), warmed to 30° C., and filtered. To the clear solution was added 3M HCl until the pH was less than 2. The suspension was stirred at room temperature for 16 hours, filtered, washed with 50 mL water and dried to yield 18.2 g (84% yield) of 4-[(2R)-2-({[(2S)-2-hydroxy-3-phenoxypropyl]amino}methyl)-3,4-dihydro-2H-chromen-6-yl]benzoic acid hydrochloride. Mp–250° C.;NMR (DMSO-d$_6$) δ1.75 (m, 1 H), 2.13 (m 1 H), 2.80 (m, 2H), 3.12 (m, 1H), 3.46 (m, 2H), 4.02 (m, 2H), 4.35 (m, 1 H), 4.56 (tt, J=7, 1.5 Hz, 1H),5.87 (bs, 1H, OH), 6.95 (m, 4H, ArH), 7.33 (t, J=7 Hz, 2H, ArH), 7.52 (m, 2H, ArH), 7.77 (d, J=8 Hz, 2H, ArH), 7.95 (d, J=8 Hz, 2H, ArH); MS (EI): mlz 434 (MH$^+$).

By using a combination of the methods described for Examples 139–142, and substituting the appropriate starting materials, the compounds shown in Tables 12–15 below were prepared and characterized.

TABLE 12

4-[(2R)-2-({[(2S)-2-Hydroxy-3-aryloxypropyl]amino}methyl)-3,4-dihydro-2H-chromen-6-yl]benzoic acids

| Example No | (R)$_a$—Ar— | MS [MH+] | HPLC RT (min) | Method of Example No. | Salt |
|---|---|---|---|---|---|
| 143 | 2-Et—Ph— | 462 | 2.38 | 142 | |
| 144 | 3-Et—Ph— | 462 | | 142 | |
| 145 | 4-Et—Ph— | 462 | | 142 | |
| 146 | 2-CN—Ph— | 459 | 2.09 | 142 | |
| 147 | 3-CN—Ph— | 459 | 2.09 | 142 | |
| 148 | 4-CN—Ph— | 459 | 2.1 | 142 | |
| 149 | 3-i-Pr—Ph— | 490 | 2.46 | 142 | |
| 150 | 2,6-di-MeO—Ph— | 494 | 2.24 | 142 | |
| 151 | 2-EtO—Ph | 478 | 2.3 | 142 | |
| 152 | 2-F-6-MeO—Ph— | 482 | 2.28 | 142 | |
| 153 | 2-i-PrO—Ph— | 492 | 2.38 | 142 | |
| 154 | 2,3-di-MeO—Ph— | 494 | 2.2 | 142 | |
| 155 | 2—Ph—Ph— | 510 | 2.45 | 142 | |
| 156 | 2-Cl—Ph— | 468(M + H) + (electrospray) | 2.29 | 142 | HCl |
| 157 | 2-CF$_3$—Ph— | 502(M + H) + (electrospray) | 2.41 | 142 | HCl |
| 158 | 3-CF$_3$—Ph— | 502(M + H) + (electrospray) | 2.38 | 142 | HCl |
| 159 | 4-CF$_3$—Ph— | 502(M + H) + (electrospray) | 2.44 | 142 | TFA |
| 160 | pyridin-3-yl- | 435(M + H) + (electrospray) | 1.47 | 142 | 2TFA |
| 161 | 4-F—Ph— | 452.3 | 2.23 | 142 | HCl |
| 162 | 2-F—Ph— | 452.3 | 2.25 | 142 | HCl |
| 163 | 4-HO—Ph— | 450.3 | 2.11 | 142 | HCl |
| 164 | 2-HO—Ph— | 450.4 | 2.15 | 142 | HCl |

TABLE 13

3-[(2R)-2-({[(2S)-2-Hydroxy-3-aryloxypropyl]amino}methyl)-3,4-dihydro-2H-chromen-6-yl]benzoic acids

| Example No. | (R)$_a$—Ar— | LC-MS RT (min) | MS [MH+] | Method of Example No. |
|---|---|---|---|---|
| 165 | Ph— | 2.70 | 462.3 | 142 |
| 166 | 4-F—Ph— | 2.61 | 480.3 | 142 |
| 167 | 2-F—Ph— | 2.69 | 480.3 | 142 |

TABLE 14

4-[(2R)-2-({[(2S)-2-Hydroxy-3-arylthiopropyl]amino}methyl)-3,4-dihydro-2H-chromen-6-yl]benzoic acids

| Example No. | (R)$_a$—Ar— | HPLC RT (min) | MS [source] | Method of Example No. | salt |
|---|---|---|---|---|---|
| 168 | Ph | 2.27 | 456(M + H) + (electrospray) | 139 | HCl |
| 169 | 2-Et—Ph | 2.42 | 478(M + H) + (electrospray) | 139 | HCl |
| 170 | 4-Et—Ph— | 2.60 | 478(M + H) + (electrospray) | 139 | HCl |
| 171 | 2-i-Pr—Ph | 2.68 | 492(M + H) + (electrospray) | 139 | HCl |
| 172 | 2-Cl—Ph— | 2.35 | 484(M + H) + (electrospray) | 139 | HCl |
| 173 | 4-Cl—Ph— | 2.55 | 484(M + H) + (electrospray) | 139 | HCl |
| 174 | 2-F—Ph— | 2.30 | 468(M + H) + (electrospray) | 122 | TFA |
| 175 | 3-F—Ph— | 2.30 | 468(M + H) + (electrospray) | 139 | HCl |
| 176 | 4-F—Ph— | 2.42 | 468(M + H) + (electrospray) | 139 | HCl |
| 177 | 2-MeO—Ph— | 2.42 | 480(M + H) + (electrospray) | 139 | HCl |
| 178 | 3-MeO—Ph— | 2.29 | 480(M + H) + (electrospray) | 139 | HCl |
| 179 | 4-MeO—Ph— | 2.25 | 480(M + H) + (electrospray) | 139 | HCl |
| 180 | 3-CF$_3$—Ph— | 2.58 | 518(M + H) + (electrospray) | 139 | HCl |
| 181 | 4-CF$_3$—Ph— | 2.61 | 518(M + H) + (electrospray) | 139 | HCl |

TABLE 15

[(2R)-2-({[(2S)-2-Hydroxy-3-phenoxyoxypropyl]amino}methyl)-3,4-dihydro-2H-chromen-6-yl]arylcarboxylic acids

| Example No. | Y | LC-MS RT (min) | MS [MH+] | Method of Example No. | salt |
|---|---|---|---|---|---|
| 182 | (6-carboxy-2-naphthyl) | 2.38 | 484.4 | 142 | Na |

TABLE 15-continued

[(2R)-2-({[(2S)-2-Hydroxy-3-phenoxyoxypropyl]amino}methyl)-3,4-dihydro-2H-chromen-6-yl]arylcarboxylic acids

| Example No. | Y | LC-MS RT (min) | MS [MH+] | Method of Example No. | salt |
|---|---|---|---|---|---|
| 183 | thiophene-2-carboxylic acid (4-yl) | 2.25 | 440.3 | 142 | HCl |
| 184 | 1,5-dimethyl-pyrazole-3-carboxylic acid (4-yl) | 2.02 | 452.3 | 142 | 2HCl |
| 185 | 2,3-dihydrobenzofuran-7-carboxylic acid (5-yl) | 2.23 | 476.4 | 142 | HCl |
| 186 | thiophene-3-carboxylic acid (5-yl) | 2.27 | 440.3 | 142 | TFA |
| 187 | 5-phenyloxazole-4-carboxylic acid (2-yl) | 2.33 | 501.3 | 142 | HCl |
| 188 | 5-phenylthiazole-4-carboxylic acid (2-yl) | 2.39 | 517.3 | 142 | HCl |

TABLE 15-continued

[(2R)-2-({[(2S)-2-Hydroxy-3-phenoxyoxypropyl]amino}methyl)-3,4-dihydro-2H-chromen-6-yl]arylcarboxylic acids

| Example No. | Y | LC-MS RT (min) | MS [MH+] | Method of Example No. | salt |
|---|---|---|---|---|---|
| 189 | (2-thiazolyl, 4-phenyl, 5-COOH) | 2.38 | 517.3 | 142 | HCl |
| 190 | (2-thiazolyl, 4-isopropyl, 5-COOH) | 2.38 | 483.3 | 142 | HCl |
| 191 | (2-thiazolyl, 4-COOH, 5-isopropyl) | 2.46 | 483.3 | 142 | TFA |

EXAMPLE 192

Preparation of phenylmethyl 4-bromo-2-fluorobenzoate

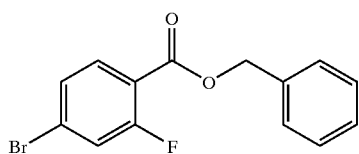

Benzyl bromide (0.86 g, 5.0 mmol, 1.1 eq.) was added neat to a solution of 4-bromo-2-fluorobenzoic acid (1.0 g, 4.6 mmol) and 1,8-diazabicyclo[5.4.0]undec-7-ene (1.36 mL, 9.2 mmol, 2.0 eq.) in anhydrous acetonitrile (20 mL). The reaction was stirred at room temperature for 18 hours before removing the solvent in vacuo. The residue was diluted with ether and washed with water, saturated aqueous sodium bicarbonate, saturated aqueous ammonium chloride, and brine. The organic layer was dried (MgSO$_4$) and concentrated in vacuo to provide the title compound as a pale yellow oil that crystallized into long needles upon standing (1.4 g, 99%): $^1$H NMR (300 MHz, CDCl$_3$) δ7.82 (t, 1 H), 7.42–7.31 (m, 7 H), 5.35 (s, 2 H); GC/MS m/z 308/310 (M$^+$ and M$^{+2}$).

EXAMPLE 193

Preparation of Phenylmethyl 4-bromo-2-(butylamino)benzoate

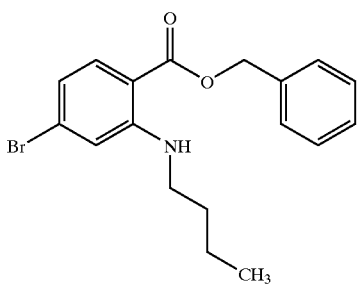

Phenylmethyl 4-bromo-2-fluorobenzoate (Example 192, 315 mg, 1.02 mmol) was combined with n-butylamine (110 μl, 1.12 mmol, 1.1 eq.) and solid cesium carbonate (1.66 g, 5.1 mmol, 5.0 eq.) in anhydrous methyl sulfoxide (4 mL)

and heated at 75° C. for 1.5 hours. The reaction was cooled and partitioned between diethyl ether and water. The aqueous layer was separated and extracted with fresh ether. The organic layers were combined, washed with brine (4×), dried (MgSO$_4$), and concentrated in vacuo to a crude oil. The crude was purified by flash chromatography on silica gel eluted with 95:5 hexanes/ether to provide the title compound as a yellow oil (52 mg, 14%): $^1$H NMR (300 MHz, CDCl$_3$) δ7.76 (d, 1 H), 7.71 (broad s, 1 H), 7.41–7.32 (m, 5 H), 6.80 (s, 1 H), 6.63 (d, 1 H), 5.26 (s, 2 H), 3.16–3.10 (m, 2 H), 1.69–1.60 (m, 2 H), 150–1.38 (m, 2 H), 0.95 (t, 3 H); MS m/z 362.0 and 364.0 (MH$^+$ and MH+2).

EXAMPLE 194

Preparation of Phenylmethyl 2-(butylamino)4-((2R)-2-{[[(2S)-2-{[(1,1-dimethylethyl)(dimethyl)silyl]oxy}-3-(phenyloxy)propyl](phenylmethyl)amino]methyl}-3,4-dihydro-2H-chromen-6-yl)benzoate

EXAMPLE 195

Preparation of 2-(butylamino)-4-[(2R)-2-({[(2)-2-hydroxy-3-(phenyloxy)propyl]amino}methyl)-3,4-dihydro-2H-chromen-6-yl]benzoic acid

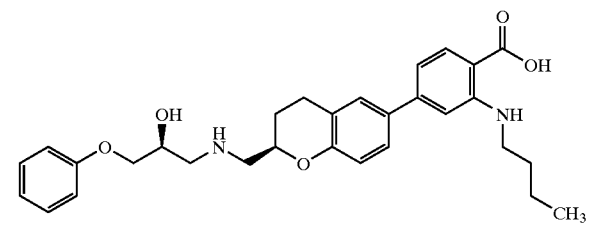

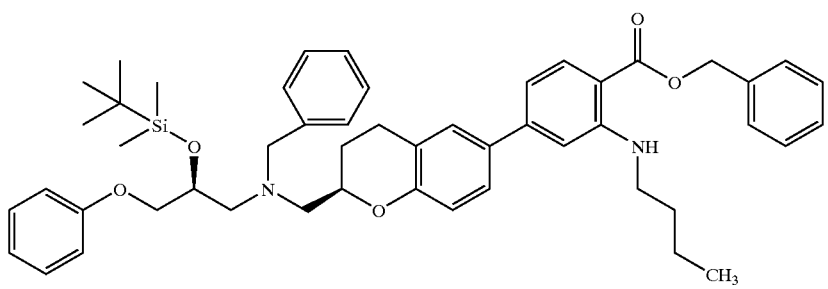

Argon gas was bubbled through a solution of (2S)-N-{[(2R)-6-(4,4,5,5-tetramethyl-1,3,2-dioxaborolan-2-yl)-3,4-dihydro-2H-chromen-2-yl]methyl}-2-{[(1,1-dimethylethyl)(dimethyl)silyl]oxy}-N-(phenylmethyl)-3-(phenyloxy)-1-propanamine (Example 88, 92 mg, 0.14 mmol) in toluene (1.25 mL), tetrahydrofuran (0.25 mL), and aqueous Na$_2$CO$_3$ (0.50 mL of a 2M solution) for 10 minutes. Pd(dppf)Cl$_2$ (10 mg, 0.014 mmol, 0.1 eq.) and phenylmethyl 4-bromo-2-(butylamino)benzoate (Example 193, 52 mg, 0.14 mmol, 1.0 eq.) were added, and argon was bubbled through the mixture for an additional 5 minutes before the mixture was stirred vigorously at 85° C. for 3 hours. The reaction mixture was cooled and filtered through a pad of Celite® with the aid of ethyl acetate. The filtrate was transferred to a separatory funnel where the water layer was removed. The organic layer was dried (MgSO$_4$) and concentrated in vacuo to a crude oil. The crude was purified by flash chromatography on silica gel eluted on a gradient from 100:0 to 90:10 hexanes/ethyl acetate to provide the title compound as a colorless oil (47 mg, 42%): $^1$H NMR (300 MHz, CDCl$_3$) δ7.95 (d, 1 H)7.69 (t, 1 H), 7.43–7.27 (m, 8 H), 7.23–7.19 (m, 6 H), 6.89 (t, 1 H), 6.84–6.80 (m, 3H), 6.75 (s, 1 H), 6.70 (d, 1 H), 5.29 (s, 2 H), 4.17–4.07 (m, 3 H), 3.83–3.66 (m, 3 H), 3.23 (q, 2 H), 2.93–2.64 (m, 6 H), 2.01–1.96 (m, 1 H), 1.72–1.63 (m, 3 H), 1.50–1.41 (m, 2 H), 0.95 (t, 3 H), 0.84 (s, 9 H), 0.07 (s, 3 H), 0.03 (s, 3 H); MS m/z 799.3 (MH$^+$).

Phenylmethyl 2-(butylamino)-4-((2R)-2-{[[(2S)-2{[(1,1-dimethylethyl)(dimethyl)silyl]oxy}-3-(phenyloxy)propyl](phenylmethyl)amino]methyl}-3,4-dihydro-2H-chromen-6-yl)benzoate (Example 194, 47 mg, 0.06 mmol) was added to a suspension of 10% Pd/C (47 mg) in methanol (3 mL). Ammonium formate (19 mg, 0.30 mmol, 5.0 eq.) was added, and the mixture was heated at reflux for 30 minutes. Solids were removed by filtration through Celite®, and the filtrate was concentrated in vacuo. The residue was redissolved in an excess of 4M HCl in dioxane at room temperature. After 30 minutes, the volatile components were removed by rotary evaporation, and the residue was washed with dichloromethane. After drying under vacuum, the title compound was collected as the dihydrochloride salt(25 mg, 73% overall yield): $^1$H NMR (300 MHz, CDCl$_3$) δ8.15 (d, 1 H), 7.52–7.46 (m, 4 H), 7.29(t, 2 H), 7.02–6.94 (m, 4 H), 4.55–4.48 (m, 1 H), 4.42–4.34 (m, 1 H), 4.13–4.01 (m, 2 H), 3.74–3,65 (m, 2 H), 3.59–3.39 (m, 4 H), 3.04–2.96 (m, 2 H), 2.21–2.15 (m, 1 H), 1.89–1.74 (m, 3 H), 1.57–1.45 (m, 2 H), 1.00 (t, 3 H); MS m/z 505.2 (MH$^+$ of the free base).

By employing the methods described above for Examples 193–195, the following were similarly prepared and characterized:

TABLE 16

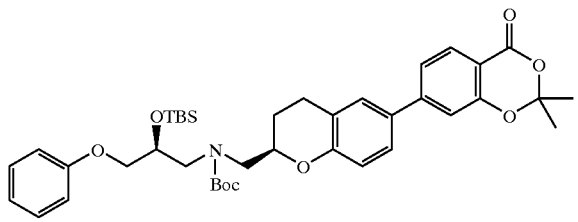

| Example No. | R″ | MS [MH+] | LC-MS RT (min) |
|---|---|---|---|
| 196 | —NHCH$_2$CH$_2$OMe | 507.3 | 2.34 |
| 197 | —NH-cyc-Hex | 531.3 | 2.62 |
| 198 | —NH$_2$ | 449.3 | 2.18 |
| 199 | —N(Et)$_2$ | 505.3 | 1.95 |
| 200 | —NH-i-Bu | 505.3 | 2.55 |
| 201 | —NH-cyc-Bu | 503.2 | 2.56 |
| 202 | 1-piperdinyl | 517.3 | 2.12 |

EXAMPLE 203

Preparation of 2,2-dimethyl-4-oxo-4H-1,3-benzodioxin-7-yl trifluoromethanesulfonate

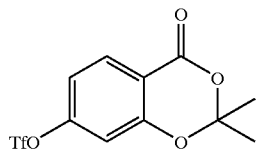

Trifluoroacetic acid (80 mL), trifluoroacetic anhydride (50 mL), and acetone (10 mL) were added to 2,4-dihydroxybenzoic acid (10.0 g, 64.9 mmol, 1.0 eq.) at 0° C. The reaction mixture was allowed to warm up slowly to room temperature and stirred for 48 hours. The mixture was then concentrated under reduced pressure. The resulting residue was washed with saturated sodium bicarbonate (100 mL), extracted with ethyl acetate (3×100 mL). The combined extracts were dried over magnesium sulfate, filtered and concentrated under reduced pressure to give crude product as yellow solid (9.2 g). The yellow crude material was treated with trifluoromethanesulfonic anhydride (8.8 mL, 52.11 mmol, 1.1 eq.) in the presence of pyridine (50 mL) at 0° C. for 8 hours. The resulting mixture was then diluted with distilled water (100 mL), extracted with ethyl acetate (3×50 mL) and washed with saturated sodium bicarbonate (60 mL) and brine (100 mL). The combined extracts were dried over magnesium sulfate, filtered and concentrated under reduced pressure to give brown oil. Purification by flash chromatography on a silica gel column (20%–40% ethyl acetate/hexanes) yielded the desired product as a white solid (8.3 g, 40%). $^1$H NMR (CDCl$_3$) δ8.08 (d, 1 H), 7.03 (d, 1 H), 6.94 (s, 1 H), 1.77 (s, 6H), GC-MS: 326 (M$^+$), retention time: 7.557 min.

EXAMPLE 204

Preparation of tert-butyl (2S)-2-{[tert-butyl (dimethyl)silyl]oxy}-3-phenoxypropyl{[(2S)-6-(2,2-dimethyl-4-oxo-4H-1,3-benzodioxin-7-yl)-3,4-dihydro-2H-chromen-2-yl]methyl}carbamate

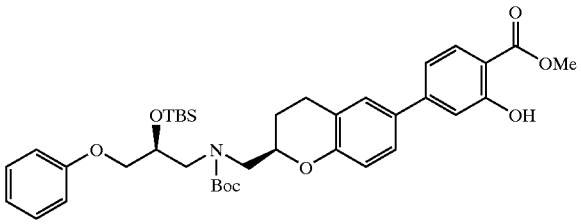

To a degassed solution of tert-butyl (2S)-2-{[tert-butyl (dimethyl)silyl]oxy}-3-phenoxypropyl{[(2S)-6-(4,4,5,5-tetramethyl-1,3,2-dioxaborolan-2-yl)-3,4-dihydro-2H-chromen-2-yl]methyl}carbamate (1.0 g, 1.53 mmol, 1.0 eq.) in toluene (12 mL) were added 2,2-dimethyl-4-oxo-4H-1,3-benzodioxin-7-yl trifluoromethanesulfonate (0.60 g, 1.84 mmol, 1.2 equiv.), dichloro[1,1'-bis(diphenylphosphino) ferrocene] palladium(II) dichloromethane adduct (0.18 g, 0.23 mmol, 0.15 eq.) and saturated sodium bicarbonate (8.0 mL) under argon atmosphere at room temperature. The reaction mixture was allowed to heat up at 80° C. under argon atmosphere for 18 hours. The mixture was then quenched with distilled water (10 mL) and extracted with ethyl acetate (3×10 mL). The combined extracts were washed with brine (20 mL), dried over magnesium sulfate, filtered and concentrated under reduced pressure to afford black oil. Purification by flash chromatography on a silica gel column (5%–15% ethyl acetate/hexanes) yielded the desired product as colorless oil (0.81 g, 76%). $^1$H NMR (CDCl$_3$) δ7.86 (d, 1 H), 7.27–6.78 (m, 11H), 4.20–3.85 (m, 2H), 3.81–3.40 (m, 4H), 3.37–3.20 (m, 2H), 2.80–2.21 (m, 2H), 1.95–1.84 (m, 1H), 1.64 (s, 7H), 1.39 (s, 9H), 0.81 (s, 9H), 0.020 (s, 6H).

EXAMPLE 205

Preparation of Methyl 4-((2S)-2-{[(tert-butoxycarbonyl)((2S)-2-{[tert-butyl(dimethyl)silyl]oxy}-3-phenoxypropyl)amino]methyl}-3,4-dihydro-2H-chromen-6-yl)-2-hydroxybenzoate To a solution of Example 204 (0.8 g, 1.14 mmol, 1.0 eq.) in methanol (10 mL) was added potassium carbonate (0.078 g, 0.57 mmol, 0.5 eq.) at room temperature. The reaction mixture was allowed to stir at room temperature for 18 hours and then concentrated under reduced pressure. The resulting residue was washed with distilled water (10 mL) and extracted with ethyl acetate (3×10 mL). The combined extracts were dried over magnesium sulfate, filtered and concentrated under reduced pressure to afford the desired product as pale yellow oil (0.75 g, 97%). $^1$H NMR (CDCl$_3$) δ10.68 (s, 1 H), 7.73 (d, 1H), 7.26–7.14 (m, 4H), 6.94 (dd, 1H), 6.86–6.75 (m, 5H), 4.21–4.02 (m, 2H), 3.83 (s, 3H), 3.80–3.56 (m, 4H), 3.40–3.21 (m, 2H), 2.80–2.67 (m, 2H), 1.95–1.92 (m, 1H), 1.65–1.60 (m, 1H), 1.38 (s, 9H), 0.83 (s, 9H), 0.001 (s, 6H).

EXAMPLE 206

Preparation of 4-[(2S)-2-({[(2S)-2-hydroxy-3-phenoxypropyl]amino}methyl)-3,4-dihydro-2H-chromen-6-yl]-2-methoxybenzoic acid

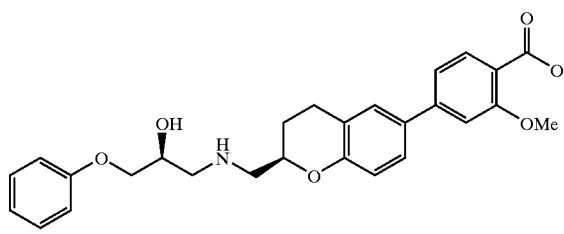

To a solution of Example 205 (0.085 g, 0.13 mmol, 1.0 eq.) in N,N-dimethylformamide (2.0 mL) were added iodomethane (0.012 ml, 0.19 mmol, 1.5 eq.) and potassium carbonate (0.026 mg, 0.19 mmol, 1.5 equiv.). The reaction mixture was stirred at room temperature for 16 hours. The mixture was diluted with distilled water (3 mL) and extracted with ethyl acetate (3×2 mL). The combined extracts were dried over magnesium sulfate, filtered and concentrated under reduced pressure. The resulting residue was then treated with 1M lithium hydroxide (0.5 mL) in the presence of methanol (1 mL) and stirred at room temperature for 3 hours. The mixture was neutralized by 1N hydrochloric acid and then extracted with ethyl acetate (3×2 mL). The extracts were concentrated under reduced pressure to give white solid. To this crude was added 4N hydrochloric acid in 1,4-dioxane (0.8 mL) and the mixture was stirred for 3 hours at room temperature. The resulting mixture was concentrated under reduced pressure to give white solid. Purification by HPLC yielded the desired TFA salt as a white solid (12 mg, 17%). $^1$H NMR (CDCl$_3$) δ8.18 (d, 1H), 7.41–7.20 (m, 5H), 7.12 (d, 1H), 7.00–6.82 (m, 4H), 4.64–4.48 (m, 2H), 4.11 (s, 3H), 4.16–3.94 (m, 4H), 3.58–3.31 (m, 2H), 2.98–2.81 (m, 2H), 2.21–2.06 (m, 1H); LC-MS: 464.3 (MH$^+$), retention time: 2.83 min.

By employing the methods described above for Examples 204–206, the following were similarly prepared and characterized:

TABLE 17

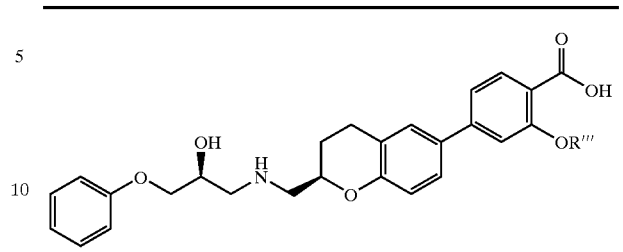

| Example No. | R''' | MS [MH$^+$] | HPLC RT (min) |
|---|---|---|---|
| 207 | —CH$_2$CH$_3$ | 478.8 | 2.3 |
| 208 | —CH$_2$CH$_2$CH$_3$ | 492.6 | 2.43 |
| 209 | —CH$_2$CH(CH$_3$)$_2$ | 506.7 | 2.53 |
| 210 | —CH$_2$CH$_2$OCH$_3$ | 508.7 | 2.24 |
| 211 | —CH(CH$_3$)$_2$ | 492.6 | 2.40 |
| 212 | —CH$_2$CH$_2$CH$_2$CH$_3$ | 506.6 | 2.53 |

EXAMPLE 213

Preparation of 2-hydroxy-4-[(2S)-2-({[(2S)-2-hydroxy-3-phenoxypropyl]amino}methyl)-3,4-dihydro-2H-chromen-6-yl]benzoic acid

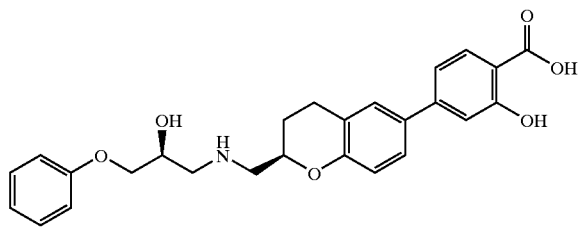

To a solution of Example 204 in tetrahydrofuran (0.5 mL) was added 1N aqueous hydrochloric acid (2 mL) and 4N hydrochloric acid in 1,4-dioxane (1.5 mL) at room temperature. The reaction mixture was allowed to heat up at 70° C. for 5 hours and cool down to room temperature. The mixture was then concentrated under reduced pressure to afford the desired HCl salt as white solid. (0.032 g, 94%). $^1$H NMR (DMSO) δ8.87 (s, 1H), 7.74 (d, 1H), 7.47–7.42 (m, 3H), 7.28–7.22 (m, 2H), 7.13 (d, 1H), 6.91–6.82 (m, 4H), 5.83 (d, 1H), 4.71–4.57 (m, 1H), 4.30–4.18 (m, 1H), 3.93 (t, 2H), 3.15–2.91 (m, 2H), 2.82–2.71 (m, 2H), 2.08–1.98 (m, 1H), 1.78–1.61 (m 1H); (MH$^+$), retention time: 2.25 min.

EXAMPLE 214

Preparation of Methyl 4-((2S)-2-{[(tert-butoxycarbonyl)((2S)-2-{[tert-butyl(dimethyl)silyl]oxy}-3-phenoxypropyl)amino]methyl}-3,4-dihydro-2H-chromen-6-yl)-2-{[(trifluoromethyl)sulfonyl]methoxy}benzoate

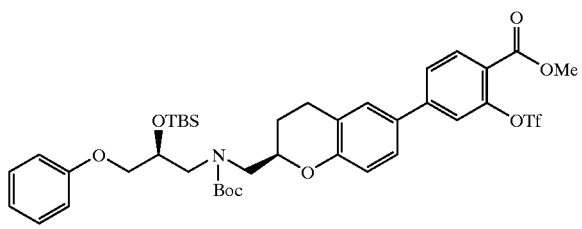

To a solution of Example 205 (0.75 g, 1.11 mmol, 1.0 eq.) in pyridine (5 mL) was added trifluoromethanesulfonic anhydride (0.21 mL, 1.22 mmol, 1.1 eq.) at 0° C. The reaction mixture was stirred at 0° C. for 8 hours and then warmed up to room temperature. The resulting mixture was diluted with distilled water (10 mL), extracted with ethyl acetate (3×8 mL). The combined extracts were washed with saturated sodium bicarbonate (60 mL) and brine (100 mL), dried over magnesium sulfate, filtered and concentrated under reduced pressure to give brown oil. Purification by flash chromatography on a silica gel column (5%–10% ethyl acetate/hexanes) yielded the desired product as colorless oil (0.68 g, 76%). LC-MS: 808.8 (MH$^+$), retention time: 5.35 min.

EXAMPLE 215

Preparation of 5-[(2S)-2-({[(2S)-2-hydroxy-3-phenoxypropyl]amino}methyl)-3,4-dihydro-2H-chromen-6-yl]-1,1'-biphenyl-2-carboxylic acid (13)

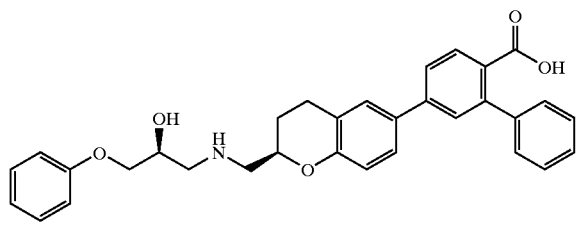

To a degassed solution of methyl 4-((2S)-2-{[(tert-butoxycarbonyl)((2S)-2-{[tert-butyl(dimethyl)silyl]oxy}-3-phenoxypropyl)amino]methyl}-3,4-dihydro-2H-chromen-6-yl)-2-{[(trifluoromethyl)sulfonyl]methoxy}benzoate (Example 214, 0.090 g, 0.11 mmol, 1.0 eq.) in toluene (1.0 mL) were added phenylboronic acid (0.018mg, 0.14 mmol, 1.3 eq.), dichloro[1,1'-bis(diphenylphosphino)ferrocene]palladium(II) dichloromethane adduct (0.014 g, 0.017 mmol, 0.15 eq.), and saturated sodium bicarbonate (1.0 mL) under argon atmosphere at room temperature. The reaction mixture was allowed to heat up at 80° C. under argon atmosphere for 18 hours. The mixture was diluted with distilled water (3 mL) and extracted with diethyl ether (3×2 mL). The combined extracts were dried over magnesium sulfate, filtered and concentrated under reduced pressure. The resulting residue was then treated with 1M lithium hydroxide (1.5 mL) in the presence of methanol (0.5 mL) and tetrahydrofuran (0.5 mL) and stirred at 50° C. for 15 hours. The mixture was neutralized by 1N hydrochloric acid and then extracted with ethyl acetate (3×2 mL). The extracts were concentrated under reduced pressure to give white solid. To this crude was added 4N hydrochloric acid in 1,4-dioxane (1.5 mL) and the mixture was stirred for 8 hours at room temperature. The resulting mixture was concentrated under reduced pressure to give white solid. Purification by HPLC followed by a HCl substitution yielded the desired HCl salt as a white solid (20.2 mg, 33%). $^1$H NMR (DMSO)) δ7.81 (d, 1H), 7.67 (dd, 1H), 7.54–7.51 (m, 3H), 7.43–7.27 (m, 6H), 6.98–6.89 (m, 5H), 5.88 (d, 1H), 4.53–4.42 (m, 1H), 4.38–4.21 (m, 1H), 3.98 (t, 2H), 3.26–3.20 (m, 2H), 2.86–2.83 (m, 2H), 2.89–2.84 (d, 1H), 1.82–1.68 (m, 1H); LC-MS: 510.4 (MH$^+$), retention time: 2.42 min.

By employing the methods described above for Examples 214 and 215, the following were similarly prepared and characterized.

TABLE 18

| Example No. | R'''' | MH$^+$ (Obs.) | HPLC RT (min.) |
|---|---|---|---|
| 216 | p-Cl | 544.5 | 2.56 |
| 217 | p-Me | 524.5 | 2.51 |
| 218 | o-OMe | 540.7 | 2.39 |
| 219 | p-OMe | 540.7 | 2.43 |
| 220 | p-t-Bu | 566.3 | 2.79 |

The further examples below describe combinatorial/parallel methods for preparing compounds of the present invention in matrix fashion.

EXAMPLE 221

4-[(2R)-2-({[(2S)-3-(2-chlorophenoxy)-2-hydroxypropyl]amino}methyl)-3,4-dihydro-2H-chrome-6-yl]benzoic acid

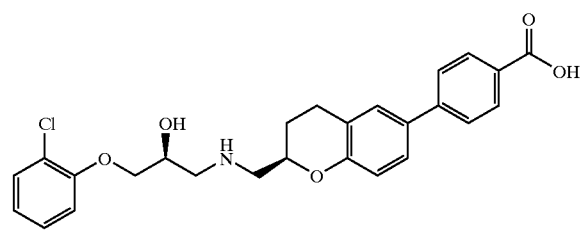

In a 8-mL screw-cap vial, 6-(4-methoxycarbonylphenyl)-(R)-chroman-2-methylamine [methyl 4-[(2R)-2-(aminomethyl)-3,4-dihydro-2H-chromen-6-yl]benzoate] (30.0 mg, 0.1 mmol), (2S)-2-[(2-chlorophenoxy)methyl]oxirane (18.5 mg, 0.1 mmol) were dispensed and 500 μL of dioxane and 100 μL of water were added to each well. The mixture was heated at 80° C. with mixing by orbital shaking for 2 days. After the mixture was allowed to cool to room temperature, the solvent was removed under reduced pressure by using a multiple sample evaporator (GeneVac). The residue was then heated in 2 M lithium hydroxide solution (1 mL) in methanol and water (3:1) at 60° C. overnight. After allowing the reaction mixture to cool to room temperature, 2 N hydrochloric acid (1.1 mL) was slowly added to each well. Precipitate was formed in the vial. The solvent was removed under reduced pressure (GeneVac). The residue was redissolved in 1 mL MeOH and purified by preparative reversed phase HPLC, using aqueous MeCN containing 0.1% trifluoroacetic acid as eluant, to give 10.3 mg of 4-[(2R)-2-({[(2S)-3-(2-chlorophenoxy)-2-hydroxypropyl]amino}methyl)-3,4-dihydro-2H-chromen-6-yl]benzoic acid as the trifluoroacetate salt (white solid, 22% yield). $^1$H NMR (400 MHz, CDCl$_3$) δ7.95(d, 2 H), 7.60 (d, 2 H), 7.10–7.40 (m, 4 H), 7.00 (d, 1 H), 6.85 (m, 2 H), 4.35 (m, 2 H), 4.10 (m, 2 H), 3.40 (m, 4 H), 2.10 (m, 1 H), 1.80 (m, 1 H); LC-MS m/z 468.5 (MH$^+$), ret. time 2.23 min. Calculated exact mass for C$_{26}$H$_{26}$ClN$_5$=467.2).

In a similar manner to the procedure described in Example 221, using commercially-available or custom-prepared epoxides, the following compounds were prepared:

TABLE 19

| Example No. | STRUCTURE | LC-MS RT (min) | MS [M + H]$^+$ |
|---|---|---|---|
| 222 | 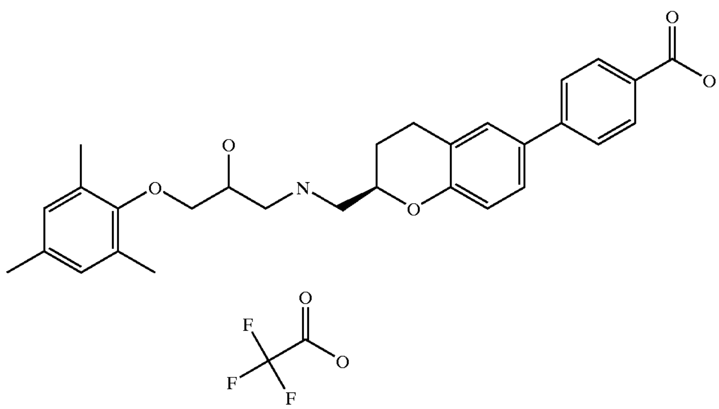 | 2.26 | 476 |
| 223 | 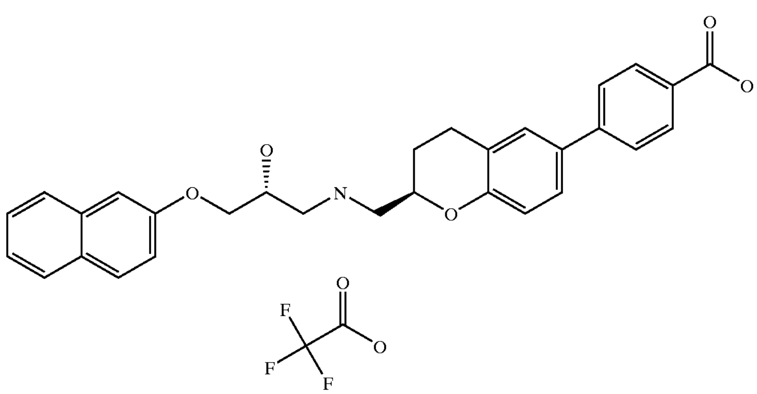 | 2.27 | 484 |
| 224 | 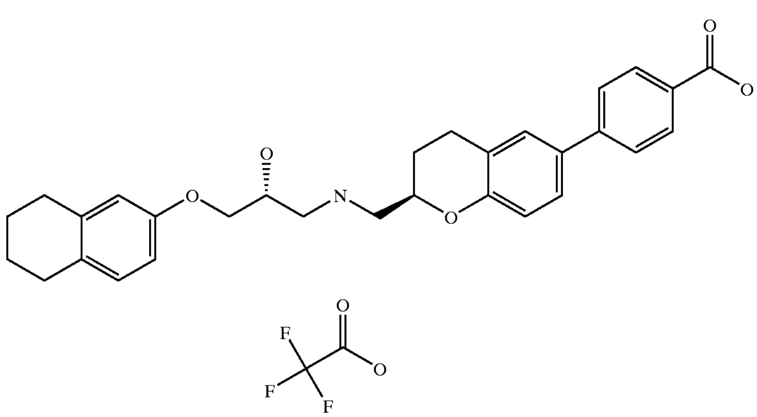 | 2.30 | 488 |

TABLE 19-continued
| Example No. | STRUCTURE | LC-MS RT (min) | MS [M + H]+ |
|---|---|---|---|
| 225 | 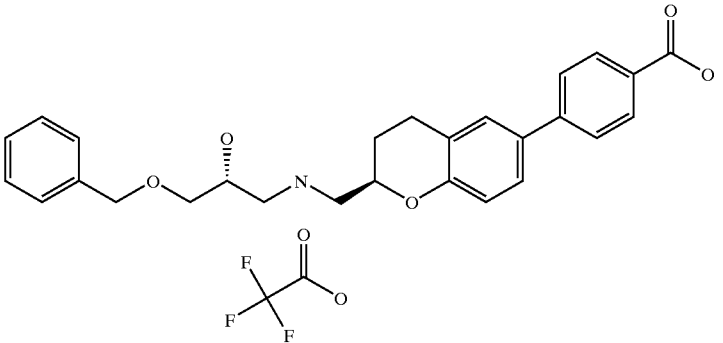 Chiral | 2.04 | 448 |
| 226 | 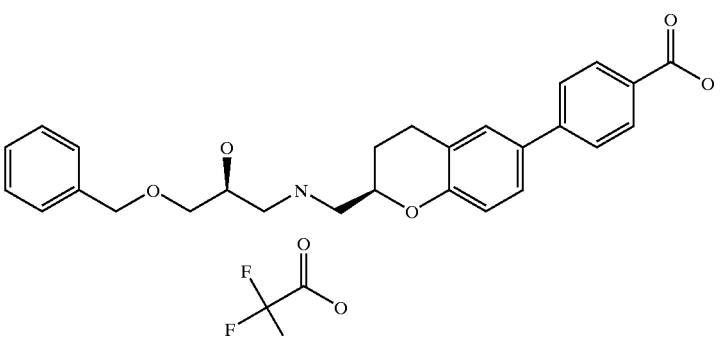 Chiral | 2.08 | 448 |
| 227 | 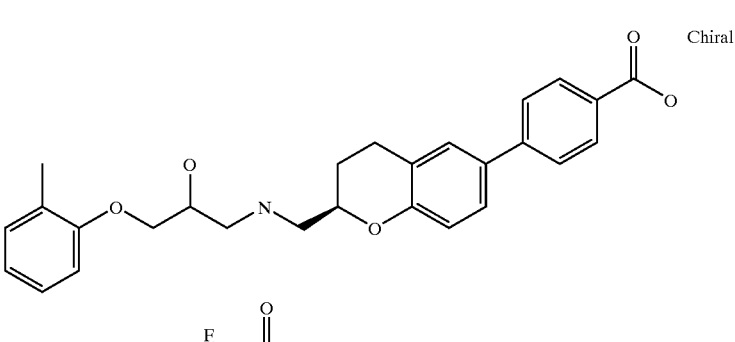 Chiral | 2.14 | 448 |
| 228 | 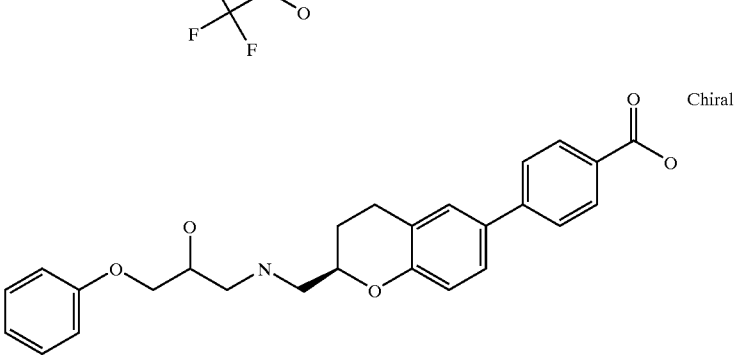 Chiral | 2.15 | 434 |

TABLE 19-continued

| Example No. | STRUCTURE | LC-MS RT (min) | MS [M + H]+ |
|---|---|---|---|
| 229 | 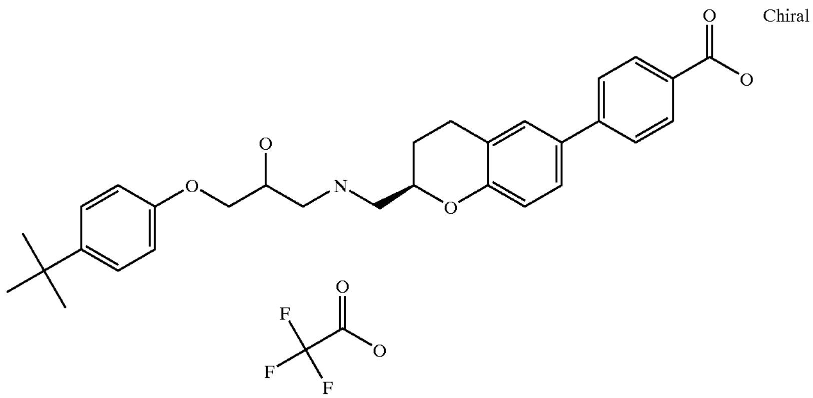 | 2.47 | 490 |
| 230 | 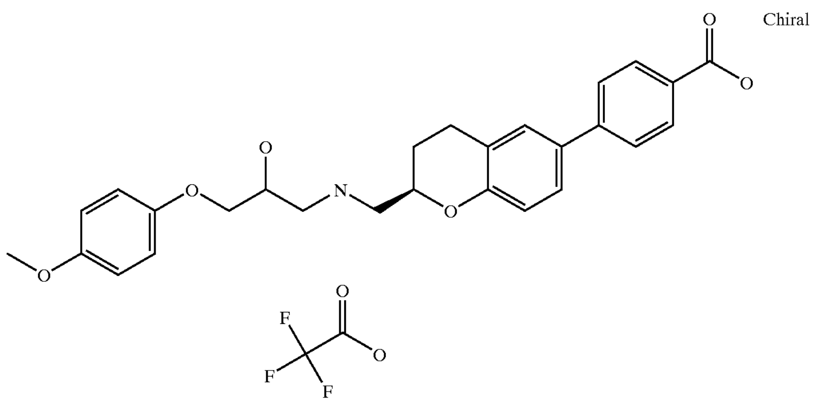 | 2.09 | 464 |
| 231 | 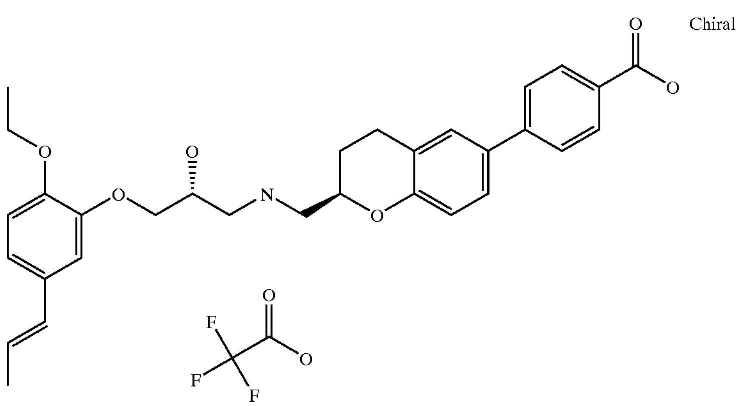 | 2.41 | 518 |

| Example No. | STRUCTURE | LC-MS RT (min) | MS [M + H]+ |
|---|---|---|---|
| 232 | 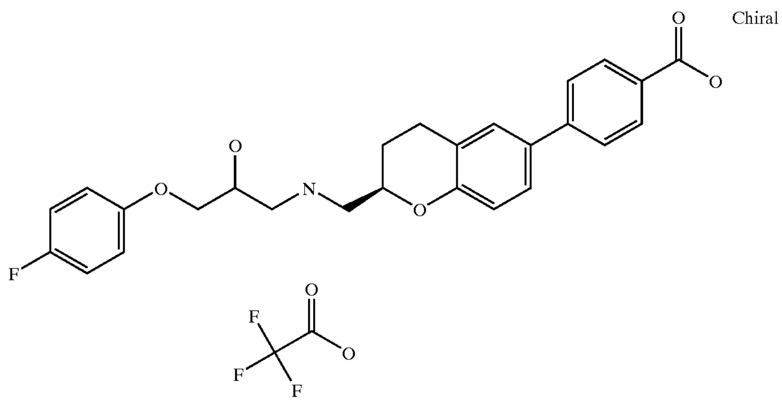 | 2.15 | 452 |
| 233 | 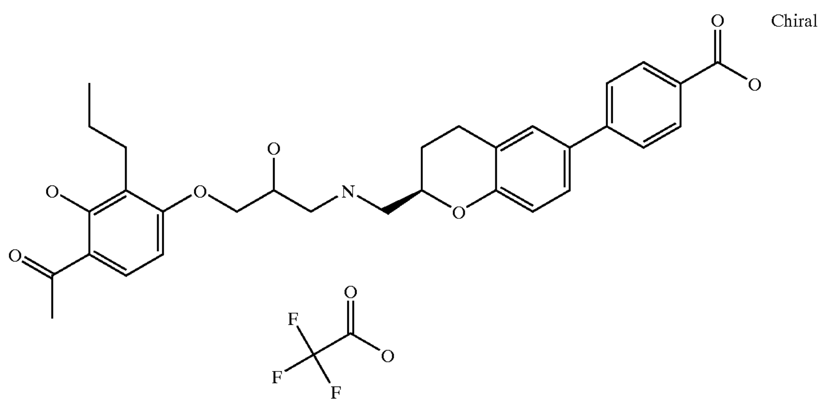 | 2.41 | 534 |
| 234 | 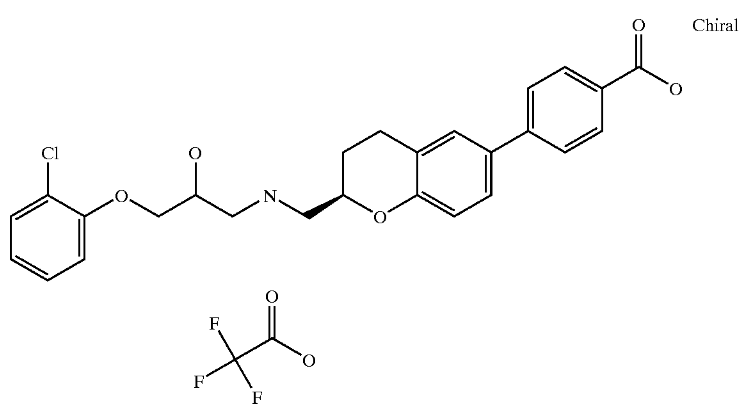 | 2.15 | 468 |

TABLE 19-continued
| Example No. | STRUCTURE | LC-MS RT (min) | MS [M + H]+ |
|---|---|---|---|
| 235 | 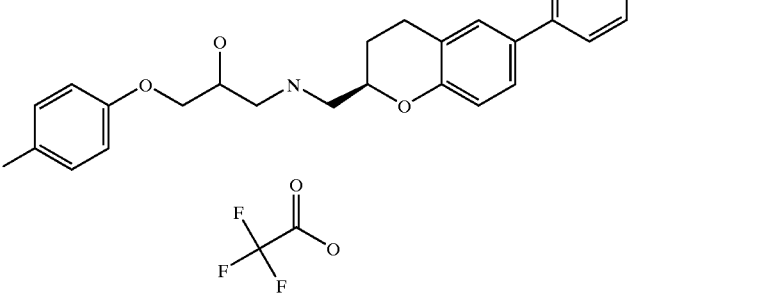 | 2.27 | 512 |
| 236 | 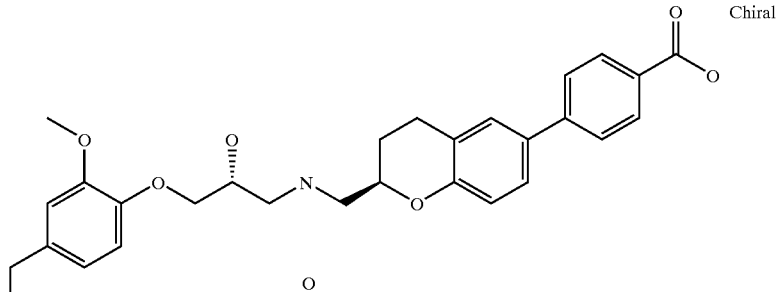 | 2.29 | 504 |
| 237 | 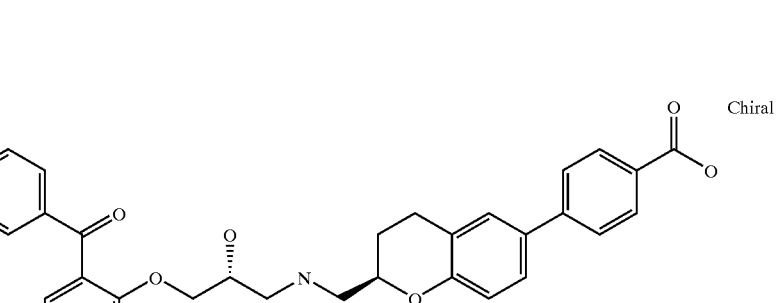 | 2.31 | 568 |

TABLE 19-continued
| Example No. | STRUCTURE | LC-MS RT (min) | MS [M + H]+ |
|---|---|---|---|
| 238 | 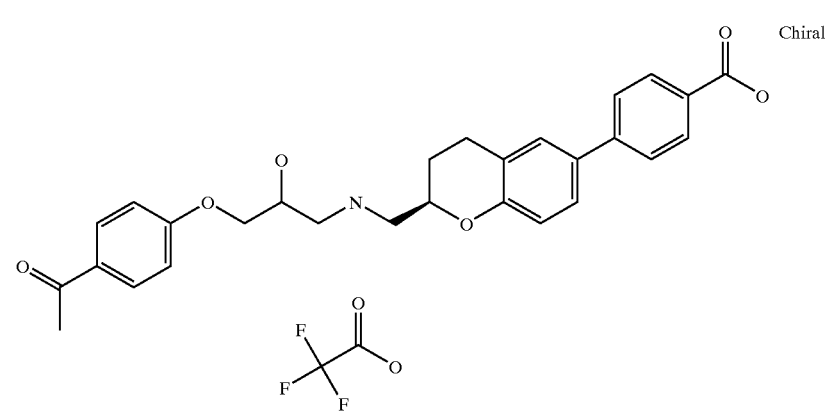 | 2.03 | 476 |
| 239 | 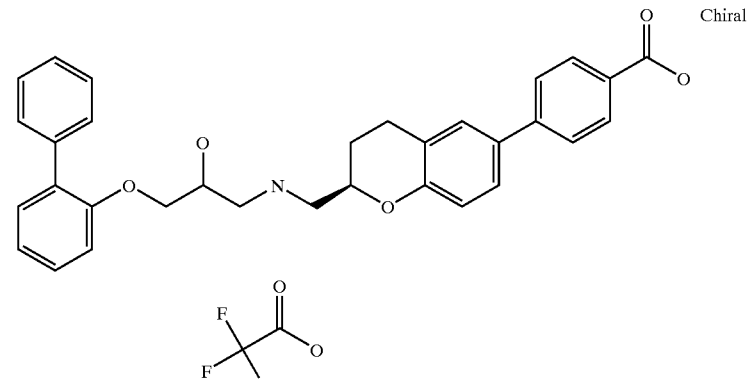 | 2.37 | 510 |
| 240 | 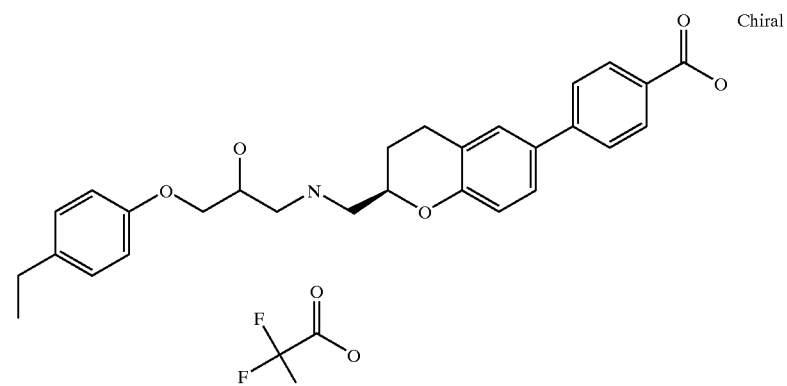 | 2.26 | 462 |

TABLE 19-continued
| Example No. | STRUCTURE | LC-MS RT (min) | MS [M + H]+ |
|---|---|---|---|
| 241 | 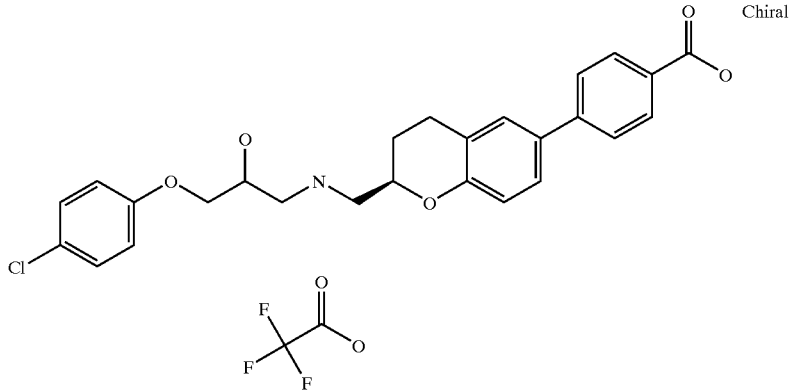 | 2.19 | 468 |
| 242 | 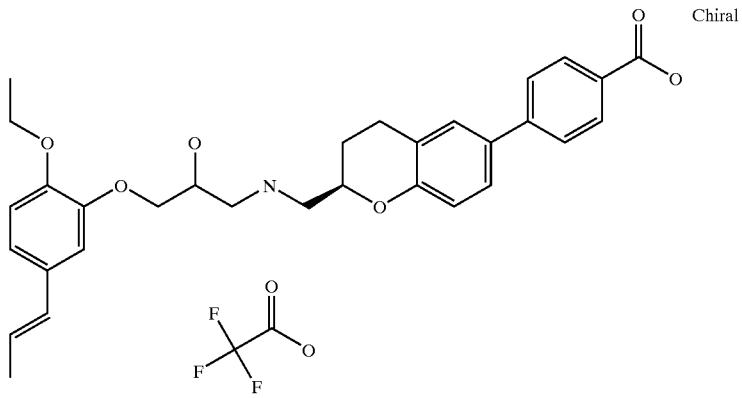 | 2.44 | 518 |
| 243 | 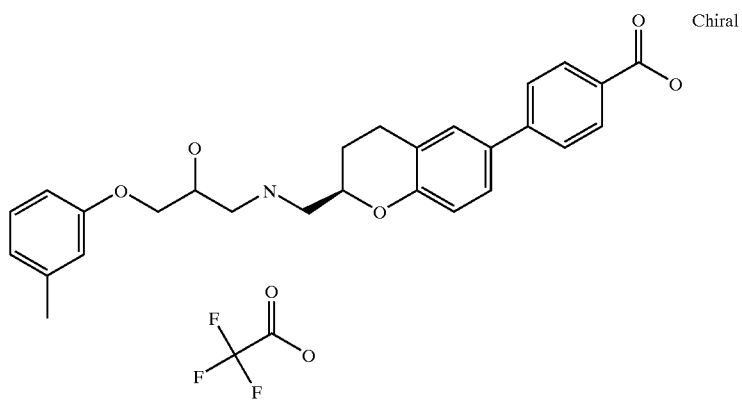 | 2.23 | 448 |

TABLE 19-continued
| Example No. | STRUCTURE | LC-MS RT (min) | MS [M + H]+ |
|---|---|---|---|
| 244 | 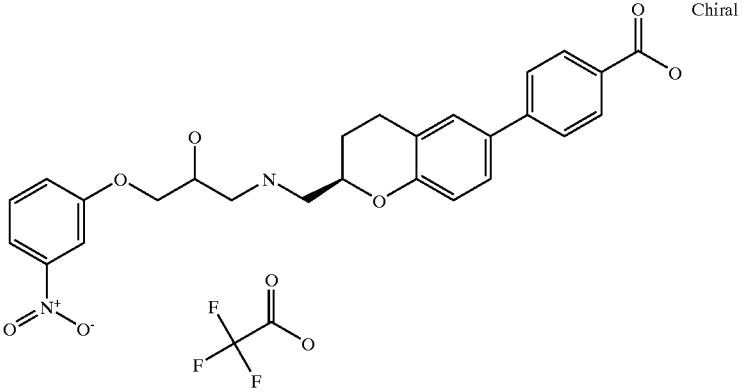 | 2.15 | 479 |
| 245 | 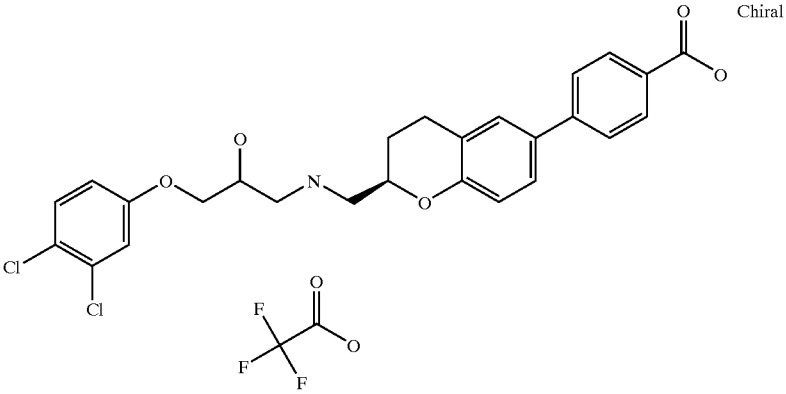 | 2.39 | 502 |
| 246 | 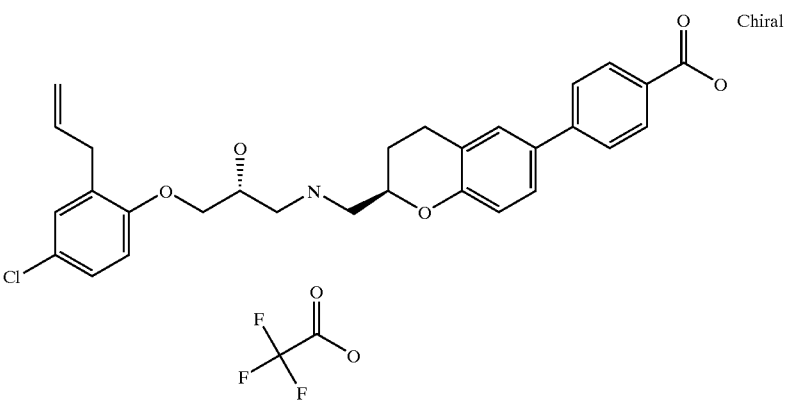 | 2.46 | 508 |

TABLE 19-continued
| Example No. | STRUCTURE | LC-MS RT (min) | MS [M + H]+ |
|---|---|---|---|
| 247 | 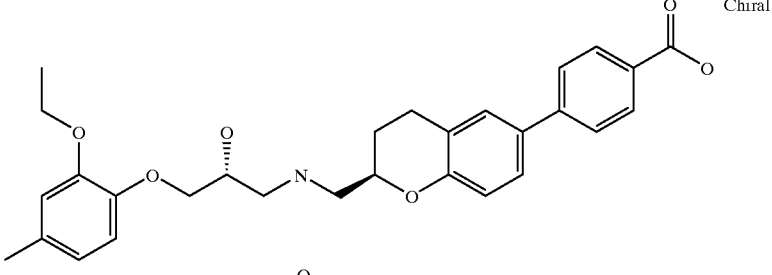 | 2.24 | 492 |
| 248 | 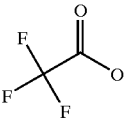 | 2.63 | 572 |
| 249 | 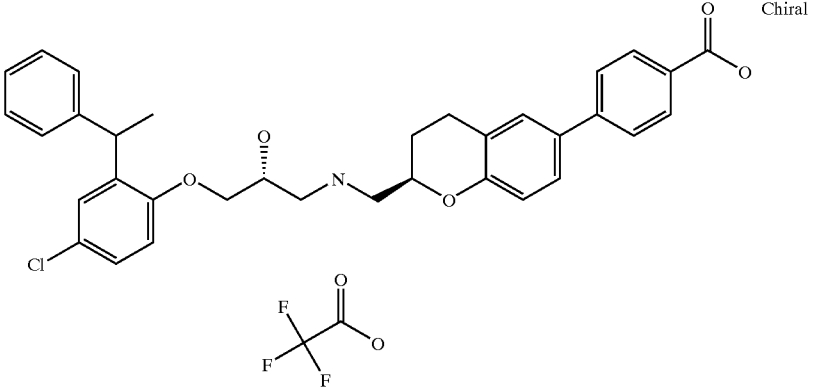 | 2.49 | 490 |

TABLE 19-continued
| Example No. | STRUCTURE | LC-MS RT (min) | MS [M + H]+ |
|---|---|---|---|
| 250 | 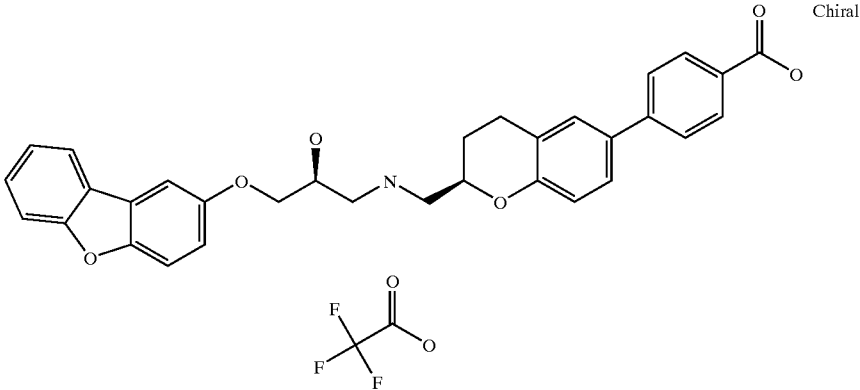 | 2.42 | 524 |
| 251 | 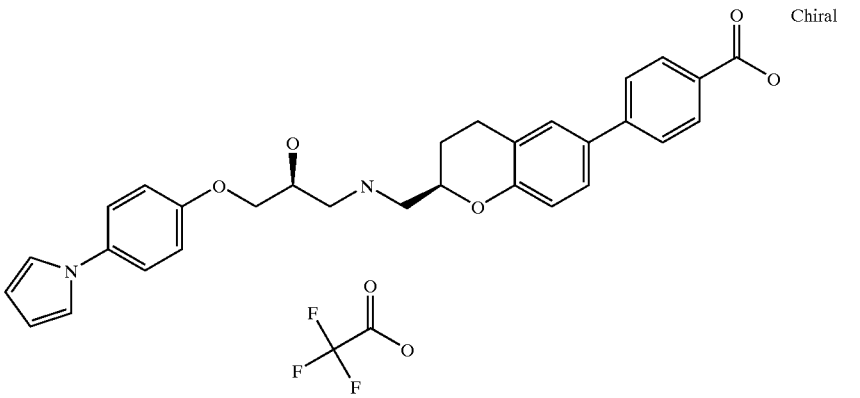 | 2.37 | 499 |
| 252 | 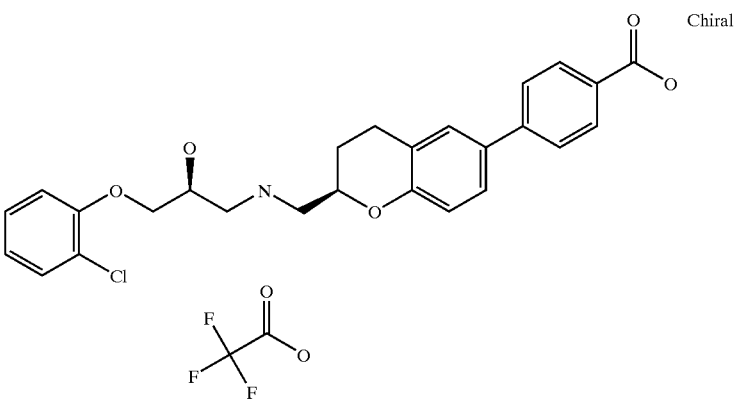 | 2.24 | 468 |

TABLE 19-continued

| Example No. | STRUCTURE | LC-MS RT (min) | MS [M + H]+ |
|---|---|---|---|
| 253 | 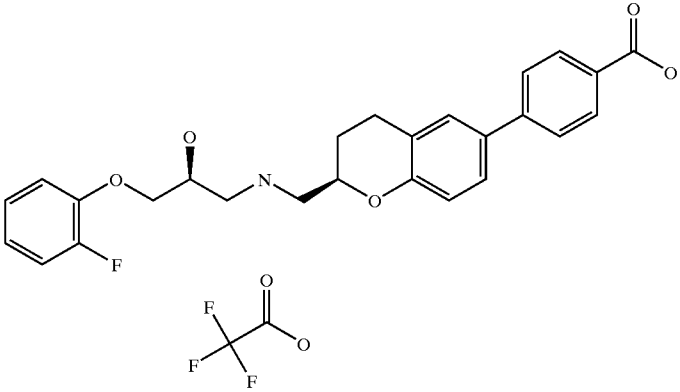 Chiral | 2.18 | 452 |
| 254 | 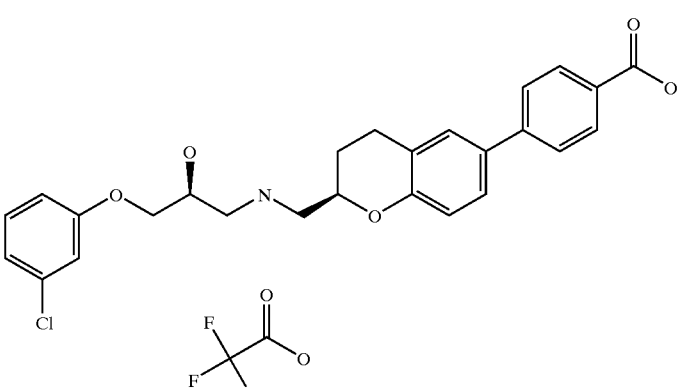 Chiral | 2.27 | 468 |

EXAMPLE 255

Reaction of Chroman-2-Methylamines with Epoxides

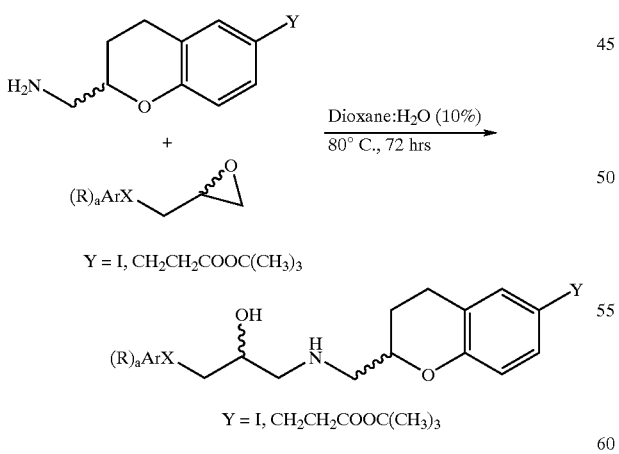

The apparatus used was as described in the general experimentals methods above. In a typical procedure, solutions of a 6-(R)-chroman-2-methylamine (Example 10 or 13) and an epoxide (commercially-available or custom-prepared as described for Examples 15–19) were freshly prepared as a 0.5 M solution in dioxane. To each reaction well in a polypropylene reaction block was added a solution of the desired amine (200 μL, 0.1 mmol), a solution of the desired epoxide (200 μL, 0.1 mmol), and 500 μL of dioxane as well as 100 μL of water. The reaction block was sealed with rubber gaskets and clamped, then heated at 80° C. for 72 hrs, with mixing by rotation. After allowing the reaction block to cool to room temperature, the block was disassembled, and the reaction well contents were filtered into a collection 96-well deep-well microtiter plate, washing with 2 portion of 200 μL of dioxane. The filtrate solutions were evaporated to dryness using a multiple sample centrifugal vacuum evaporator. Products were analyzed for purity and correct identity by LC/MS.

EXAMPLE 256

Hydrolysis of t-Butyl esters

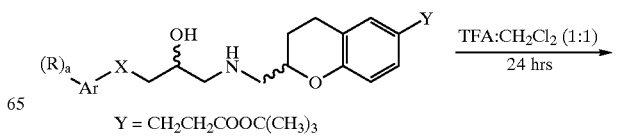

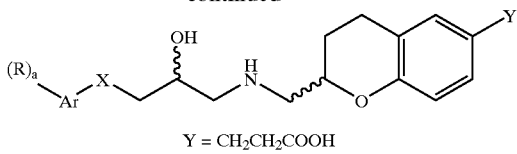

Y = CH₂CH₂COOH

To each product obtained by the procedure of Example 255 where R=CH₂CH₂COOC(CH₃)₃, methylene chloride (500 μL) and trifluoroacetic acid (500 μL) were added. The 96-well deep-well microtiter plate containing these solutions was sealed with polypropylene sealing film by using a plate heat-sealer (Marsh Bio Products, Rochester, N.Y.). The microtiter plate was positioned on an orbital shaker, and the plate was subjected to gentle shaking at room temperature for 24 hours. The progress of hydrolysis was monitored by LC/MS. The solvent was then removed by using a multiple sample centrifugal vacuum evaporator. Methanol (1 mL) was then added to each well and the solvent removed in vacuo again to ensure the complete removal of trifluoroacetic acid from the product. Products were analyzed for purity and correct identity by LC/MS.

Utilizing the procedures of Examples 255 and 256 and substituting the appropriate starting materials, the following compounds were prepared and characterized in similar fashion and are listed in Table 20.

TABLE 20

6-Substituted (2R)-2-({[(2S)-2-Hydroxy-3-aryloxypropyl]amino}methyl)-3,4-dihydro-2H-chromenes

| Example No. | Structure | LC-MS RT (min) | MS [M + H]⁺ |
|---|---|---|---|
| 257 | 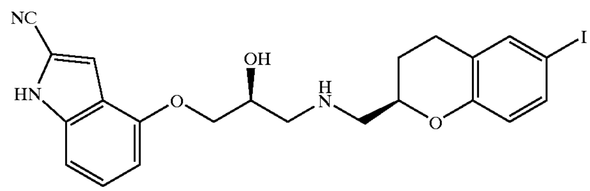 | 2.59 | 504 |
| 258 | 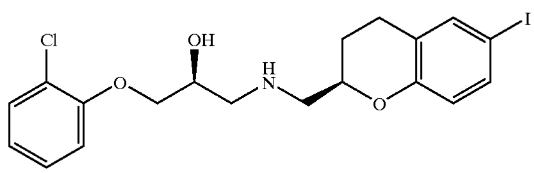 | 2.74 | 474 |
| 259 | 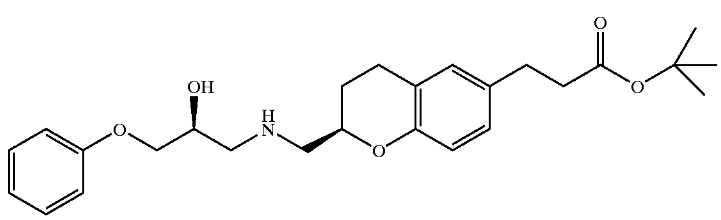 | 2.74 | 442 |
| 260 | 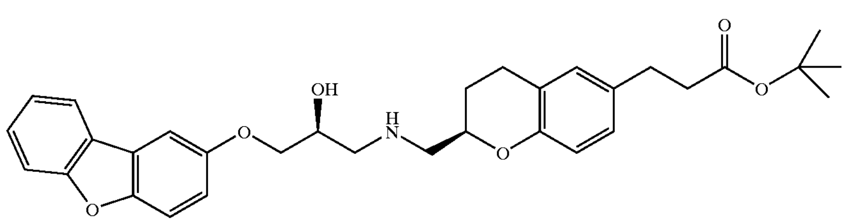 | 3.03 | 532 |
| 261 | 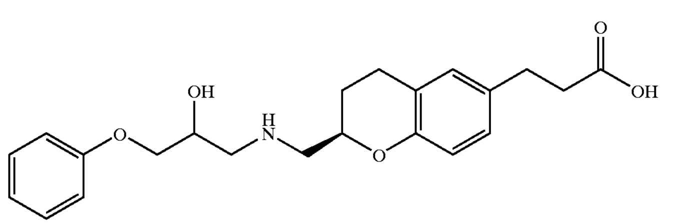 | 2.22 | 386 |

TABLE 20-continued

6-Substituted (2R)-2-({[(2S)-2-Hydroxy-3-aryloxypropyl]amino}methyl)-3,4-dihydro-2H-chromenes

| Example No. | Structure | LC-MS RT (min) | MS [M + H]+ |
|---|---|---|---|
| 262 | 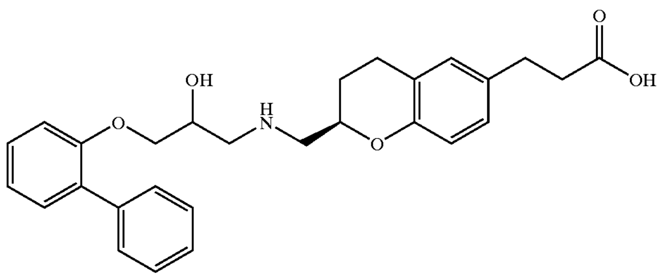 | 2.56 | 462 |

EXAMPLES 263–264

For certain compounds, the preparation steps of Examples 255–256 were repeated using the same procedure on larger scale (0.7 mmol), and the product was purified by preparative reverse-phase HPLC (a YMC Pro C18 150 mm×20 mm column was used, at 15 mL/min with gradient elution from 90% solvent A to 100% solvent B. Solvent A was water containing 0.02% trifluoroacetic acid. Solvent B was acetonitrile containing 0.02% trifluoroacetic acid). Thus were obtained the compounds of Examples 263–266 below.

EXAMPLE 263

Preparation of 3-[(2R)-2-({[(2S)-2-Hydroxy-3-phenoxypropyl]amino}methyl)-3,4-dihydro-2H-chromen-6-yl]propanoic acid $^1$H NMR (300 MHz, CDCl$_3$) δ9.50 (bs, 1 H), 8.80 (bs, 1 H), 6.70–7.30 (m, 8 H), 4.55 (m, 1 H), 4.45 (m, 1 H), 3.90 (m, 2 H), 3.30 (m, 4 H), 2.70 (m, 4 H), 2.40 (m, 2 H), 1.90 (m, 1 H), 1.65 (m, 1 H); LC/MS m/z 386 (MH$^+$, ret. time=2.30 min, calc'd exact mass for C$_{22}$H$_{27}$NO$_5$=385.19).

EXAMPLE 264

Preparation of 3-[(2R)-2-({[(2S)-3-(2-chlorophenoxy)-2-hydroxypropyl]amino}methyl)-3,4-dihydro-2H-chromen-6-yl]propanoic acid $^1$H NMR (300 MHz, CDCl$_3$) δ9.50 (bs, 1 H), 8.80 (bs, 1 H), 7.35 (d, 1 H), 7.20 (t, 1 H), 6.65–7.00 (m, 5 H), 4.60 (m, 1 H), 4.40 (m, 1 H), 4.00 (m, 2 H), 3.20–3.60 (m, 4 H), 2.75 (m, 4 H), 2.50 (m, 2 H), 1.90 (m, 1 H), 1.65 (m, 1 H); LC/MS m/z 420 (MH$^+$, ret. time=2.41 min, calc'd exact mass for C$_{22}$H$_{26}$ClNO$_5$=419.15).

EXAMPLE 265

Preparation of 3-[(2R)-2-({[(2S)-3-(2-Fluorophenoxy)-2-hydroxypropyl]amino}methyl)-3,4-dihydro-2H-chromen-6-yl]propanoic acid

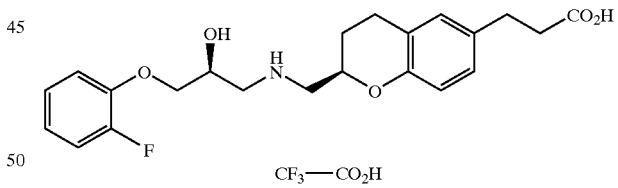

$^1$H NMR (300 MHz, CDCl$_3$) δ9.50 (bs, 1 H), 8.90 (bs, 1 H), 7.35 (d, 1 H), 6.60–7.10 (m, 7 H), 4.50 (m, 1 H), 4.30 (m, 1 H), 3.90 (m, 2 H), 3.20–3.60 (m, 4 H), 2.75 (m, 4 H), 2.50 (m, 2 H), 1.90 (m, 1 H), 1.65 (m, 1 H); LC/MS m/z 404 (MH$^+$, ret. time=2.34 min, calc'd exact mass for C$_{22}$H$_{26}$FNO$_5$=403.18).

Additional examples were prepared and characterized in the manner of Examples 263–265 and are listed in Table 21.

TABLE 21
[(2R)-2-({[(2S)-2-Hydroxy-3-aryloxypropyl]amino}methyl)-3,4-dihydro-2H-chromen-6-yl]substituted carboxylic acids
| Example No | Structure | LC-MS RT (min) | MS [M + H]+ |
|---|---|---|---|
| 266 | 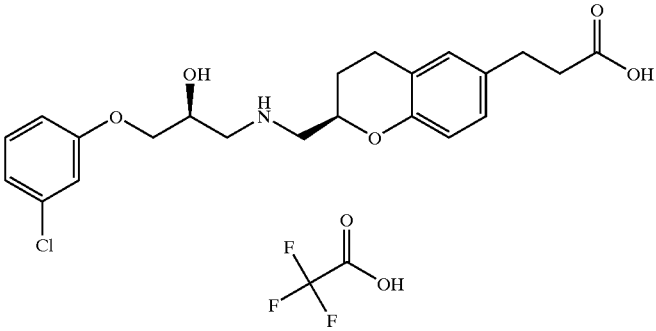 | 2.48 | 420 |
| 267 | 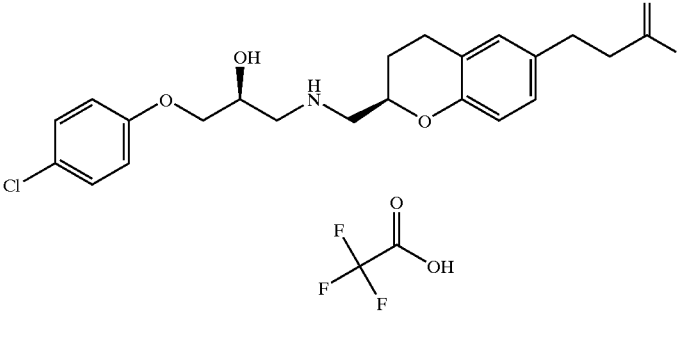 | 2.48 | 420 |
| 268 | 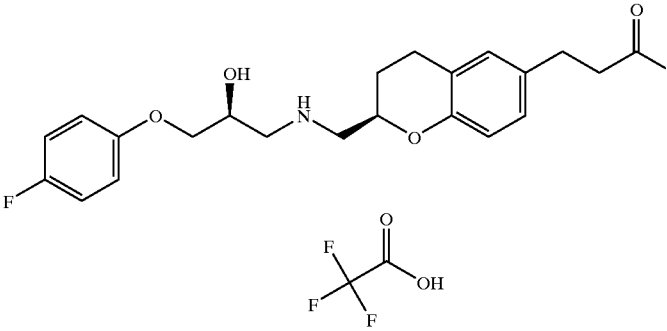 | 2.34 | 404 |
| 269 | 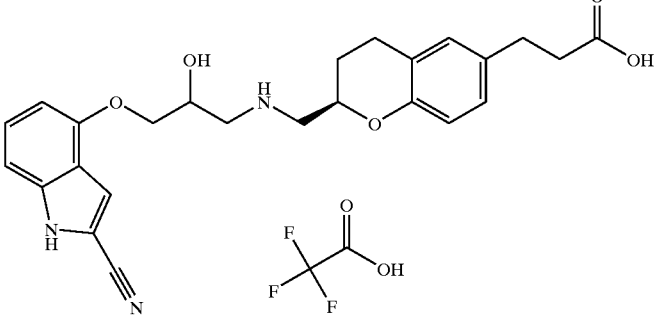 | 2.23 | 450 |

TABLE 21-continued

[(2R)-2-({[(2S)-2-Hydroxy-3-aryloxypropyl]amino}methyl)-
3,4-dihydro-2H-chromene-6-yl]substituted carboxylic acids

| Example No | Structure | LC-MS RT (min) | MS [M + H]+ |
|---|---|---|---|
| 270 | 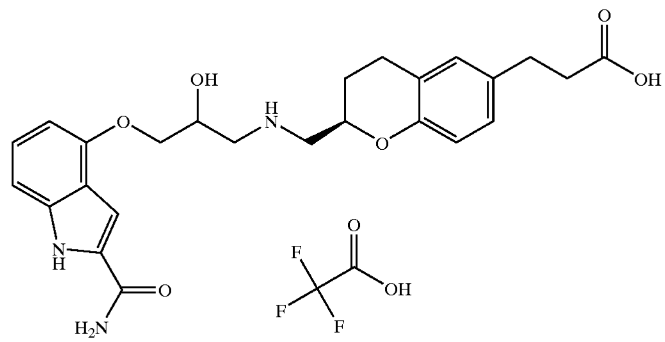 | 2.04 | 468 |

EXAMPLES 271–275

Parallel Synthesis Method via in situ silyation

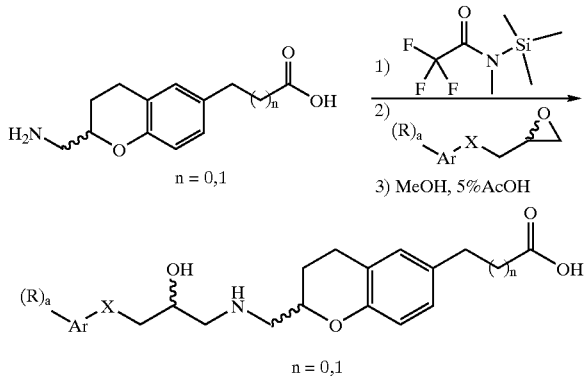

n = 0,1

The apparatus used was as described in the general experimentals methods above. In a typical procedure, 0.5 M fresh dioxane solutions of 6-carboxymethyl (or 6-carboxyethyl)-chroman-2-methylamine n=0, 1) (Examples 6 and 13) and epoxides commercially-available or custom prepared as described for Examples 15–19 were prepared. To the 0.5 M solution of each amine, N-methyl-N-(trimethylsilyl)trifluoroacetamide (MSTFA, 100 μL, 0.6 mmol) was added for every 0.1 mmol of amine (6 eq.), and the mixture was agitated at room temperature for 1 hour. To each reaction well in a polypropylene reaction block was added a solution of the above mixture (300 μL, contains 0.1 mmol of the chroman-2-methylamine and 0.6 mmol of MSTFA), a solution of the desired epoxide (200 μL, 0.1 mmol), and 300 μL of dioxane. The reaction block was sealed with rubber gaskets and clamped, then heated at 80° C. for 72 hrs, with mixing by rotation. After allowing the reaction block to cool to room temperature, 800 μl of methanol with 5% acetic acid was added to each well. After rotating 30 minutes, the block was disassembled, and the reaction well contents were filtered into a collection 96-well deep-well microtiter plate. The filtrate solutions were evaporated to dryness using a multiple sample centrifugal vacuum evaporator. Products were analyzed for purity and correct identity by LC/MS. Examples 271–275 were prepared and characterized by this method are summarized in Table 22.

TABLE 22

[(2R)-2-({[(2S)-2-Hydroxy-3-aryloxypropyl]amino}methyl)-
3,4-dihydro-2H-chromene-6-yl]acetic acids

| Example No. | Structure | LC-MS RT (min) | MS [M + H]+ |
|---|---|---|---|
| 271 | 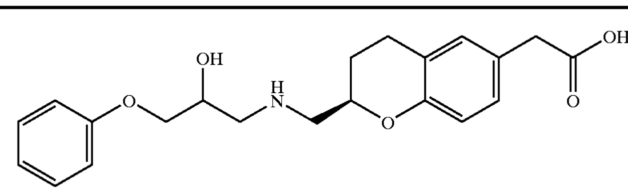 | 2.04 | 372 |

TABLE 22-continued
[(2R)-2-({[(2S)-2-Hydroxy-3-aryloxypropyl]amino}methyl)-3,4-dihydro-2H-chromene-6-yl]acetic acids
| Example No. | Structure | LC-MS RT (min) | MS [M + H]+ |
|---|---|---|---|
| 272 | 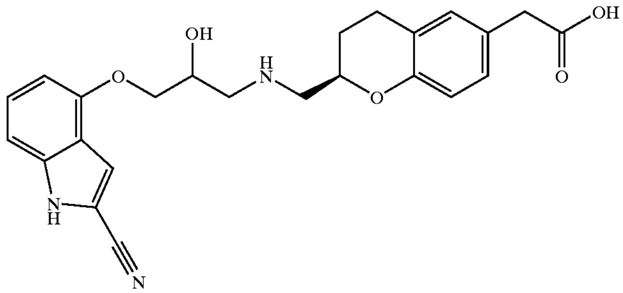 | 2.08 | 436 |
| 273 | 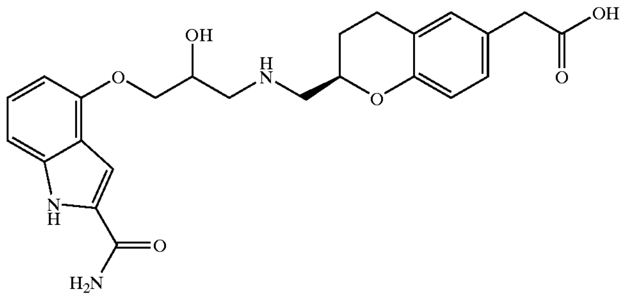 | 1.82 | 454 |
| 274 | 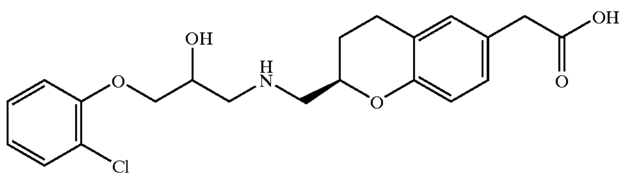 | 2.15 | 406 |
| 275 | 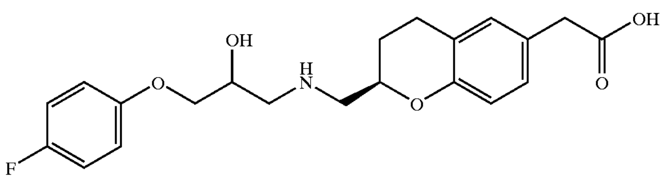 | 2.12 | 390 |
EXAMPLES 276–286
Parallel Synthesis Methods with in situ hydrolysis
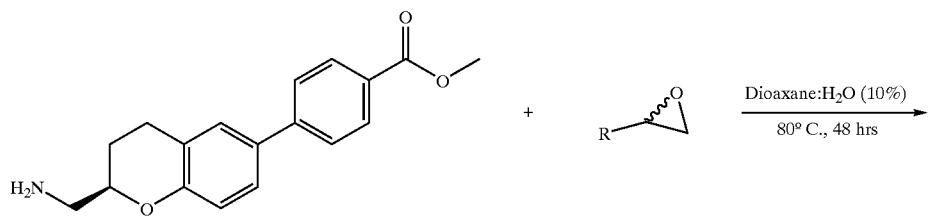

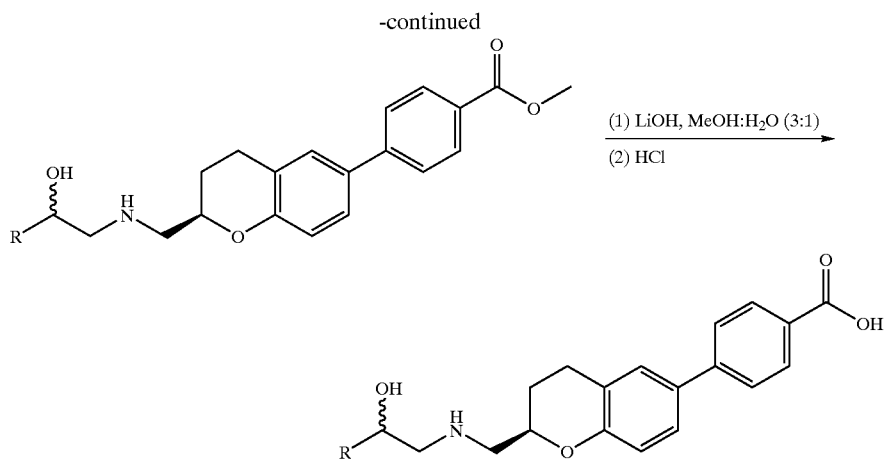

(1) LiOH, MeOH:H$_2$O (3:1)
(2) HCl

The following solutions were prepared prior to use.
1. 0.5 M 6-(4-methoxycarbonylphenyl)-(R)-chroman-2-methylamine solution in dioxane
2. 0.5 M epoxide solution in dioxane
3. 2 M Lithium hydroxide solution in methanol and water (3:1)

(a) Condensation of the Chroman Amine with Epoxides

In a 8-mL screw-cap vial, 200 μL of 6-(4-methoxycarbonylphenyl)-(R)-chroman-2-methylamine solution (0.01 mmol) and 200 μL of epoxide solution (0.01 mmol) were dispensed. Dioxane (500 μL) and water (100 μL) were then added to each well, and the mixture was heated at 80° C. with mixing by orbital shaking for 2 days. After the mixture was allowed to cool to room temperature, the solvent was removed under reduced pressure by using a multiple sample evaporator (GeneVac).

(b) Hydrolysis of the Methyl Ester

The residue obtained from the previous procedure (a) was heated in 1 mL of 2 M lithium hydroxide solution in methanol and water (3:1) at 60° C. overnight. After allowing the reaction mixture to cool to room temperature, 2 N hydrochloric acid (1.1 mL) was slowly added to each well. Precipitate was formed in the vial. The solvent was removed under reduced pressure (GeneVac). The residue was redissolved in 1 mL MeOH and purified by preparative reversed phase HPLC, using aqueous MeCN containing 0.1% trifluoroacetic acid as eluant.

Using the above procedure, Examples 276–286 were prepared and are summarized in Table 23.

TABLE 23

| Example No. | STRUCTURE | LC-MS RT (min) | MS [M + H]+ |
|---|---|---|---|
| 276 | Chiral | 2.37 | 668 |
| 277 | Chiral | 1.82 | 491 |

TABLE 23-continued
| Example No. | STRUCTURE | LC-MS RT (min) | MS [M + H]+ |
|---|---|---|---|
| 278 | 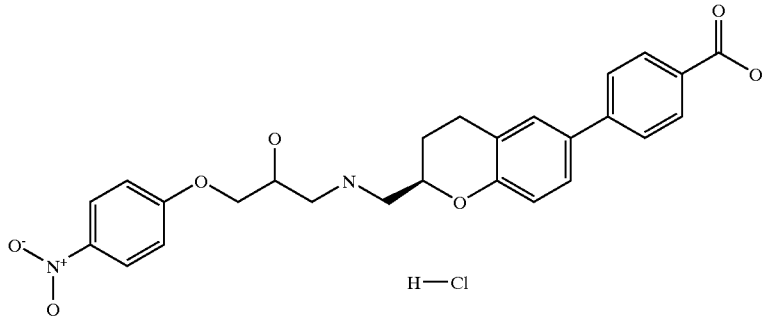 | 2.66 | 479 |
| 279 | 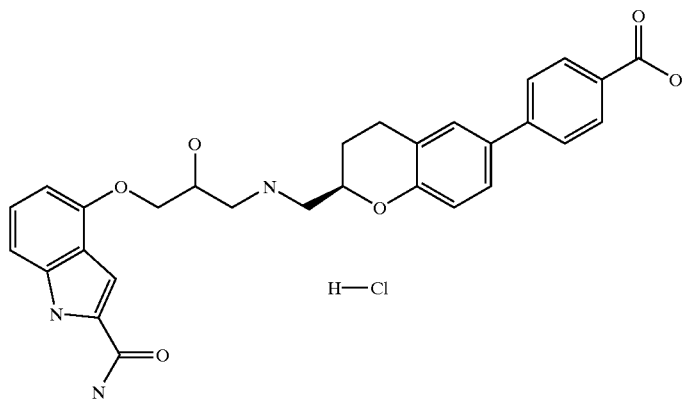 | 2.66 | 516 |
| 280 | 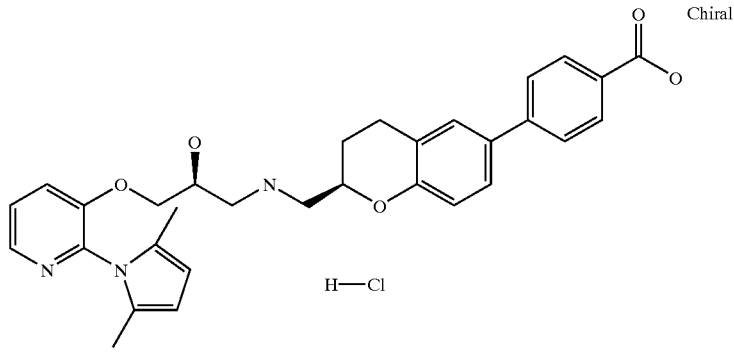 | 2.12 | 528 |
| 281 | 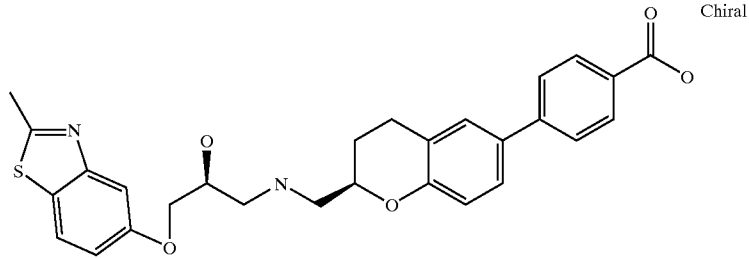 | 1.97 | 505 |

TABLE 23-continued

| Example No. | STRUCTURE | LC-MS RT (min) | MS [M + H]+ |
|---|---|---|---|
| 282 | (Chiral structure with morpholine-phenoxy-hydroxypropyl-amino-chromanyl-benzoate, H—Cl) | 2.00 | 519 |
| 283 | (Chiral structure with phthalimido-phenoxy-hydroxypropyl-amino-chromanyl-benzoate, H—Cl) | 2.15 | 579 |
| 284 | (Chiral structure with piperidinylmethyl-pyridinyloxy-hydroxypropyl-amino-chromanyl-benzoate, H—Cl) | 4.61 | 532 |
| 285 | (Chiral structure with dimethylamino-phenoxy-hydroxypropyl-amino-chromanyl-benzoate, H—Cl) | 4.13 | 477 |

TABLE 23-continued

| Example No. | STRUCTURE | LC-MS RT (min) | MS [M + H]+ |
|---|---|---|---|
| 286 | 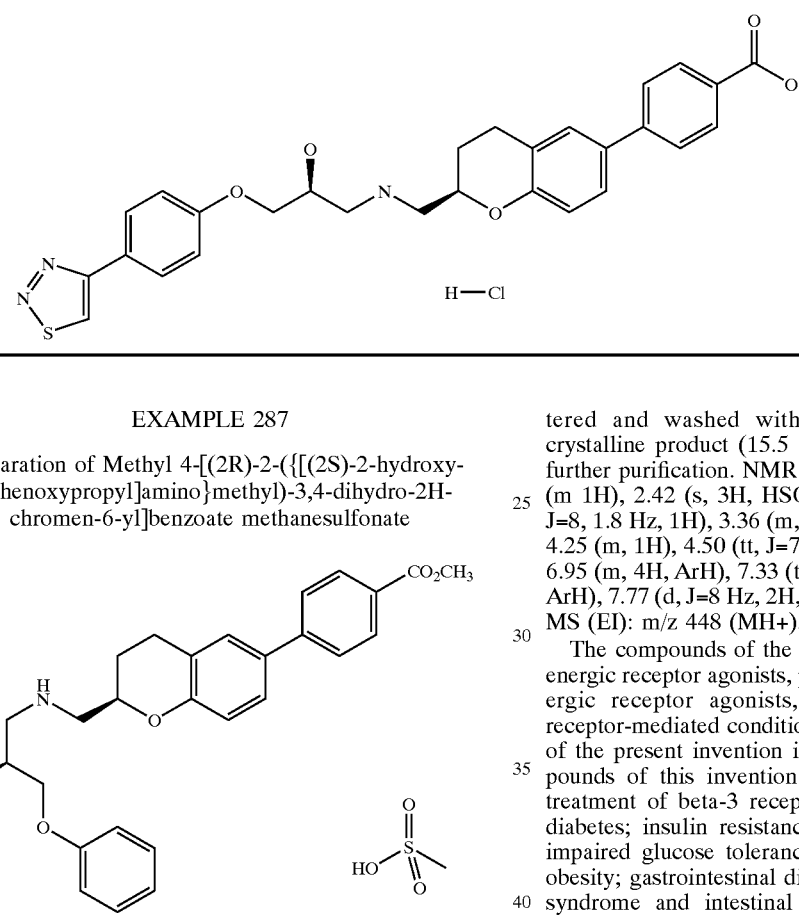 Chiral | 2.04 | 518 |

EXAMPLE 287

Preparation of Methyl 4-[(2R)-2-({[(2S)-2-hydroxy-3-phenoxypropyl]amino}methyl)-3,4-dihydro-2H-chromen-6-yl]benzoate methanesulfonate

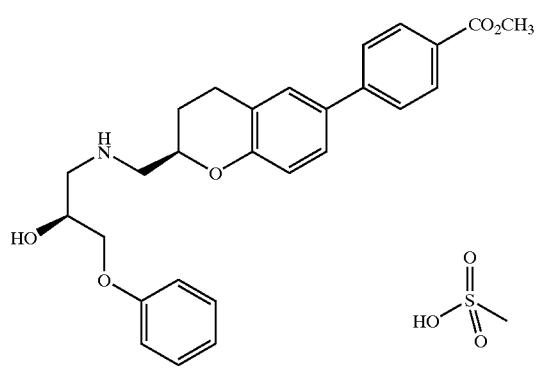

In a 500-mL three-neck round bottom flask was dissolved K$_2$CO$_3$ (37.3 g, 270 mmol, 3.8 eq.) in 120 mL water. (2S)-1-(benzyl{[(2R)-6-bromo-3,4-dihydro-2H-chromen-2-yl]methyl}amino)-3-phenoxy-2-propanol hydrobromide (Example 86, 40 g, 180 mmol, 1.0 eq.) was then added. To the resulting suspension was then added 130 mL isopropanol, p-carbomethoxyphenyl boronic acid (20.5 g, 114 mmol, 1.6 eq.) and 10% Pd/C (3.77 g, 1.78 mmol, 0.025 eq.). The resulting suspension was heated at reflux for 4 hours, cooled to 40° C., and 159 mL ethylacetate was added. This suspension was heated to 50° C. and filtered and washed with 100 mL warm (55° C.) ethylacetate. The filtrate separated to two phases. The aqueous phase was separated, and the organic phase was transferred to a 1-L three-neck round bottom flask, to which was added 300 mL ethyl acetate, 10% Pd-C (7.2 g, 0.89 mmol, 0.05 eq.) and a solution of sodium formate (14.4 g, 211 mmol, 3.0 eq.) in 80 mL water. The resulting suspension was refluxed for 6 hours. Methanesulfonic acid (28 g, 146 mmol, 4.1 eq.) was added to the reaction at a temperature ≧50° C. The resulting suspension was filtered; the organic filtrate was separated and washed with 60 mL water. The organics were distilled to half of the original volume, cooled and methyl 4-[(2R)-2-({[(2S)-2-hydroxy-3-phenoxypropyl]amino}methyl)-3,4-dihydro-2H-Chromen-6-yl]benzoate methanesulfonate filtered and washed with ethylacetate. The dry white crystalline product (15.5 g, 80% yield) was used without further purification. NMR (DMSO-d$_6$) δ1.77 (m, 1H), 2.10 (m 1H), 2.42 (s, 3H, HSO3CH$_3$), 2.90 (m, 2H), 3.12 (dd, J=8, 1.8 Hz, 1H), 3.36 (m, 2H), 3.85 (s, 3H), 4.02 (m, 2H), 4.25 (m, 1H), 4.50 (tt, J=7, 1.5 Hz, 1H), 5.87 (bs, 1H, OH), 6.95 (m, 4H, ArH), 7.33 (t, J=7 Hz, 2H, ArH), 7.52 (m, 2H, ArH), 7.77 (d, J=8 Hz, 2H, ArH), 7.95 (d, J=8 Hz, 2H, ArH); MS (EI): m/z 448 (MH+).

The compounds of the present invention are beta-3 adrenergic receptor agonists, preferably selective beta-3 adrenergic receptor agonists, that effect beta-3 adrenergic receptor-mediated conditions. Accordingly, an embodiment of the present invention is the administration of the compounds of this invention to a human or animal for the treatment of beta-3 receptor-mediated conditions such as diabetes; insulin resistance in pre-diabetic states such as impaired glucose tolerance and impaired fasting glucose; obesity; gastrointestinal disorders including irritable bowel syndrome and intestinal hypermotility disorders, peptic ulcerations, esophagitis, gastritis, and duodenitis; intestinal ulcerations including inflammatory bowel disease, ulcerative colitis, Crohn's disease and proctitis, and gastrointestinal ulcerations; as well as neurogenic inflammation such as cough and asthma, and depression. It is also believed that the compounds of this invention are effective in the treatment of hyper-triglyceridaemia, hypercholesterolaemia and conditions of low and high density lipoprotein levels, artherosclerotic disease and cardiovascular disease and related conditions. Additionally, it is also believed that the compounds of this invention are effective in the treatment of ocular hypertension and glaucoma, and in the treatment of urinary disorders including benign prostatic hyperplasia and incontinence, as well as in the treatment of prostate disease and as topical anti-inflammatory agents.

Therefore, the compounds of this invention are expected to be valuable as therapeutic agents. An embodiment of this invention includes a method of treating beta-3 adrenergic receptor-mediated conditions in a mammal which comprises administering to said mammal a composition containing an amount of the compound that is effective in treating the target condition.

An embodiment of this invention includes a method of treating beta-3 adrenergic receptor mediated conditions in a mammal which comprises administering to said mammal a composition containing an amount of the compound of Formula I that is effective in treating the target condition.

The specificity of the compounds of this invention as beta-3 adrenergic receptor agonists can readily be determined by evaluating the affinity of the compound for the beta-3 adrenergic receptor and comparing the activity with various receptor affinities to discover activity. This can be determined by standard and well-known procedures. For example, For example, the utility of the present invention as beta-3 adrenergic receptor agonists useful in treating beta-3 adrenergic receptor mediated conditions can be demonstrated by the following procedure.

EXAMPLE 289

Biological Evaluation of Compounds

The utility of the compounds can be demonstrated by the following procedure. Chinese hamster ovary (CHO) cells that stably express full-length human beta-3-adrenergic receptor (Emorine, L. J. et al: *Molecular Characterization of the Human Beta-3-Adrenergic Receptor.* Science (Wash. D.C.) 245: 1118–1121,1989) are used in the following procedure. The cell line is grown in 90% F12 nutrient mixture (HAM), 10% fetal bovine serum, 100 units/ml penicillin G sodium, 100 mg/ml streptomycin sulfate, and 2 mM L-glutamine at 37° C. in 95% air and 5% $CO_2$. The transfected cell line is maintained with G418 (800ug/ml).

To test agonist activity, cells are exposed to test compound and then assayed for cAMP production. CHO cells (100 μl) are plated at $5 \times 10^4$ cells/well of a 96-well plate (#3596, Costar, Cambridge, Mass.) to achieve 70% confluency the next day. After overnight incubation at 37° C., media is removed and the cells are treated for 30 minutes at 37° C. with KRP buffer (120 mM NaCl, 5.1 mM Kcl, 0.6 mM $MgSO_4.7H_2O$, 0.8 mM $CaCl_2.H_2O$, 12.5 μM Phosphate buffer, 20 μM Hepes pH 7.4)+0.2 μM IBMX (100 μl/well), +1% DMSO, +/−test compounds (10 μM DMSO stocks). Test compounds are assayed from 10 μM to 3 nM with 3-fold serial dilutions. The control agonist, isoproterenol (10 mM stock in 1.1 mM ascorbate), is assayed by 3-fold dilution beginning at 1 μM. Following a 30-minute incubation with the test compounds, the buffer/compound mixture is removed. The cells are lysed and cAMP levels are measured using the cAMP Scintillation Proximity assay (SPA) screening assay system (#RPA 559, Amersham, Arlington Heights, Ill.). The cAMP values are then plotted to ascertain the $EC_{50}$ of each compound tested.

In tests utilizing the above described procedure, the compounds of the present invention were found to have beta-3 adrenergic agonist activity with levels of activity summarized in Table 24.

TABLE 24

| Beta-3 Agonistic Activity | |
|---|---|
| Compounds with $EC_{50}$ values ≤1 μM (Example No.) | Compounds with $EC_{50}$ values >1 μM (Example No.) |
| 80 | 96 |
| 84 | 102 |
| 100 | 106 |
| 103 | 107 |
| 105 | 109 |
| 108 | 114 |
| 111 | 116 |
| 112 | 117 |
| 113 | 118 |
| 130 | 119 |

TABLE 24-continued

| Beta-3 Agonistic Activity | |
|---|---|
| Compounds with $EC_{50}$ values ≤1 μM (Example No.) | Compounds with $EC_{50}$ values >1 μM (Example No.) |
| 131 | 120 |
| 132 | 121 |
| 133 | 122 |
| 135 | 123 |
| 139 | 124 |
| 141 | 125 |
| 142 | 126 |
| 143 | 127 |
| 149 | 128 |
| 151 | 129 |
| 153 | 134 |
| 156 | 136 |
| 157 | 137 |
| 160 | 138 |
| 161 | 140 |
| 162 | 144 |
| 163 | 145 |
| 164 | 146 |
| 165 | 147 |
| 166 | 148 |
| 167 | 150 |
| 168 | 152 |
| 171 | 154 |
| 174 | 155 |
| 182 | 158 |
| 183 | 159 |
| 184 | 169 |
| 185 | 170 |
| 186 | 173 |
| 187 | 175 |
| 188 | 176 |
| 189 | 178 |
| 190 | 179 |
| 191 | 180 |
| 195 | 181 |
| 196 | 222 |
| 197 | 230 |
| 198 | 266 |
| 199 | 267 |
| 200 | 270 |
| 201 | |
| 202 | |
| 206 | |
| 207 | |
| 208 | |
| 209 | |
| 210 | |
| 211 | |
| 212 | |
| 213 | |
| 215 | |
| 216 | |
| 217 | |
| 220 | |
| 227 | |
| 232 | |
| 234 | |
| 239 | |
| 252 | |
| 253 | |
| 254 | |
| 263 | |
| 264 | |
| 265 | |
| 268 | |

Based upon the above and other standard laboratory techniques known to evaluate compound receptor site inhibition, by standard toxicity tests, and by standard pharmacological assays for the determination of treatment of the beta-3 receptor-mediated conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.01 mg/kg to about 100 mg/kg, and preferably from about 0.1 mg/kg to about 20 mg/kg body weight per day. A unit dosage may contain from about 5 mg to about 1500 mg of active ingredient, and can be administered one or more times per day. Of course, the specific initial and continuing dosage regimen for each patient will vary according to the nature and severity of the condition as determined by the attending diagnostician.

The compounds of this invention can be utilized to achieve the desired pharmacological effect by administration to a patient in need thereof in an appropriately formulated pharmaceutical composition. A patient, for the purpose of this invention, is a mammal, including a human, in need of treatment for a particular beta-3 adrenergic receptor-mediated condition or disease. Therefore, the present invention includes pharmaceutical compositions which are comprised of a pharmaceutically acceptable carrier and a pharmaceutically effective amount of a compound of Formula I, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds of Formula I may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly (ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylm ethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (See, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The compounds of this invention may be administered as the sole pharmaceutical agent or in combination with one or more other pharmaceutical agents where the combination causes no unacceptable adverse effects. For example, the compounds of this invention can be combined with known anti-obesity or other indication agents, and the like, as well as with admixtures and combinations thereof.

The compounds of Formula 1 may also be utilized, in free base form or in compositions, in research and diagnostics, or as analytical reference standards, and the like. Therefore, the present invention includes compositions which are comprised of an inert carrier and an effective amount of a compound of Formula I, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

The following examples are presented to illustrate the invention described herein, but should not be construed as limiting the scope of the invention in any way.

EXAMPLE 290

A capsule is prepared from

| | |
|---|---|
| A compound of Formula I | 40 mg |
| Starch | 109 mg |
| Magnesium steatrate | 1 mg |

The components are blended, passed through an appropriate mesh sieve, and filled into hard gelatin capsules.

EXAMPLE 291

A tablet is prepared from

| A compound of Formula I | 25 mg |
|---|---|
| Cellulose, microcrystaline | 200 mg |
| Colloidal silicon dioxide | 10 mg |
| Stearic acid | 5.0 mg |

The ingredients are mixed and compressed to form tablets.

What is claimed as new and useful is:

1. A compound of Formula I

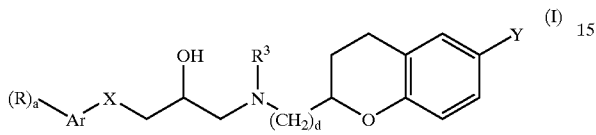

(I)

wherein

R is hydroxy, oxo, halo, cyano, nitro, $C_1$–$C_{10}$ alkyl optionally substituted with
phenyl, $C_1$–$C_{10}$ haloalkyl, $CF_3$, $NR^1R^1$, $SR^1$, $OR^1$, $SO_2R^2$, $OCOR^2$, $NR^1COR^2$, $COR^2$, $NR^1SO_2R^2$, phenyl, or a 5- or 6-membered heterocycle with 1 to 4 heteroatoms selected independently from O, S, and N,
each phenyl or heterocycle being optionally substituted with hydroxy, $R^1$, halo, cyano, $NR^1R^1$, $SR^1$, $CF_3$, $OR^1$, $C_3$–$C_8$ cycloalkyl, $NR^1COR^2$, $COR^2$, $SO_2R^2$, $OCOR^2$, $NR^1SO_2R^2$, $C_1$–$C_{10}$ alkyl, or $C_1$–$C_{10}$ alkoxy;

$R^1$ is hydrogen, $(CH_2)_d$—O—$(CH_2)_d R^5$, where each d is selected independently, or
$C_1$–$C_{10}$ alkyl optionally substituted with 1 to 4 substituents each independently selected from hydroxy, halo, $CO_2C_1$–$C_4$ alkyl, $CO_2H$, $S(O)_b C_1$–$C_{10}$ alkyl, $C_1$–$C_{10}$ alkoxy, and phenyl optionally substituted with $CO_2C_1$–$C_4$ alkyl or $CO_2H$, or $C_3$–$C_8$ cycloalkyl, phenyl, or naphthyl, each optionally substituted with 1 to 4 substituents each independently selected from halo, nitro, oxo, $C_1$–$C_{10}$ alkyl, $C_1$–$C_{10}$ alkoxy, and $C_1$–$C_{10}$ alkylthio; when two $R^1$ groups are attached to N as $NR^1R^1$, these $R^1$ groups may form together with the nitrogen to which they are attached, a heterocyclic ring containing 4 to 7 C atoms, 1 to 2 N atoms, and 0 to 1 O or S atoms;

$R^2$ is $R^1$; $OR^1$; $NR^1R^1$; $NHS(O)_b$phenyl optionally substituted with $C_1$–$C_4$ alkyl, $C_1$–$C_4$ alkoxy, halo, or nitro; $NHS(O)_b$naphthyl; NHS$(O)_b C_1$–$C_{10}$ alkyl; or a
5- or 6-membered heterocycle with one or more heteroatoms selected independently from O, S, and N, said heterocyclic moiety being optionally substituted with $R^1$;

$R^3$ is hydrogen, $C_1$–$C_{10}$ alkyl, benzyl, or $COR^2$;

$R^4$ is hydrogen, $C_1$–$C_{10}$ alkyl, $C_1$–$C_{10}$ alkyl-phenyl, or $C_1$–$C_{10}$ alkyl-pyridine;

$R^5$ is hydrogen or COOH;

Ar is phenyl optionally fused to a cyclohexyl, phenyl, or a 5- or 6-membered heterocycle containing one or more heteroatoms each independently selected from O, S, and N, each bicyclic moiety being optionally fused to phenyl, or a 5- or 6-membered heterocycle containing one or more heteroatoms each independently selected from N, S, and O, optionally fused to phenyl;

X is O or $S(O)_b$;

Y is halo, $R^1$, $OR^1$ $SR^1$, $CO_2R^1$, $NR^1R^1$, $S(O)_b$-phenyl-$CO_2R^1$, or
phenyl optionally fused to another phenyl ring or to a 5- or 6-membered heterocycle containing one or more heteroatoms each independently selected from N, S, and O, or a 5- or 6-membered heterocycle containing one or more heteroatoms each independently selected from N, S, and O, optionally fused to a phenyl ring, each phenyl or heterocycle being optionally substituted with one or more substituents independently selected from $COR^2$; halo; $OR^1$; $NR^1R^1$; $R^1$; $C_1$–$C_{10}COR^2$; phenyl optionally substituted with halo,
$C_1$–$C_4$ alkyl, or $C_1C_4$ alkoxy; tetrazolo; or

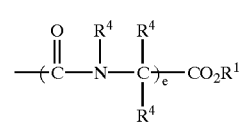

where, when the two $R^4$ groups attached to the same C are both alkyl, they optionally may be joined so that, when taken together with the C to which they are attached, they form a spiro ring of 3, 5, or 6 C atoms, or where the $R^4$ attached to N and one $R^4$ attached to the adjacent C are both alkyl, they optionally may be joined so that, taken together with the atoms to which they are attached, they form a 5- or 6-membered heterocycle;

a is 0, 1,2,3,4, or 5;

b is 0, 1, or 2;

d is 1,2, or 3;

e is 1 or 2;

and pharmaceutically acceptable salts and esters thereof.

2. The compound of claim 1 wherein d is 1.

3. The compound of claim 1 wherein $R^3$ is H.

4. The compound of claim 1 wherein X is O or S.

5. The compound of claim 1 wherein Ar is phenyl, naphthyl, pyridyl, carbazolyl, indolinyl, dibenzylfuryl, benzothiazolyl, or a 5- or 6-membered heterocycle containing one or more heteroatoms each independently selected form O, S, and N optionally fused to phenyl.

6. The compound of claim 1 wherein Y is halo, phenyl optionally fused to another phenyl ring or to a 5- or 6-membered heterocycle containing one or more heteroatoms each independently selected from N, S, and O; or
a 5- or 6-membered heterocycle containing one or more heteroatoms each independently selected from N, S and O, optionally fused to a phenyl ring, each phenyl or heterocycle being optionally substituted with one or more substituents independently selected from $COR^2$; halo; $OR^1$; $R^1$; $C_1$–$C_{10}COR^2$; tetrazolo; phenyl optionally substituted with halo, $C_1$–$C_4$ alkyl, or $C_1C_4$ alkoxy.

7. The compound of claim 1 wherein

R is hydroxy, halo, cyano, $C_1$–$C_{10}$ alkyl optionally substituted with phenyl,
$C_1$–$C_{10}$haloalkyl, $CF_3$, $NR^1R^1$, $SR^1$, $OR^1$, $SO_2R^2$, $OCOR^2$, $NR^1COR^2$, $COR^2$, $NR^1SO_2R^2$, phenyl, or a 5- or 6-membered heterocycle with from 1 to 2 heteroatoms selected independently from O, S, and N, each phenyl or heterocycle being optionally substituted with hydroxy, $R^1$, halo, cyano, $NR^1R^1$, $SR^1$, CF$_3$, OR$^1$, C$_3$–C$_8$ cycloalkyl, NR$^1$COR$^2$, COR$^2$, SO$_2$R$^2$, OCOR$^2$, NR$^1$SO$_2$R$^2$, C$_1$–C$_{10}$ alkyl, or C$_1$–C$_{10}$ alkoxy;

R$^1$ is hydrogen, C$_1$–C$_{10}$ alkyl optionally substituted with 1 to 4 substituents each independently selected from hydroxy, halo, phenyl optionally substituted with CO$_2$C$_1$–C$_4$ alkyl or CO$_2$H, S(O)$_b$C$_1$–C$_{10}$ alkyl, and C$_1$–C$_{10}$ alkoxy, or C$_3$–C$_8$ cycloalkyl, phenyl or naphthyl, each optionally substituted with 1 to 4 substituents each independently selected from halo, nitro, oxo, C$_1$–C$_{10}$ alkyl, C$_1$–C$_{10}$ alkoxy, and C$_1$–C$_{10}$ alkylthio;

R$^2$ is R$^1$; OR$^1$; NR$^1$R$^1$; NHS(O)$_b$phenyl optionally substituted with halo, C$_1$–C$_4$ alkyl,
C$_1$–C$_4$ alkoxy, halo or nitro; NHS(O)$_b$naphthyl; NHS(O)$_b$C$_1$–C$_{10}$ alkyl; or a 5- or 6-membered heterocycle with one or two heteroatoms selected independently from O, S, and N, said heterocyclic moiety being optionally substituted with R$^1$;

R$^3$ is hydrogen, or benzyl;

R$^4$ is hydrogen, C$_1$–C$_{10}$ alkyl, C$_1$–C$_{10}$ alkyl-phenyl, C$_1$–C$_{10}$ alkyl-pyridine;

R$^5$ is hydrogen or COOH;

Ar is phenyl optionally fused to a cyclohexyl, phenyl or a 5- or 6-membered heterocycle containing one or more heteroatoms each independently selected from O, S and N, each bicyclic moiety being optionally fused to phenyl, or a 5- or 6-membered heterocycle containing one or more heteroatoms each independently selected from N, S, and O, optionally fused to phenyl;

X is O or S;

Y is halo, R$^1$, OR$^1$ SR$^1$, CO$_2$R$^1$, NR$^1$R$^1$, S(O)$_b$-phenyl-CO$_2$R$^1$ or phenyl optionally
fused to another phenyl ring or to a 5- or 6-membered heterocycle containing one or more heteroatoms each independently selected from N, S, and O, or a 5- or 6-membered heterocycle containing one or more heteroatoms each independently selected from N, S, and O, optionally fused to a phenyl ring, each phenyl or heterocycle being optionally substituted with one or more substituents independently selected from COR$^2$; halo; OR$^1$; R$^1$; C$_1$–C$_{10}$COR$^2$; phenyl optionally substituted with halo, C$_1$–C$_4$ alkyl, or C$_1$C$_4$ alkoxy; tetrazolo; or

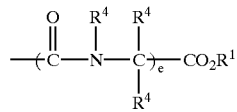

where, when the two R$^4$ groups attached to the same C are both alkyl, they optionally may be joined so that, when taken together with the C to which they are attached, they form a spiro ring of 3, 5, or 6 C atoms, or where the R$^4$ attached to N and one R$^4$ attached to the adjacent C are both alkyl, they optionally may be joined so that, taken together with the atoms to which they are attached, they form a 5- or 6-membered heterocycle;

a is 0, 1, or 2;

b is 0, 1 or 2 d is 1 and e is 1;

and the pharmaceutically acceptable salts and esters thereof.

8. The compound of claim 1 wherein,

R is hydroxy, halo, cyano, C$_1$–C$_4$ alkyl, C$_1$–C$_4$ haloalkyl, CF$_3$, NR$^1$R$^1$, SR$^1$, OR$^1$, SO$_2$R$^2$, OCOR$^2$, NR$^1$COR$^2$, COR$^2$, NR$^1$SO$_2$R$^2$, phenyl, or a 5- or 6-membered heterocycle with from 1 to 2 heteroatoms selected independently from O, S, and N, each phenyl or heterocycle being optionally substituted with hydroxy, R$^1$, halo, cyano,
NR$^1$R$^1$, SR$^1$, CF$_3$, OR$^1$, C$_3$–C$_8$ cycloalkyl, NR$^1$COR$^2$, COR$^2$, SO$_2$R$^2$, OCOR$^2$,
NR$^1$SO$_2$R$^2$, C$_1$–C$_{10}$ alkyl, or C$_1$–C$_4$ alkoxy;

R$^1$ is hydrogen, C$_1$–C$_4$ alkyl optionally substituted with 1 to 4 substituents each independently selected from hydroxy, halo, phenyl optionally substituted with CO$_2$C$_1$–C$_4$ alkyl or CO$_2$H, CO$_2$C$_1$–C$_4$ alkyl, CO$_2$H, S(O)$_b$C$_1$–C$_4$ alkyl, and C$_1$–C$_4$ alkoxy, or C$_3$–C$_6$ cycloalkyl, phenyl or naphthyl, each optionally substituted with 1 to 2 substituents each independently selected from halo, nitro, C$_1$–C$_4$ alkyl, C$_1$–C$_4$ alkoxy, and C$_1$–C$_4$ alkylthio;

R$^2$ is R$^1$; OR$^1$; NR$^1$R$^1$; NHS(O)$_b$phenyl optionally substituted with halo, C$_1$–C$_4$ alkyl,
C$_1$–C$_4$ alkoxy, halo or nitro; NHS(O)$_b$naphthyl; NHS(O)$_b$C$_1$–C$_{10}$ alkyl; or a 5- or
6-membered heterocycle with one or two heteroatoms selected independently from O, S, and N, said heterocyclic moiety being optionally substituted with R$^1$;

R$^3$ is hydrogen, or benzyl;

R$^4$ is hydrogen, C$_1$–C$_{10}$ alkyl, C$_1$–C$_{10}$ alkyl-phenyl, or C$_1$–C$_{10}$ alkyl-pyridine;

R$^5$ is hydrogen or COOH;

Ar is phenyl optionally fused to a cyclohexyl, phenyl or a 5- or 6-membered
heterocycle containing one or more heteroatoms each independently selected from O, S, and N, each bicyclic moiety being optionally fused to phenyl, or a 5- or 6-membered heterocycle containing one or more heteroatoms each independently selected from N, S, and O, optionally fused to phenyl;

X is O or S;

Y is halo, R$^1$, OR$^1$ SR$^1$, CO$_2$R$^1$, NR$^1$R$^1$, S(O)$_b$-phenyl-CO$_2$R$^1$ or phenyl optionally
fused to another phenyl ring or to a 5- or 6-membered heterocycle containing one or more heteroatoms each independently selected from N, S and O, or a 5- or 6-membered heterocycle containing one or more heteroatoms each independently selected from N, S, and O, optionally fused to a phenyl ring,
each phenyl or heterocycle being optionally substituted with one or more substituents independently selected from COR$^2$, halo, OR$^1$, R$^1$, C$_1$–C$_{10}$COR$^2$, tetrazolo, phenyl optionally substituted with halo, C$_1$–C$_4$ alkyl, or C$_1$C$_4$ alkoxy;

a is 0, 1, or 2 b is 0, 1 or 2 d is 1 and e is 1;

and the pharmaceutically acceptable salts and esters thereof.

9. The compound of claim 1 wherein,

R is halo, C$_1$–C$_4$ alkyl, C$_1$–C$_4$ haloalkyl, CF$_3$;

R$^1$ is hydrogen, C$_1$–C$_4$ alkyl optionally substituted with 1 to 4 substituents each independently selected from hydroxy, halo, phenyl, or $C_3$–$C_6$ cycloalkyl, phenyl or naphthyl, each optionally substituted with 1 to 2 substituents each independently selected from halo, $C_1$–$C_4$ alkyl, $C_1$–$C_4$ alkoxy, and $C_1$–$C_4$ alkylthio;

$R^2$ is $R^1$; $OR^1$; $NR^1R^1$; $NHS(O)_b$phenyl optionally substituted with halo, $C_1$–$C_4$ alkyl,
$C_1$–$C_4$ alkoxy; $NHS(O)_b$naphthyl; $NHS(O)_bC_1$–$C_{10}$ alkyl; or a 5- or 6-membered heterocycle with one or two heteroatoms selected independently from O, S, and N, said heterocyclic moiety being optionally substituted with $R^1$;

$R^3$ is hydrogen, $R^4$ is hydrogen, $C_1$–$C_{10}$ alkyl, $C_1$–$C_{10}$ alkyl-phenyl, or $C_1$–$C_{10}$ alkyl-pyridine;

$R^5$ is hydrogen or COOH;

Ar is phenyl optionally fused to a cyclohexyl, phenyl or a 5- or 6-membered
heterocycle containing one or more heteroatoms each independently selected from O, S, and N, each bicyclic moiety being optionally fused to phenyl, or a 5- or 6-membered heterocycle containing one or more heteroatoms each independently selected from N, S, and O, optionally fused to phenyl;

X is O;

Y is halo, $R^1$, $S(O)_b$-phenyl-$CO_2R^1$ or phenyl optionally fused to another phenyl ring or to a 5- or 6-membered heterocycle containing one or more heteroatoms each independently selected from N, S, and O, or a 5- or 6-membered heterocycle containing one or more heteroatoms each independently selected from N, S, and O, optionally fused to a phenyl ring, each phenyl or heterocycle being optionally substituted with one or more substituents independently selected from $COR^2$, halo, $OR^1$, $R^1$, $C_1$–$C_4COR^2$, tetrazolo, phenyl optionally substituted with halo, $C_1$–$C_4$ alkyl, or $C_1C_4$ alkoxy;

a is 0, 1, or 2 b is 0, 1 or 2 d is 1 and e is 1;

and the pharmaceutically acceptable salts and esters thereof.

10. The compound of claim 1 selected from the group consisting of
(2S)-1-({[(2R)-6-iodo-3,4-dihydro-2H-chromen-2-yl] methyl}amino)-3-phenoxy-2-propanol;

(2S)-1-(Benzyl {[(2R)-6-bromo-3,4-dihydro-2H-chromen-2-yl]methyl}amino)-3-phenoxy-2-propanol;

(2S)-1-(Benzyl {[(2R)-6-bromo-3,4-dihydro-2H-chromen-2-yl]methyl}amino)-3-phenoxy-2-propanol hyrdrobromide;

Methyl 4-[(2R)-2-({benzyl[2S)-2-hydroxy-3-phenoxypropyl]amino}methyl)-3,4-dihydro-2H-chromen-6-yl]benzoate;

Methyl 4-[(2R)-2-({[(2S)-2-hydroxy-3-phenoxypropyl] amino}methyl)-3,4-dihydro2H-chromen-6-yl]benzoate;

Methyl 4-[(2R)-2-({[(2S)-2-hydroxy-3-phenoxypropyl] amino}methyl)-3,4-dihydro-2H-chromen-6-yl] benzoate methanesulfonate N-{3-[(2R)-2-({[(2S)-2-hydroxy-3-phenoxypropyl] amino}methyl)-3,4-dihydro-2H-chromen-6-yl] benzoyl}benzenesulfonamide;

Methyl 6-[(2R)-2-({[(2S)-2-hydroxy-3-phenoxypropyl] amino}methyl)-3,4-dihydro-2H-chromen-6-yl]-2-naphthoate;

Methyl 6-{(2R)-2-[({(2S)-2-hydroxy-3-[2-(trifluoromethyl)phenoxy]propyl}amino)methyl]-3,4-dihydro-2H-chromen-6-yl}-2-naphthoate;

Methyl 6-[(2R)-2-({[(2S)-2-hydroxy-3-(3-pyridinyloxy) propyl]amino}methyl)-3,4-dihydro-2H-chromen-6-yl]-2-naphthoate;

Methyl 6-[(2R)-2-({[(2S)-2-hydroxy-3-(4-hydroxyphenoxy)propyl]amino}methyl)-3,4dihydro-2H-chromen-6-yl]-2-naphthoate;

Methyl 6-[(2R)-2-({[(2S)-2-hydroxy-3-(2-hydroxyphenoxy)propyl]amino}methyl)-3,4-dihydro-2H-chromen-6-yl]-2-naphthoate;

Ethyl 7-[(2R)-2-({[(2S)-2-hydroxy-3-phenoxypropyl] amino}methyl)-3,4-dihydro-2H-chromen-6-yl]-2-naphthoate;

Methyl 5-[(2R)-2-({[(2S)-2-hydroxy-3-phenoxypropyl] amino}methyl)-3,4-dihydro-2H-chromen-6-yl]-2,3-dihydro-1-benzofuran-7-carboxylate;

Ethyl 4-[(2S)-2-({[(2S)-2-hydroxy-3-phenoxypropyl] amino}methyl)-3,4-dihydro-2H-chromen-6-yl]-1,5-dimethyl-1H-pyrazole-3-carboxylate;

Methyl 5-[(2S)-2-({[(2S)-2-hydroxy-3-phenoxypropyl] amino}methyl)-3,4-dihydro-2H-chromen-6-yl]-3-thiophenecarboxylate;

Methyl 4-[(2S)-2-({[(2S)-2-hydroxy-3-phenoxypropyl] amino}methyl)-3 ,4-dihydro-2H-chromen-6-yl]-2-thiophenecarboxylate;

Methyl 2-[(2S)-2-({[(2S)-2-hydroxy-3-phenoxypropyl] amino}methyl)-3,4-dihydro-2H-chromen-6-yl]-5-phenyl-1,3-thiazole-4-carboxylate;

4-{(2R)-2-[({(2S)-2-hydroxy-3-[4-(2-methoxyethyl) phenoxy]propyl}amino)methyl]-3,4-dihydro-2H-chromen-6-yl}benzoic acid;

4-[(2R)-2-({[(2S)-3-(9H-carbazol-4-yloxy)-2-hydroxypropyl]amino}methyl)-3,4-dihydro-2H-chromen-6-yl]benzoic acid;

4-[(2R)-2-({[(2S)-2-Hydroxy-3-phenoxypropyl] amino}methyl)-3,4-dihydro-2H-chromen-6-yl]benzoic acid;

4-[(2R)-2-({[(2S)-3-(2-ethylphenoxy)-2-hydroxypropyl] amino}methyl)-3,4-dihydro-2H-chromen-6-yl]benzoic acid;

4-[(2R)-2-({[(2S)-2-hydroxy-3-(3-isopropylphenoxy) propyl]amino}methyl)-3,4dihydro-2H-chromen-6-yl] benzoic acid;

4-[(2R)-2-({[(2S)-3-(2-ethoxyphenoxy)-2-hydroxypropyl]amino}methyl)-3,4-dihydro-2H-chromen-6-yl]benzoic acid;

4-[(2R)-2-({[(2S)-2-hydroxy-3-(2-isopropoxyphenoxy) propyl]amino}methyl)-3,4-dihydro-2H-chromen-6-yl] benzoic acid;

4-[(2R)-2-({[(2S)-3-(2-chlorophenoxy)-2-hydroxypropyl]amino}methyl)-3,4-dihydro-2H-chromen-6-yl]benzoic acid;

4-{(2R)-2-[({(2S)-2-hydroxy-3-[2-(trifluoromethyl) phenoxy]propyl}amino)methyl]-3,4-dihydro-2H-chromen-6-yl}benzoic acid;

4-[(2R)-2-({[(2S)-2-hydroxy-3-(3-pyridinyloxy)propyl] amino}methyl)3,4dihydro-2H-chromen-6-yl]benzoic acid;

4-[(2R)-2-({[(2S)-3-(4-fluorophenoxy)-2-hydroxypropyl]amino}methyl)-3,4-dihydro-2H-chromen-6-yl]benzoic acid;

4-[(2R)-2-({[(2S)-3-(2-fluorophenoxy)-2-hydroxypropyl]amino}methyl)-3,4-dihydro-2H-chromen-6-yl-]benzoic acid;

4-[(2R)-2-({[(2S)-2[hydroxy-3-(4-hydroxyphenoxy)propyl]amino}methyl)-3,4-dihydro-2H-chromen-6-yl]benzoic acid;

4-[(2R)-2-({[(2S)-2-hydroxy-3-(2-hydroxyphenoxy)propyl]amino}methyl)-3,4-dihydro-2H-chromen-6-yl]benzoic acid;

3-[(2R)-2-({[(2S)-2-hydroxy-3-phenoxypropyl]amino}methyl)-3,4-dihydro-2H-chromen-6-yl]benzoic acid;

3-[(2R)-2-({[(2S)-3-(4-fluorophenoxy)-2-hydroxypropyl]amino}methyl)-3,4-dihydro-2H-chromen-6-yl]benzoic acid;

3-[(2R)-2-({[(2S)-3-(2-fluorophenoxy)-2-hydroxypropyl]amino}methyl)-3,4-dihydro-2H-chromen-6-yl]benzoic acid;

4-[(2R)-2-({[(2S)-2-hydroxy-3-(phenylsulfanyl)propyl]amino}methyl)-3,4-dihydro-2H-chromen-6-yl]benzoic acid;

4-[(2R)-2-({[(2S)-2-hydroxy-3-(2-isopropylphenylsulfanyl)propyl]amino}methyl)-3,4-dihydro-2H-chromen-6-yl]benzoic acid;

4-[(2R)-2-({[(2S)-2-hydroxy-3-(2-fluorophenylsulfanyl)propyl]amino}methyl)-3,4-dihydro-2H-chromen-6-yl]benzoic acid;

6-[(2R)-2-({[(2S)-2-hydroxy-3-phenoxypropyl]amino}methyl)-3,4-dihydro-2H-chromen-6-yl]-2-naphthoic acid;

4-[(2R)-2-({[(2S)-2-hydroxy-3-phenoxypropyl]amino}methyl)-3,4-dihydro-2H-chromen-6-yl]-2-thiophenecarboxylic acid;

4-[(2R)-2-({[(2S)-2-hydroxy-3-phenoxypropyl]amino}methyl)-3,4-dihydro-2H-chromen-6-yl]-1,5-dimethyl-1H-pyrazole-3-carboxylic acid;

5-[(2R)-2-({[(2S)-2-hydroxy-3-phenoxypropyl]amino}methyl)-3,4-dihydro-2H-chromen-6-yl]-2,3-dihydro-1-benzofuran-7-carboxylic acid;

5-[(2R)-2-({[(2S)-2-hydroxy-3-phenoxypropyl]amino}methyl)-3,4-dihydro-2H-chromen-6-yl]-3-thiophenecarboxylic acid;

2-[(2R)-2-({[(2S)-2-hydroxy-3-phenoxypropyl]amino}methyl)-3,4-dihydro-2H-chromen-6-yl]-5-phenyl-1,3-oxazole-4-carboxylic acid;

2-[(2R)-2-({[(2S)-2-hydroxy-3-phenoxypropyl]amino}methyl)-3,4-dihydro-2H-chromen-6-yl]-5-phenyl-1,3-thiazole-4-carboxylic acid;

2-[(2R)-2-({[(2S)-2-hydroxy-3-phenoxypropyl]amino}methyl)-3,4-dihydro-2H-chromen-6-yl]-4-phenyl-1,3-thiazole-5-carboxylic acid;

2-[(2R)-2-({[(2S)-2-hydroxy-3-phenoxypropyl]amino}methyl)-3,4-dihydro-2H-chromen-6-yl]-4-isopropyl-1,3-thiazole-5-carboxylic acid;

2-[(2R)-2-({[(2S)-2-hydroxy-3-phenoxypropyl]amino}methyl)-3,4-dihydro-2H-chromen-6-yl]-5-isopropyl-1,3-thiazole-4-carboxylic acid;

2-(butylamino)-4-[(2R)-2-({[(2)-2-hydroxy-3-(phenyloxy)propyl]amino}methyl)-3,4-dihydro-2H-chromen-6-yl]benzoic acid;

4-[(2R)-2-({[(2S)-2-hydroxy-3-phenoxypropyl]amino}methyl)-3,4-dihydro-2H-chromen-6-yl]-2-[(2-methoxyethyl)amino]benzoic acid;

2-(cyclohexylamino)-4-[(2R)-2-({[(2S)-2-hydroxy-3-phenoxypropyl]amino}methyl)-3,4-dihydro-2H-chromen-6-yl]benzoic acid;

2-amino-4-[(2R)-2-({[(2S)-2-hydroxy-3-phenoxypropyl]amino}methyl)-3,4-dihydro-2H-chromen-6-yl]benzoic acid;

2-(diethylamino)-4-[(2R)-2-({[(2S)-2-hydroxy-3-phenoxypropyl]amino}methyl)-3,4-dihydro-2H-chromen-6-yl]benzoic acid 4-[(2R)-2-({[(2S)-2-hydroxy-3-phenoxypropyl]amino}methyl)-3,4-dihydro-2H-chromen-6-yl]-2-(isobutylamino)benzoic acid;

2-(cyclobutylamino)-4-[(2R)-2-({[(2S)-2-hydroxy-3-phenoxypropyl]amino}methyl)-3,4-dihydro-2H-chromen-6-yl]benzoic acid;

4-[(2R)-2-({[(2S)-2-hydroxy-3-phenoxypropyl]amino}methyl)-3,4-dihydro-2H-chromen-6-yl]-2-(1-piperidinyl)benzoic acid;

4-[(2S)-2-({[(2S)-2-hydroxy-3-phenoxypropyl]amino}methyl)-3,4-dihydro-2H-chromen-6-yl]-2-methoxybenzoic acid;

2-ethoxy-4-[(2R)-2-({[(2S)-2-hydroxy-3-phenoxypropyl]amino}methyl)-3,4dihydro-2H-chromen-6-yl]benzoic acid;

2-propoxy-4-[(2R)-2-({[(2S)-2-hydroxy-3-phenoxypropyl]amino}methyl)-3,4-dihydro-2H-chromen-6-yl]benzoic acid;

4-[(2R)-2-({[(2S)-2-hydroxy-3-phenoxypropyl]amino}methyl)-3,4-dihydro-2H-chromen-6-yl]-2-isobutoxybenzoic acid;

4-[(2R)-2-({[(2S)-2-hydroxy-3-phenoxypropyl]amino}methyl)-3,4-dihydro-2H-chromen-6-yl]-2-(2-methoxyethoxy)benzoic acid;

4-[(2R)-2-({[(2S)-2-hydroxy-3-phenoxypropyl]amino}methyl)-3,4-dihydro-2H-chromen-6-yl]-2-isopropoxybenzoic acid;

2-butoxy-4-[(2R)-2-({[(2S)-2-hydroxy-3-phenoxypropyl]amino}methyl)-3,4-dihydro-2-H-chromen-6-yl]benzoic acid;

2-hydroxy-4-[(2S)-2-({[(2S)-2-hydroxy-3-phenoxypropyl]amino}methyl)-3,4-dihydro-2H-chromen-6-yl]benzoic acid;

5-[(2S)-2-({[(2S)-2-hydroxy-3-phenoxypropyl]amino}methyl)-3,4-dihydro-2H-chromen-6-yl]-1,1'-biphenyl-2-carboxylic acid;

4'-chloro-5-[(2R)-2-({[(2S)-2-hydroxy-3-phenoxypropyl]amino}methyl)-3,4-dihydro-2H-chromen-6-yl]-1,1'-biphenyl-2-carboxylic acid;

4'-methyl-5-[(2R)-2-({[(2S)-2-hydroxy-3-phenoxypropyl]amino}methyl)-3,4-dihydro-2H-chromen-6-yl]-1,1'-biphenyl-2-carboxylic acid;

4'-tert-butyl-5-[(2R)-2-({[(2S)-2-hydroxy-3-phenoxypropyl]amino}methyl)-3,4-dihydro-2H-chromen-6-yl]-1,1'-biphenyl-2-carboxylic acid;

4-[(2R)-2-({[2-hydroxy-3-(2-methylphenoxy)propyl]amino}methyl)-3,4-dihydro-2H-chromen-6-yl]benzoic acid trifluoroacetate;

4-[(2R)-2-({[3-(4-fluorophenoxy)-2-hydroxypropyl]amino}methyl)-3,4-dihydro-2H-chromen-6-yl]benzoic acid trifluoroacetate;

4-[(2R)-2-({[3-(2-chlorophenoxy)-2-hydroxypropyl]amino}methyl)-3,4-dihydro2H-chromen-6-yl]benzoic acid trifluoroacetate;

4-[(2R)-2-({[3-(1,1'-biphenyl-2-yloxy)-2-hydroxypropyl]amino}methyl)-3,4-dihydro-2H-chromen-6-yl]benzoic acid trifluoroacetate;

4-[(2R)-2-({[(2S)-3-(2-chlorophenoxy)-2-hydroxypropyl]amino}methyl)-3,4-dihydro-2H-chromen-6-yl]benzoic acid trifluoroacetate;

4-[(2R)-2-({[(2S)-3-(2-fluorophenoxy)-2-hydroxypropyl]amino}methyl)-3,4-dihydro-2H-chromen-6-yl]benzoic acid trifluoroacetate;

4-[(2R)-2-({[(2S)-3-(3-chlorophenoxy)-2-hydroxypropyl]amino}methyl)-3,4-dihydro-2H-chromen-6-yl]benzoic acid trifluoroacetate;

3-[(2R)-2-({[(2S)-2-hydroxy-3-phenoxypropyl]amino}methyl)-3,4-dihydro-2H-chromen-6-yl]propanoic acid;

3-[(2R)-2-({[(2S)-3-(2-chlorophenoxy)-2-hydroxypropyl]amino}methyl)-3,4-dihydro-2H-chromen-6-yl]propanoic acid;

3-[(2R)-2-({[(2S)-3-(2-fluorophenoxy)-2-hydroxypropyl]amino}methyl)-3,4-dihydro-2H-chromen-6-yl]propanoic acid; and 3-[(2R)-2-({[(2S)-3-(4-fluorophenoxy)-2-hydroxypropyl]amino}methyl)3,4dihydro-2H-chromen-6-yl]propanoic acid trifluoroacetate.

11. A compound which is N-Benzyl-N-{[(2R)-6-bromo-3,4-dihydro-2H-chromen-2-yl]methyl}amine.

12. A method of preparing the compound of claim 1, comprising the step of using a compound of Formula 2 as an intermediate,

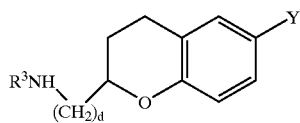

wherein
R$^1$ is hydrogen, $(CH_2)_d$—O—$(C_2)_d R^5$, where each d is selected independently, or
$C_1$–$C_{10}$ alkyl optionally substituted with 1 to 4 substituents each independently selected from hydroxy, halo, $CO_2C_1$–$C_4$ alkyl, $CO_2H$, $S(O)_b C_1$–$C_{10}$ alkyl, $C_1$–$C_{10}$ alkoxy, and phenyl optionally substituted with $CO_2C_1$–$C_4$ alkyl or $CO_2H$, or
$C_3$–$C_8$ cycloalkyl, phenyl or naphthyl, each optionally substituted with 1 to 4 substituents each independently selected from halo, intro, oxo, $C_1$–$C_{10}$ alkyl, $C_1$–$C_{10}$ alkoxy, and $C_1$–$C_{10}$ alkylthio;

R$^2$ is R$^1$; OR$^1$; NR$^1$R$^1$; NHS(O)$_b$phenyl optionally substituted with halo, $C_1$–$C_4$ alkyl,
$C_1$–$C_4$ alkoxy, or nitro; NHS(O)$_b$naphthyl; NHS(O)$_b C_1$–$C_{10}$ alkyl; or a 5- or 6-membered heterocycle with one or more heteroatoms selected independently from O, S, and N, said heterocyclic moiety being optionally substituted with R$^1$;

R$^3$ is hydrogen, $C_1$–$C_{10}$ alkyl, benzyl, or COR$^2$;

R$^4$ is hydrogen, $C_1$–$C_{10}$ alkyl, $C_1$–$C_{10}$ alkyl-phenyl, $C_1$–$C_{10}$ alkyl-pyridine;

R$^5$ is hydrogen or COOH;

Y is halo, R$^1$, OR$^1$ SR$^1$, $CO_2R^1$, NR$^1$R$^1$, $S(O)_b$-phenyl-$CO_2R^1$ or phenyl optionally fused to another phenyl ring or to a 5- or 6-membered heterocycle containing one or more heteroatoms each independently selected from N, S, and O, or a 5- or 6-membered heterocycle containing one or more heteroatoms each independently selected from N, S, and O, optionally fused to a phenyl ring, each phenyl or heterocycle being optionally substituted with one or more substituents independently selected from COR$^2$; halo; OR$^1$; R$^1$; $C_1$–$C_{10}$COR$^2$; phenyl optionally substituted with halo, $C_1$–$C_4$ alkyl, or $C_1C_4$ alkoxy; tetrazolo; or

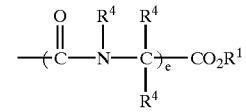

where, when the two R$^4$ groups attached to the same C are both alkyl, they optionally may be joined so that, when taken together with the C to which they are attached, they form a spiro ring of 3, 5, or 6 C atoms, or, where the R$^4$ attached to N and one R$^4$ attached to the adjacent C are both alkyl, they optionally may be joined so that, taken together with the atoms to which they are attached, they form a 5- or 6-membered heterocycle;

b is 0, 1, or 2;
d is 1, 2, or 3; and
e is 1 or 2.

13. A method of preparing the compound of claim 1, comprising the step of using as an intermediate a compound selected from the group consisting of N-Benzyl-N-{[(2R)-6-bromo-3,4-dihydro-2H-chromen-2-yl]methyl}amine (2S)-1-(Benzyl {[(2R)-6-bromo-3,4-dihydro-2H-chromen-2-yl]methyl}amino)-3-phenoxy-2-propanol;

(2S)-1-(Benzyl{[(2R)-6-bromo-3,4-dihydro-2H-chromen-2-yl]methyl}amino)-3-phenoxy-2-propanol hydrobromide;

Methyl 4-[(2R)-2-({benzyl[2S]-2-hydroxy-3-phenoxypropyl]amino}methyl)-3,4-dihydro-2H-chromen-6-yl]benzoate;

Methyl 4-[(2R)-2-({[(2S)-2-hydroxy-3-phenoxypropyl]amino}methyl)-3,4-dihydro-2H-chromen-6-yl]benzoate; and Methyl 4-[(2R)-2-({[(2S)-2-hydroxy-3-phenoxypropyl]amino}methyl)-3,4-dihydro-2H-chromen-6-yl]benzoate methanesulfonate.

14. A method of preparing the compound of Formula I comprising the reaction of a compound of Formula 2

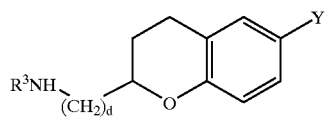

with a compound of Formula 3

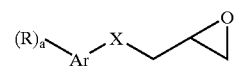

wherein
R is hydroxy, oxo, halo, cyano, nitro, $C_1$–$C_{10}$ alkyl optionally substituted with
phenyl, $C_1$–$C_{10}$haloalkyl, $CF_3$, NR$^1$R$^1$, SR$^1$, OR$^1$, $SO_2R^2$, OCOR$^2$, NR$^1$COR$^2$, COR$^2$, NR$^1$SO$_2$R$^2$, phenyl, or a 5- or 6-membered heterocycle with 1 to 4 heteroatoms selected independently from O, S, and N, each phenyl or heterocycle being optionally substituted with hydroxy, $R^1$, halo, cyano, $NR^1R^1$, $SR^1$, $CF_3$, $OR^1$, $C_3$–$C_8$ cycloalkyl, $NR^1COR^2$, $COR^2$, $SO_2R^2$, $OCOR^2$, $NR^1SO_2R^2$, $C_1$–$C_{10}$ alkyl, or $C_1$–$C_{10}$ alkoxy;

$R^1$ is hydrogen, $(CH_2)_d$—O—$(C_2)_d R^5$, where each d is selected independently, or $C_1$–$C_{10}$ alkyl optionally substituted with 1 to 4 substituents each independently selected from hydroxy, halo, $CO_2C_1$–$C_4$ alkyl, $CO_2H$, $S(O)_b C_1$–$C_{10}$ alkyl, $C_1$–$C_{10}$ alkoxy, and phenyl optionally substituted with $CO_2C_1$–$C_4$ alkyl or $CO_2H$, or $C_3$–$C_8$ cycloalkyl, phenyl, or naphthyl, each optionally substituted with 1 to 4 substituents each independently selected from halo, nitro, oxo, $C_1$–$C_{10}$ alkyl, $C_1$–$C_{10}$ alkoxy, and $C_1$–$C_{10}$ alkylthio; when two $R^1$ groups are attached to N as $NR^1R^1$, these $R^1$ groups may form together with the nitrogen to which they are attached, a heterocyclic ring containing 4 to 7 C atoms, 1 to 2 N atoms, and 0 to 1 O or S atoms;

$R^2$ is $R^1$; $OR^1$; $NR^1R^1$; $NHS(O)_b$phenyl optionally substituted with $C_1$–$C_4$ alkyl, $C_1$–$C_4$ alkoxy, halo, or nitro; $NHS(O)_b$naphthyl; NHS $(O)_b C_1$–$C_{10}$ alkyl; or a 5- or 6-membered heterocycle with one or more heteroatoms selected independently from O, S, and N, said heterocyclic moiety being optionally substituted with $R^1$;

$R^3$ is hydrogen, $C_1$–$C_{10}$ alkyl, benzyl, or $COR^2$;

$R^4$ is hydrogen, $C_1$–$C_{10}$ alkyl, $C_1$–$C_{10}$ alkyl-phenyl, or $C_1$–$C_{10}$ alkyl-pyridine;

Ar is phenyl optionally fused to a cyclohexyl, phenyl, or a 5- or 6-membered heterocycle containing one or more heteroatoms each independently selected from O, S, and N, each bicyclic moiety being optionally fused to phenyl, or a 5- or 6-membered heterocycle containing one or more heteroatoms each independently selected from N, S, and O, optionally fused to phenyl;

X is O or $S(O)_b$;

Y is halo, $R^1$, $OR^1$ $SR^1$, $CO_2R^1$, $NR^1R^1$, $S(O)_b$-phenyl-$CO_2R^1$, or phenyl optionally fused to another phenyl ring or to a 5- or 6-membered heterocycle containing one or more heteroatoms each independently selected from N, S, and O, or a 5- or 6-membered heterocycle containing one or more heteroatoms each independently selected from N, S, and O, optionally fused to a phenyl ring, each phenyl or heterocycle being optionally substituted with one or more substituents independently selected from $COR^2$, halo, $OR^1$, $NR^1R^1$, $R^1$, $C_1$–$C_{10}COR^2$, phenyl optionally substituted with halo, $C_1$–$C_4$ alkyl, or $C_1C_4$ alkoxy, tetrazolo; or

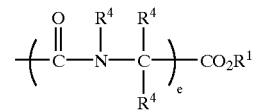

where, when the two $R^4$ groups attached to the same C are both alkyl, they optionally may be joined so that, when taken together with the C to which they are attached, they form a spiro ring of 3, 5, or 6 C atoms, or where the $R^4$ attached to N and one $R^4$ attached to the adjacent C are both alkyl, they optionally may be joined so that, taken together with the atoms to which they are attached, they form a 5- or 6-membered heterocycle;

a is 0, 1, 2, 3, 4, or 5; and b is 0, 1, or 2;

d is 1, 2, or 3;

e is 1 or 2.

15. A pharmaceutical composition comprising an effective amount of a compound of claim 1 or a pharmaceutically acceptable salt and esters thereof in combination with a pharmaceutically acceptable carrier.

16. A composition comprising an effective amount of a compound of claim 1 or a salt and esters thereof in combination with an inert carrier.

17. A method of treating diabetes, impaired fasting glucose, and impaired glucose tolerance which comprises administering to a subject in need thereof a pharmaceutically effective amount of a compound of Formula I, or a salt and ester thereof.

18. A method of treating obesity which comprises administering to a subject in need thereof a pharmaceutically effective amount of a compound of Formula I, or a salt and ester thereof.

19. A method of treating benign prostatic hyperplasia and incontinence which comprises administering to a subject in need thereof a pharmaceutically effective amount of a compound of Formula I, or a salt and ester thereof.

20. A method of treating atherosclerosis, which comprises administering to a subject in need thereof a pharmaceutically effective amount of a compound of Formula 1, or a salt and ester thereof.

* * * * *